US012661222B2

(12) United States Patent
Nir

(10) Patent No.: US 12,661,222 B2
(45) Date of Patent: Jun. 23, 2026

(54) EXPANSION AND LOCKING ASSEMBLIES WITH INTERTWINED WIRES

(71) Applicant: Edwards Lifesciences Corporation, Irvine, CA (US)

(72) Inventor: Noam Nir, Pardes-Hanna (IL)

(73) Assignee: Edwards Lifesciences Corporation, Irvine, CA (US)

( * ) Notice: Subject to any disclaimer, the term of this patent is extended or adjusted under 35 U.S.C. 154(b) by 751 days.

(21) Appl. No.: 18/096,511

(22) Filed: Jan. 12, 2023

(65) Prior Publication Data

US 2023/0172710 A1     Jun. 8, 2023

Related U.S. Application Data

(63) Continuation of application No. PCT/US2021/041926, filed on Jul. 16, 2021.

(60) Provisional application No. 63/052,688, filed on Jul. 16, 2020.

(51) Int. Cl.
    *A61F 2/24*          (2006.01)
(52) U.S. Cl.
    CPC .......... *A61F 2/2418* (2013.01); *A61F 2/2436* (2013.01); *A61F 2210/0014* (2013.01)
(58) Field of Classification Search
    CPC .... A61F 2/2418; A61F 2/2436; A61F 2/2439; A61F 2/243
    See application file for complete search history.

(56) References Cited

U.S. PATENT DOCUMENTS

| | | | |
|---|---|---|---|
| 3,409,013 A | 11/1968 | Berry | |
| 3,548,417 A | 12/1970 | Ronnie et al. | |
| 3,587,115 A | 6/1971 | Donald | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 4,035,849 A | 7/1977 | Angell et al. | |

(Continued)

FOREIGN PATENT DOCUMENTS

| | | |
|---|---|---|
| DE | 0144167 C | 9/1903 |
| DE | 2246526 A1 | 3/1973 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

(Continued)

*Primary Examiner* — Brian A Dukert
(74) *Attorney, Agent, or Firm* — Klarquist Sparkman, LLP

(57) ABSTRACT

The present invention is directed toward prosthetic heart valves that include an expandable frame provided with expansion and locking assemblies, which can be kept in a locked state by a twist formed along a portion of a wire of each expansion and locking assemblies. The present invention is further directed toward delivery assemblies that include actuation assemblies configured to actuate the expansion and locking assemblies, and to methods of utilizing the actuation assemblies and the expansion and locking assemblies.

19 Claims, 29 Drawing Sheets

(56) References Cited

U.S. PATENT DOCUMENTS

| | | | |
|---|---|---|---|
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 * | 6/2011 | Salahieh ............... A61F 2/2412 |
| | | 623/2.14 |
| 7,993,394 B2 | 8/2011 | Hariton et al. |
| 8,029,556 B2 | 10/2011 | Rowe |

(56)         References Cited

U.S. PATENT DOCUMENTS

| | | | |
|---|---|---|---|
| 8,075,611 | B2 | 12/2011 | Millwee et al. |
| 8,128,686 | B2 | 3/2012 | Paul et al. |
| 8,167,932 | B2 | 5/2012 | Bourang et al. |
| 8,291,570 | B2 | 10/2012 | Eidenschink et al. |
| 8,348,998 | B2 | 1/2013 | Pintor et al. |
| 8,449,606 | B2 | 5/2013 | Eliasen et al. |
| 8,454,685 | B2 | 6/2013 | Hariton et al. |
| 8,652,203 | B2 | 2/2014 | Quadri et al. |
| 8,685,055 | B2 | 4/2014 | VanTassel et al. |
| 8,747,463 | B2 | 6/2014 | Fogarty et al. |
| 9,078,781 | B2 | 7/2015 | Ryan et al. |
| 11,224,509 | B2 | 1/2022 | Dasi et al. |
| 2001/0021872 | A1 | 9/2001 | Bailey et al. |
| 2002/0026094 | A1 | 2/2002 | Roth |
| 2002/0032481 | A1 | 3/2002 | Gabbay |
| 2002/0138135 | A1 | 9/2002 | Duerig et al. |
| 2002/0143390 | A1 | 10/2002 | Ishii |
| 2002/0173842 | A1 | 11/2002 | Buchanan |
| 2003/0014105 | A1 | 1/2003 | Cao |
| 2003/0040791 | A1 | 2/2003 | Oktay |
| 2003/0050694 | A1 | 3/2003 | Yang et al. |
| 2003/0100939 | A1 | 5/2003 | Yodfat et al. |
| 2003/0158597 | A1 | 8/2003 | Quiachon et al. |
| 2003/0212454 | A1 | 11/2003 | Scott et al. |
| 2004/0024452 | A1 | 2/2004 | Kruse et al. |
| 2004/0039436 | A1 | 2/2004 | Spenser et al. |
| 2004/0078074 | A1 | 4/2004 | Anderson et al. |
| 2004/0186558 | A1 | 9/2004 | Pavcnik et al. |
| 2004/0186563 | A1 | 9/2004 | Lobbi |
| 2004/0186565 | A1 | 9/2004 | Schreck |
| 2004/0260389 | A1 | 12/2004 | Case et al. |
| 2005/0010285 | A1 | 1/2005 | Lambrecht et al. |
| 2005/0075725 | A1 | 4/2005 | Rowe |
| 2005/0075728 | A1 | 4/2005 | Nguyen et al. |
| 2005/0096736 | A1 | 5/2005 | Osse et al. |
| 2005/0096738 | A1 | 5/2005 | Cali et al. |
| 2005/0137686 | A1 | 6/2005 | Salahieh et al. |
| 2005/0188525 | A1 | 9/2005 | Weber et al. |
| 2005/0203614 | A1 | 9/2005 | Forster et al. |
| 2005/0203617 | A1 | 9/2005 | Forster et al. |
| 2005/0234546 | A1 | 10/2005 | Nugent et al. |
| 2006/0004469 | A1 | 1/2006 | Sokel |
| 2006/0025857 | A1 | 2/2006 | Bergheim et al. |
| 2006/0058872 | A1 | 3/2006 | Salahieh et al. |
| 2006/0074484 | A1 | 4/2006 | Huber |
| 2006/0108090 | A1 | 5/2006 | Ederer et al. |
| 2006/0149350 | A1 | 7/2006 | Patel et al. |
| 2006/0183383 | A1 | 8/2006 | Asmus et al. |
| 2006/0229719 | A1 | 10/2006 | Marquez et al. |
| 2006/0259136 | A1 | 11/2006 | Nguyen et al. |
| 2006/0259137 | A1 | 11/2006 | Artof et al. |
| 2006/0287717 | A1 | 12/2006 | Rowe et al. |
| 2007/0005131 | A1 | 1/2007 | Taylor |
| 2007/0010876 | A1 | 1/2007 | Salahieh et al. |
| 2007/0010877 | A1 | 1/2007 | Salahieh et al. |
| 2007/0112422 | A1 | 5/2007 | Dehdashtian |
| 2007/0162102 | A1 | 7/2007 | Ryan et al. |
| 2007/0203503 | A1 | 8/2007 | Salahieh et al. |
| 2007/0203575 | A1 | 8/2007 | Forster et al. |
| 2007/0203576 | A1 | 8/2007 | Lee et al. |
| 2007/0208550 | A1 | 9/2007 | Cao et al. |
| 2007/0213813 | A1 | 9/2007 | Segesser et al. |
| 2007/0233228 | A1 | 10/2007 | Eberhardt et al. |
| 2007/0260305 | A1 | 11/2007 | Drews et al. |
| 2007/0265700 | A1 | 11/2007 | Eliasen et al. |
| 2008/0021546 | A1 | 1/2008 | Patz et al. |
| 2008/0114442 | A1 | 5/2008 | Mitchell et al. |
| 2008/0125853 | A1 | 5/2008 | Bailey et al. |
| 2008/0154355 | A1 | 6/2008 | Benichou et al. |
| 2008/0183271 | A1 | 7/2008 | Frawley et al. |
| 2008/0208327 | A1 | 8/2008 | Rowe |
| 2008/0243245 | A1 | 10/2008 | Thambar et al. |
| 2008/0255660 | A1 | 10/2008 | Guyenot et al. |
| 2008/0275537 | A1 | 11/2008 | Limon |
| 2008/0294248 | A1 | 11/2008 | Yang et al. |
| 2009/0118826 | A1 | 5/2009 | Khaghani |
| 2009/0125118 | A1 | 5/2009 | Gong |
| 2009/0157175 | A1 | 6/2009 | Benichou |
| 2009/0276040 | A1 | 11/2009 | Rowe et al. |
| 2009/0281619 | A1 | 11/2009 | Le et al. |
| 2009/0287296 | A1 | 11/2009 | Manasse |
| 2009/0287299 | A1 | 11/2009 | Tabor et al. |
| 2009/0299452 | A1 | 12/2009 | Eidenschink et al. |
| 2009/0319037 | A1 | 12/2009 | Rowe et al. |
| 2010/0004735 | A1 | 1/2010 | Yang et al. |
| 2010/0049313 | A1 | 2/2010 | Alon et al. |
| 2010/0082094 | A1 | 4/2010 | Quadri et al. |
| 2010/0100176 | A1 | 4/2010 | Elizondo et al. |
| 2010/0168844 | A1 | 7/2010 | Toomes et al. |
| 2010/0185277 | A1 | 7/2010 | Braido et al. |
| 2010/0198347 | A1 | 8/2010 | Zakay et al. |
| 2010/0204781 | A1 | 8/2010 | Alkhatib |
| 2011/0015729 | A1 | 1/2011 | Jimenez et al. |
| 2011/0022157 | A1 | 1/2011 | Essinger et al. |
| 2011/0066224 | A1 | 3/2011 | White |
| 2011/0137397 | A1 | 6/2011 | Chau et al. |
| 2011/0218619 | A1 | 9/2011 | Benichou et al. |
| 2011/0319991 | A1 | 12/2011 | Hariton et al. |
| 2012/0030090 | A1 | 2/2012 | Johnston et al. |
| 2012/0089223 | A1 | 4/2012 | Nguyen et al. |
| 2012/0101571 | A1 | 4/2012 | Thambar et al. |
| 2012/0123529 | A1 | 5/2012 | Levi et al. |
| 2012/0259409 | A1 | 10/2012 | Nguyen et al. |
| 2013/0023985 | A1 | 1/2013 | Khairkhahan et al. |
| 2013/0046373 | A1 | 2/2013 | Cartledge et al. |
| 2013/0150956 | A1 | 6/2013 | Yohanan et al. |
| 2013/0166017 | A1 | 6/2013 | Cartledge et al. |
| 2013/0190857 | A1 | 7/2013 | Mitra et al. |
| 2013/0274873 | A1 | 10/2013 | Delaloye et al. |
| 2013/0310926 | A1 | 11/2013 | Hariton |
| 2013/0317598 | A1 | 11/2013 | Rowe et al. |
| 2013/0331929 | A1 | 12/2013 | Mitra et al. |
| 2014/0194981 | A1 | 7/2014 | Menk et al. |
| 2014/0200661 | A1 | 7/2014 | Pintor et al. |
| 2014/0209238 | A1 | 7/2014 | Bonyuet et al. |
| 2014/0222136 | A1 | 8/2014 | Geist et al. |
| 2014/0277417 | A1 | 9/2014 | Schraut et al. |
| 2014/0277419 | A1 | 9/2014 | Garde et al. |
| 2014/0277424 | A1 | 9/2014 | Oslund |
| 2014/0277563 | A1 | 9/2014 | White |
| 2014/0296962 | A1 | 10/2014 | Cartledge et al. |
| 2014/0330372 | A1 | 11/2014 | Weston et al. |
| 2014/0343670 | A1 | 11/2014 | Bakis et al. |
| 2014/0343671 | A1 | 11/2014 | Yohanan et al. |
| 2014/0350667 | A1 | 11/2014 | Braido et al. |
| 2015/0073545 | A1 | 3/2015 | Braido |
| 2015/0073546 | A1 | 3/2015 | Braido |
| 2015/0135506 | A1 | 5/2015 | White |
| 2015/0157455 | A1 | 6/2015 | Hoang et al. |
| 2016/0374802 | A1 | 12/2016 | Levi et al. |
| 2017/0014229 | A1 | 1/2017 | Nguyen-Thien-Nhon et al. |
| 2018/0028310 | A1 | 2/2018 | Gurovich et al. |
| 2018/0153689 | A1 | 6/2018 | Maimon et al. |
| 2018/0325665 | A1 | 11/2018 | Gurovich et al. |
| 2018/0344456 | A1 | 12/2018 | Barash et al. |
| 2019/0159894 | A1 | 5/2019 | Levi et al. |
| 2019/0192288 | A1 | 6/2019 | Levi et al. |
| 2019/0192289 | A1 | 6/2019 | Levi et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0850607 A1 | 7/1998 |
| EP | 1057460 A1 | 12/2000 |
| EP | 1088529 A2 | 4/2001 |
| EP | 1570809 A1 | 9/2005 |

(56) References Cited

FOREIGN PATENT DOCUMENTS

| | | | |
|---|---|---|---|
| FR | 2788217 | A1 | 7/2000 |
| FR | 2815844 | A1 | 5/2002 |
| GB | 2056023 | A | 3/1981 |
| SU | 1271508 | A1 | 11/1986 |
| WO | 1991017720 | A1 | 11/1991 |
| WO | 1992017118 | A1 | 10/1992 |
| WO | 1993001768 | A1 | 2/1993 |
| WO | 1997024080 | A1 | 7/1997 |
| WO | 1998029057 | A1 | 7/1998 |
| WO | 1999030646 | A1 | 6/1999 |
| WO | 1999033414 | A1 | 7/1999 |
| WO | 1999040964 | A1 | 8/1999 |
| WO | 1999047075 | A1 | 9/1999 |
| WO | 2000018333 | A1 | 4/2000 |
| WO | 2000041652 | A1 | 7/2000 |
| WO | 2000047139 | A1 | 8/2000 |
| WO | 2001035878 | A2 | 5/2001 |
| WO | 2001049213 | A2 | 7/2001 |
| WO | 2001054624 | A1 | 8/2001 |
| WO | 2001054625 | A1 | 8/2001 |
| WO | 2001062189 | A1 | 8/2001 |
| WO | 2001064137 | A1 | 9/2001 |
| WO | 2001076510 | A2 | 10/2001 |
| WO | 2002022054 | A1 | 3/2002 |
| WO | 2002036048 | A1 | 5/2002 |
| WO | 2002041789 | A2 | 5/2002 |
| WO | 2002043620 | A1 | 6/2002 |
| WO | 2002047575 | A2 | 6/2002 |
| WO | 2002049540 | A2 | 6/2002 |
| WO | 2003047468 | A1 | 6/2003 |
| WO | 2005034812 | A1 | 4/2005 |
| WO | 2005055883 | A1 | 6/2005 |
| WO | 2005084595 | A1 | 9/2005 |
| WO | 2005102015 | A2 | 11/2005 |
| WO | 2006014233 | A2 | 2/2006 |
| WO | 2006032051 | A2 | 3/2006 |
| WO | 2006034008 | A2 | 3/2006 |
| WO | 2006111391 | A1 | 10/2006 |
| WO | 2006127089 | A1 | 11/2006 |
| WO | 2006138173 | A2 | 12/2006 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008147964 | A1 | 12/2008 |
| WO | 2008150529 | A1 | 12/2008 |
| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009094188 | A2 | 7/2009 |
| WO | 2009116041 | A2 | 9/2009 |
| WO | 2009149462 | A2 | 12/2009 |
| WO | 2010011699 | A2 | 1/2010 |
| WO | 2010121076 | A2 | 10/2010 |
| WO | 2013106585 | A1 | 7/2013 |
| WO | 2015085218 | A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al, "Prototype Stent: Invivo Swine Studies in the Biliary System", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

EXPANSION AND LOCKING ASSEMBLIES WITH INTERTWINED WIRES

CROSS REFERENCE TO RELATED APPLICATION

This application is a continuation of a PCT Application No. PCT/US2021/041926, filed Jul. 16, 2021, which claims the benefit of U.S. Provisional Patent Application No. 63/052,688, filed Jul. 16, 2020, where each of above-referenced applications is incorporated herein by reference in its entirety.

FIELD OF THE INVENTION

The present disclosure relates to implantable, mechanically expandable prosthetic devices, such as prosthetic heart valves, and to methods and delivery assemblies for, and including, such devices.

BACKGROUND OF THE INVENTION

Native heart valves, such as the aortic, pulmonary and mitral valves, function to assure adequate directional flow from and to the heart, and between the heart's chambers, to supply blood to the whole cardiovascular system. Various valvular diseases can render the valves ineffective and require replacement with artificial valves. Surgical procedures can be performed to repair or replace a heart valve. Surgeries are prone to an abundance of clinical complications, hence alternative less invasive techniques of delivering a prosthetic heart valve over a catheter and implanting it over the native malfunctioning valve, have been developed over the years.

One exemplary approach for prosthetic valve implantation in a minimally invasive procedure includes mounting a prosthetic heart valve in a crimped state on a distal end of a delivery apparatus, which can be advanced to the site of implantation through the patient's vasculature. In a retrograde approach, the delivery apparatus is advanced, for example, through the femoral artery and the aorta. Once the prosthetic valve reached the desired implantation site, it is expanded to a functional size against the native anatomy, such as the annulus of a native valve.

Mechanically expandable valves are a category of prosthetic valves that rely on a mechanical actuation mechanism for expansion. The actuation mechanism usually includes a plurality of actuation/locking assemblies, releasably connected to respective actuation members of the valve delivery system, controlled via the handle for actuating the assemblies to expand the valve to a desired diameter. The assemblies may optionally lock the valve's position to prevent undesired recompression thereof, and disconnection of the delivery system's actuation member from the valve actuation/locking assemblies, to enable retrieval thereof once the valve is properly positioned at the desired site of implantation.

Despite the recent advancements in prosthetic valve technology, there remains a need for improved transcatheter heart valves and delivery systems for such valves.

SUMMARY OF THE INVENTION

The present disclosure is directed toward devices and assemblies for expanding and locking prosthetic valves, as well as related methods and devices for such assemblies. In several embodiments, the disclosed assemblies are configured for delivering replacement heart valves into a heart of a patient, wherein the replacement heart valves may be expanded and locked in a desired diameter at the implantation site.

According to one aspect of the invention, there is provided a prosthetic valve comprising a frame having an inflow end and an outflow end, wherein the frame is movable between a radially compressed and a radially expanded state. The prosthetic valve further comprises at least one expansion and locking mechanism, which includes a guide member, a base member, and a wire.

The guide member is coupled to the frame at a first location, and comprises: a guide member first surface, a guide member second surface, and two guide member through-holes extending between the guide member first surface and the guide member second surface.

The base member is coupled to the frame at a second location spaced apart from the first location, and comprises: a base member first surface, a base member second surface, and two base member through-holes extending between the base member first surface and the base member second surface.

The wire comprises a wire base end portion looped over the base member second surface, and two wire axial portions extending from the base member second surface, through the base member through-holes, toward and through the guide member through-holes. Each wire axial portion defines an axial lock portion at the region that extends beyond the guide member first surface.

Movement of the base member in a first direction, relative to the guide member, causes the frame to foreshorten axially and expand radially.

The axial lock portions are configured to form together a twist disposed over the guide member first surface when they are intertwined together, such that when the twist is formed, it is configured to prevent, along with the wire base end portion, recompression of the frame.

According to some embodiments, the wire comprises a plastically deformable material.

According to some embodiments, the guide member comprises a guide member fastener.

According to some embodiments, the base member comprises a base member fastener.

According to some embodiments, the frame comprises inflow apices, outflow apices, and non-apical junctions between the inflow apices and the outflow apices, wherein the first location is a non-apical junction.

According to some embodiments, the diameter of each guide member through-hole and the diameter of each base member through-hole, is not greater than 150% of the diameter of the wire.

According to some embodiments, the diameter of each guide member through-hole and the diameter of each base member through-hole, is not greater than 120% of the diameter of the wire.

According to some embodiments, the diameter of each guide member through-hole and the diameter of each base member through-hole, is not greater than 110% of the diameter of the wire.

According to some embodiments, the diameter of each guide member through-hole and the diameter of each base member through-hole, is not greater than 105% of the diameter of the wire.

According to some embodiments, each axial lock portion comprises an attachment interface.

According to some embodiments, the attachment interface is an eyelet.

According to some embodiments, the wire defines a closed loop, such that both wire axial portions are joined by a pull end portion, opposite to the wire base end portion.

According to some embodiments, the guide member through-holes are radially spaced from each other.

According to some embodiments, the guide member through-holes are laterally spaced from each other.

According to some embodiments, the base member through-holes are radially spaced from each other.

According to some embodiments, the base member through-holes are laterally spaced from each other.

According to some embodiments, the prosthetic valve further comprises the twist formed by the axial lock portions intertwined with each other.

According to some embodiments, the twist does not extend proximally beyond the outflow end.

According to another aspect of the invention, there is provided a delivery assembly comprising a prosthetic valve and a delivery apparatus. The prosthetic valve comprises a frame and at least one expansion and locking assembly. The frame has an inflow end and an outflow end, and is movable between a radially compressed and a radially expanded state.

The expansion and locking assembly comprises a guide member coupled to the frame at a first location, a base member, coupled to the frame at a second location spaced apart from the first location, and a wire. The guide member is defined between a guide member first surface and a guide member second surface. The wire comprises a wire base end portion looped over the base member, and two wire axial portions extending from the wire base end portion, through the base member, toward and through guide member.

The delivery apparatus comprises a handle, a delivery shaft extending distally from the handle, and at least one actuation assembly extending from the handle through the delivery shaft, the actuation assembly comprising a sleeve. The sleeve comprises a sleeve outer surface, a sleeve distal end, at least one sleeve distal opening, and at least one sleeve channel extending from the at least one sleeve distal opening.

The sleeve is configured to accommodate a portion of the wire within the at least one sleeve channel, such that the portion of the wire accommodated within the sleeve is axially movable with respect to the sleeve.

Movement of the base member in a first direction, relative to the guide member, causes the frame to foreshorten axially and expand radially.

The wire axial portions define axial lock portions at the region that extends beyond the guide member first surface. Rotation of the sleeve is configured to intertwine the wire axial portions so as to form a twist disposed over the guide member first surface, such that when the twist is formed, it is configured to prevent, along with the wire base end portion, recompression of the frame.

According to some embodiments, the wire comprises a plastically deformable material.

According to some embodiments, the guide member comprises a guide member fastener.

According to some embodiments, the base member comprises a base member fastener.

According to some embodiments, the frame comprises inflow apices, outflow apices, and non-apical junctions between the inflow apices and the outflow apices, wherein the first location is a non-apical junction.

According to some embodiments, the diameter of each guide member through-hole and the diameter of each base member through-hole, is not greater than 150% of the diameter of the wire.

According to some embodiments, the diameter of each guide member through-hole and the diameter of each base member through-hole, is not greater than 120% of the diameter of the wire.

According to some embodiments, the diameter of each guide member through-hole and the diameter of each base member through-hole, is not greater than 110% of the diameter of the wire.

According to some embodiments, the diameter of each guide member through-hole and the diameter of each base member through-hole, is not greater than 105% of the diameter of the wire.

According to some embodiments, the sleeve has sufficient rigidity, configured to resist bending or buckling thereof, when the sleeve is pressed against, and applies a distally oriented force against, the guide member.

According to some embodiments, the at least one sleeve distal opening comprises two sleeve distal opening, wherein the at least one sleeve channel comprises two sleeve channels.

According to some embodiments, the diameter of each sleeve channel is not greater than 150% of the diameter of the wire.

According to some embodiments, the diameter of each sleeve channel is not greater than 120% of the diameter of the wire.

According to some embodiments, the diameter of each sleeve channel is not greater than 110% of the diameter of the wire.

According to some embodiments, the diameter of each sleeve channel is not greater than 105% of the diameter of the wire.

According to some embodiments, the sleeve further comprises two sleeve side openings defined at the sleeve outer surface, such that each sleeve channel extends between a corresponding sleeve distal opening and a corresponding sleeve side opening.

According to some embodiments, each actuation assembly further comprises a couple of pull members extending from the handle, wherein each pull member is coupled to an attachment interface of the corresponding wire axial portion.

According to some embodiments, each wire axial portion extends into a corresponding sleeve channel through the corresponding sleeve distal opening, wherein the attachment interface is positioned within the sleeve channel, and wherein the wire axial portion exits the sleeve channel through the corresponding sleeve side opening.

According to some embodiments, the diameter of each sleeve channel is not greater than 150% of the diameter of the pull member.

According to some embodiments, the diameter of each sleeve channel is not greater than 120% of the diameter of the pull member.

According to some embodiments, the diameter of each sleeve channel is not greater than 110% of the diameter of the pull member.

According to some embodiments, the diameter of each sleeve channel is not greater than 105% of the diameter of the pull member.

According to some embodiments, the diameter of each sleeve channel is not greater than 150% of the diameter of the attachment interface.

According to some embodiments, the diameter of each sleeve channel is not greater than 120% of the diameter of the attachment interface.

According to some embodiments, the diameter of each sleeve channel is not greater than 110% of the diameter of the attachment interface.

According to some embodiments, the diameter of each sleeve channel is not greater than 105% of the diameter of the attachment interface.

According to some embodiments, each actuation assembly further comprises a cutting shaft extending concentrically over the sleeve, and movable axially relative thereto, the cutting shaft comprising a blade.

According to some embodiments, the blade is configured to cut the wire.

According to some embodiments, the sleeve channels extend axially along the length of the sleeve.

According to some embodiments, each wire axial extension comprises an eyelet, wherein each actuation assembly further comprises two pull members, each pull member looped through the eyelet such that two strands thereof extend proximally from the eyelet.

According to some embodiments, the diameter of each sleeve channel is not greater than 300% of the diameter of the diameter of a single strand.

According to some embodiments, the diameter of each sleeve channel is not greater than 250% of the diameter of the diameter of a single strand.

According to some embodiments, the diameter of each sleeve channel is not greater than 210% of the diameter of the diameter of a single strand.

According to some embodiments, the wire defines a closed loop, such that both wire axial portions are joined by a pull end portion, opposite to the wire base end portion.

According to some embodiments, the actuation assembly further comprises a pull member attached to a quick release hook, configured to transition between a closed configuration and an open configuration.

According to some embodiments, the quick release hook comprises a hook body, and a spring-loaded gate hinged thereto.

According to some embodiments, the sleeve channel is dimensioned to accommodate the quick release hook in a closed configuration.

According to some embodiments, the actuation assembly further comprises a pull member looped through the pull end portion such that two strands of the pull member extend proximally from the pull end portion.

According to some embodiments, the actuation assembly further comprises a pull member having a bendable distal portion made of a shape-memory material and configured to transition between a biased configuration, in which the bendable distal portion is bent over itself, and an unbiased configuration, wherein the pull end portion is releasably attached to the bendable distal portion in its biased configuration.

According to some embodiments, the prosthetic valve further comprises the twist formed by the axial lock portions intertwined with each other.

According to some embodiments, the twist does not extend proximally beyond the outflow end.

According to some embodiments, the sleeve further comprises a threaded proximal portion.

According to some embodiments, the threaded proximal portion is attached to the handle.

According to yet another aspect of the invention, there is provided a method for expanding and locking a prosthetic valve. The method comprises a step of providing a delivery assembly which comprises a delivery apparatus releasably coupled to a prosthetic valve, wherein the delivery apparatus comprises a handle and at least one actuation assembly extending therefrom. Each actuation assembly comprises a sleeve with at least one sleeve channel.

The prosthetic valve comprises frame and at least one expansion and locking assembly. Each expansion and locking assembly comprises a guide member coupled to the frame at a first location, a base member coupled to the frame at a second location which is axially spaced from the first location, and a wire having a wire base end portion looped over a surface of the base member, and two wire axial portions extending from the wire base end portion, through the base member, toward and through the guide member.

According to some embodiments, the method further comprises a step of approximating the sleeve to the guide member such that a distal end thereof contacts the guide member.

According to some embodiments, the method further comprises a step of utilizing the actuation assembly and the wire to approximate the base member and the guide member toward each other, thereby expanding the frame.

According to some embodiments, the step of utilizing the actuation assembly and the wire comprises applying a pull force on the wire, while holding the sleeve in place so as to apply a counter-force against the guide member.

According to some embodiments, the step of utilizing the actuation assembly and the wire comprises pushing the sleeve to apply a pushing force against the guide member, thereby moving the guide member toward the base member, while keeping the wire tensioned in a manner that will hold the base member in place.

According to some embodiments, the step of utilizing the actuation assembly and the wire comprises simultaneously applying a pull force on the wire, while pushing the sleeve to apply a pushing force against the guide member.

According to some embodiments, applying pull force on the wire comprises applying a pull force to two pull members that extend from the handle, and are coupled to attachment interfaces of the axial pull portions.

According to some embodiments, applying pull force on the wire comprises simultaneously applying a pull force to a total of four strands of two pull members that extend from the handle, wherein two strands of each pull members extend proximally from an eyelet of each wire axial portion, through which the corresponding pull member is looped.

According to some embodiments, applying pull force on the wire comprises applying a pull force to a pull member attached to a quick release hook, wherein a pull end portion of the wire is looped through the quick release hook, and wherein the quick release hook is retained in a closed state within the sleeve channel.

According to some embodiments, applying pull force on the wire comprises applying a pull force to a pull member having a bendable distal portion made of a shape-memory material, wherein the bendable distal portion is configured to transition between a biased configuration, in which the bendable distal portion is bent over itself, and an unbiased configuration, wherein a pull end portion of the wire is releasably attached to the bendable distal portion in its biased configuration, and wherein the bendable distal portion is retained in the biased configuration within the sleeve channel.

According to some embodiments, applying pull force on the wire comprises applying a pull force to two strands of a pull member that extends from the handle and is looped through a pull end portion of the wire.

According to some embodiments, the method further comprises a step of pulling the sleeve away from the guide member, thereby exposing axial lock portions extending between the guide member and a distal end of the sleeve.

According to some embodiments, each wire axial portion comprises an attachment interface, wherein the step of pulling the sleeve is executed such that the attachment interfaces remain within the at least one sleeve channel.

According to some embodiments, each wire axial portion comprises an eyelet, wherein the step of pulling the sleeve is executed such that the eyelets remain within the at least one sleeve channel.

According to some embodiments, the wire comprises a pull end portion looped through a quick release hook which is attached to a pull member extending therefrom, and the step of pulling the sleeve is executed such that the quick release hook remains within the sleeve channel.

According to some embodiments, the wire comprises a pull end portion looped through a quick release hook which is attached to a pull member extending therefrom, wherein the step of pulling the sleeve is executed such that the pull end portion remains within the sleeve channel.

According to some embodiments, the wire comprises a pull end portion looped through a bendable distal portion of a pull member, in a biased configuration of the bendable distal portion in which it is folded over itself, wherein the step of pulling the sleeve is executed such that the bendable distal portion remains within the sleeve channel.

According to some embodiments, the wire comprises a pull end portion looped through a bendable distal portion of a pull member, in a biased configuration of the bendable distal portion in which it is folded over itself, wherein the step of pulling the sleeve is executed such that the pull end portion remains within the sleeve channel.

According to some embodiments, the wire axial portions extend into the sleeve channel, and are joined together via a pull end portion of the wire, wherein a pull member is looped through the pull end portion, and wherein the step of pulling the sleeve is executed such that the pull end portion remains within the corresponding sleeve channels.

According to some embodiments, the method further comprises a step of rotating the sleeve around its axis of symmetry, so as to intertwine the axial lock portions over each other, thereby forming a twist disposed over the guide member.

According to some embodiments, the sleeve comprises a threaded proximal portion, wherein the step of pulling the sleeve away from the guide member is performed by threading the threaded proximal portion so as to facilitate rotational movement of the sleeve around its axis of symmetry, simultaneous to the axial pulling of the sleeve, and wherein the rotational movement is configured to intertwine the axial lock portions over each other, thereby forming a twist disposed over the guide member.

According to some embodiments, the wire axial portions extend into sleeve channels of the sleeve, exit the sleeve channels through sleeve side openings, and extend proximally from the sleeve side openings, wherein the method further comprises sliding a cutting shaft over the sleeve toward the side openings, thereby cutting the axial lock portions.

According to some embodiments, the wire axial portions extend into sleeve channels of the sleeve, wherein pull members, which are attached to the wire axial portions within the sleeve channels, exit the sleeve channels through sleeve side openings, and extend proximally from the sleeve side openings, and wherein the method further comprises sliding a cutting shaft over the sleeve toward the side openings, thereby cutting the pull members.

According to some embodiments, the wire axial portions extend into sleeve channels of the sleeve, wherein pull members are looped through eyelets of the wire axial portions, such that two strands of each pull member extend proximally from the eyelet, and wherein the method further comprises a step of pulling a single strand of each pull member, while allowing the opposite strand to freely move toward a corresponding eyelet, until it is released therefrom.

According to some embodiments, the wire axial portions extend into the sleeve channel, and are joined together via a pull end portion of the wire, which is looped through a quick release hook attached to a pull member extending proximally therefrom, wherein the quick release hook is retained in a closed configuration within the sleeve channel, and wherein the method further comprises pulling the sleeve relative to the quick release hook, so as to expose the quick release hook, allowing it to transition to its open configuration, thereby allowing the pull end portion of the wire to disengage therefrom.

According to some embodiments, the wire axial portions extend into the sleeve channel, and are joined together via a pull end portion of the wire which is looped through a bendable distal portion of a pull member, wherein the bendable distal portion is retained in a biased configuration in which it is folded over itself within the sleeve channel, and wherein the method further comprises pulling the sleeve relative to the bendable distal portion, so as to expose a second pull-member section of the pull-member section and allowing it to transition to its unbiased configuration, thereby allowing the pull end portion of the wire to disengage therefrom.

According to some embodiments, the wire axial portions extend into the sleeve channel, and are joined together via a pull end portion of the wire, wherein a pull member is looped through the pull end portion such that two strands of the pull member extend proximally from the pull end portion, and wherein the method further comprises a step of pulling a single strand of the pull member, while allowing the opposite strand to freely move toward the pull end portion, until it is released therefrom.

According to some embodiments, the method further comprises a step of retrieving the delivery apparatus, along with the actuation assemblies, from the prosthetic valve.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the invention will become more apparent from the following detailed description, which proceeds with reference to the accompanying figures.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

9

10

Figure 1:
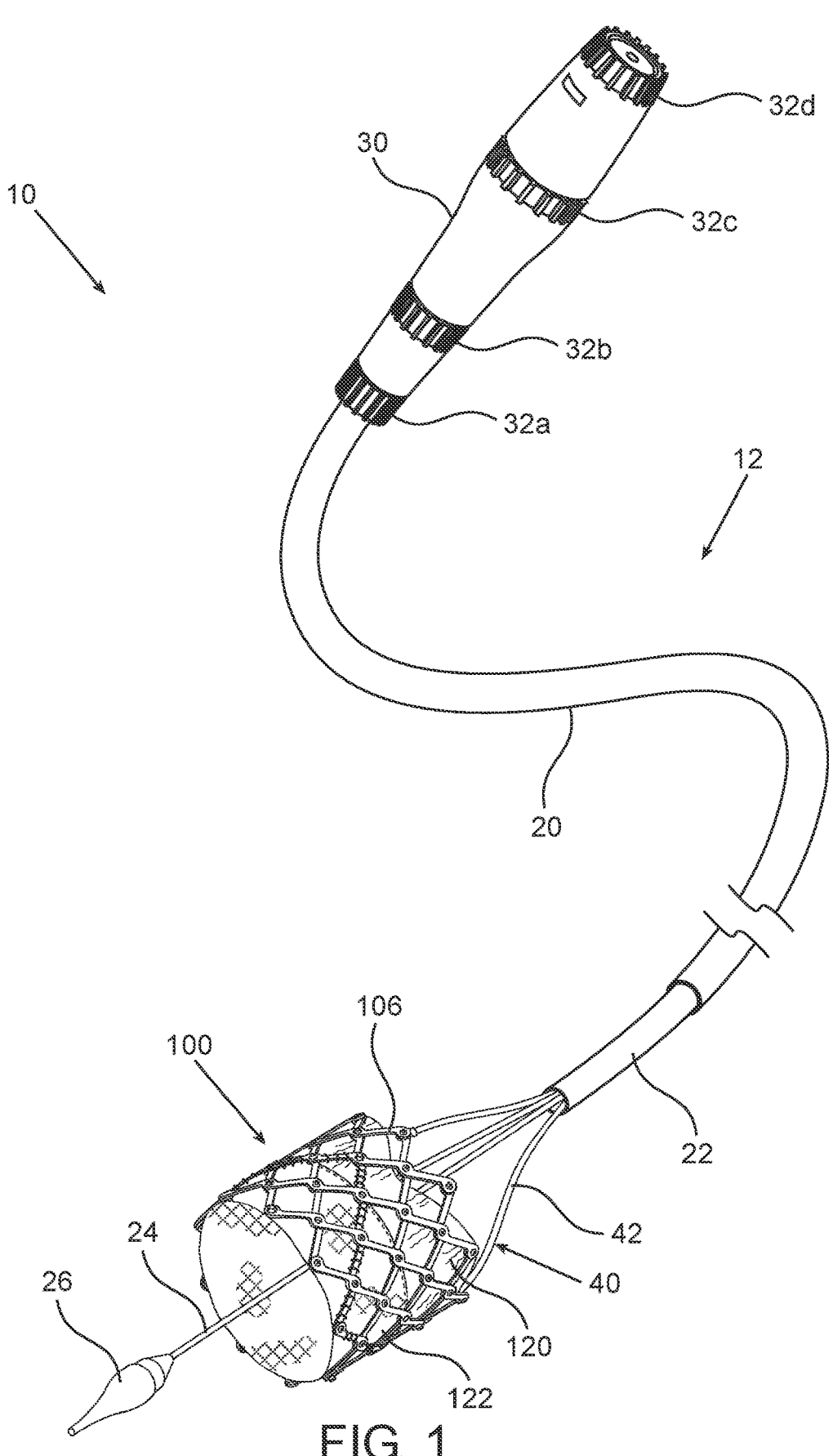

In the Figures:

FIG. 1 shows a view in perspective of a delivery assembly comprising a delivery apparatus carrying a prosthetic valve, according to some embodiments.

Figure 2:
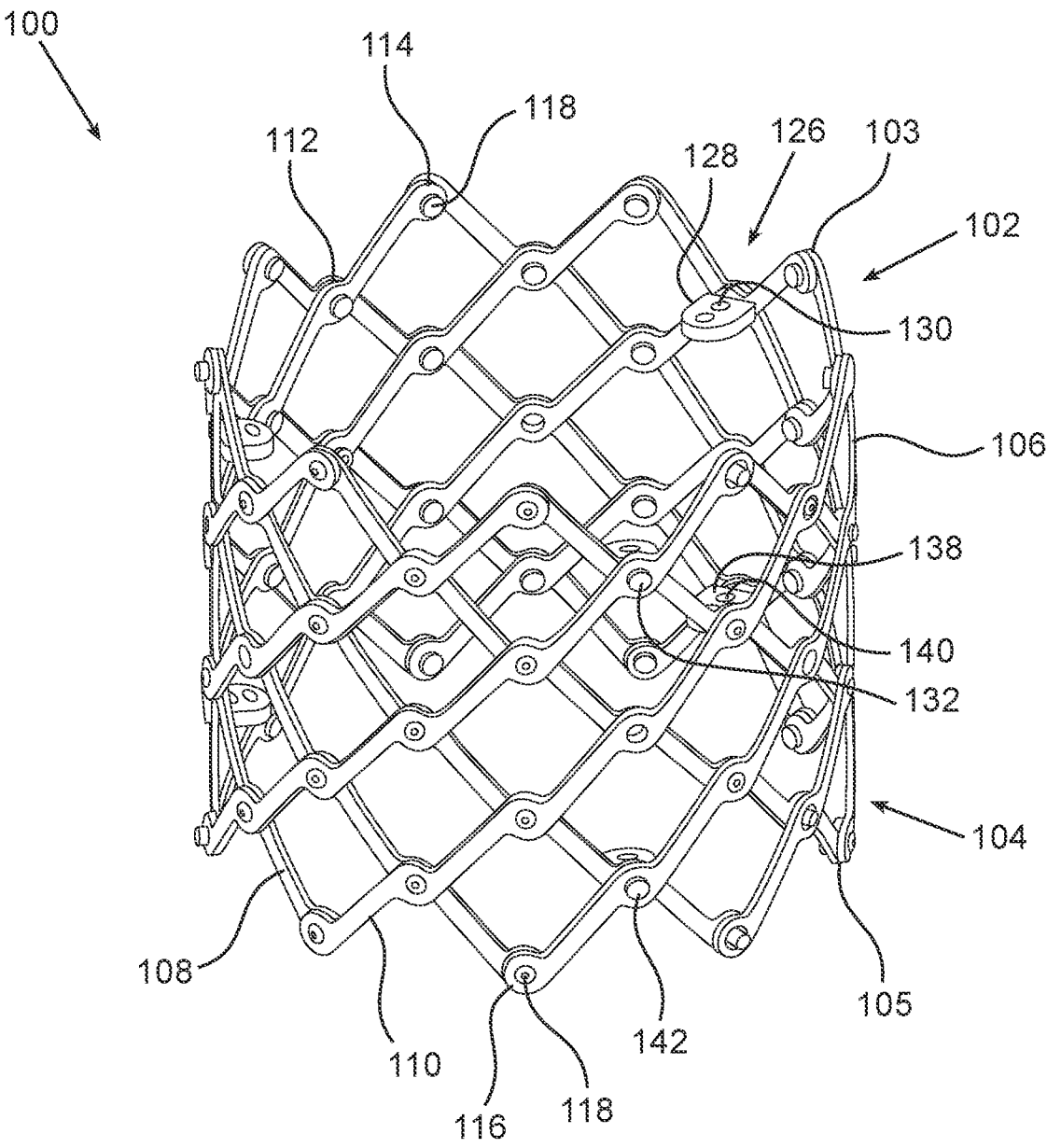

FIG. 2 shows a view in perspective of a prosthetic valve, according to some embodiments.

Figure 3:
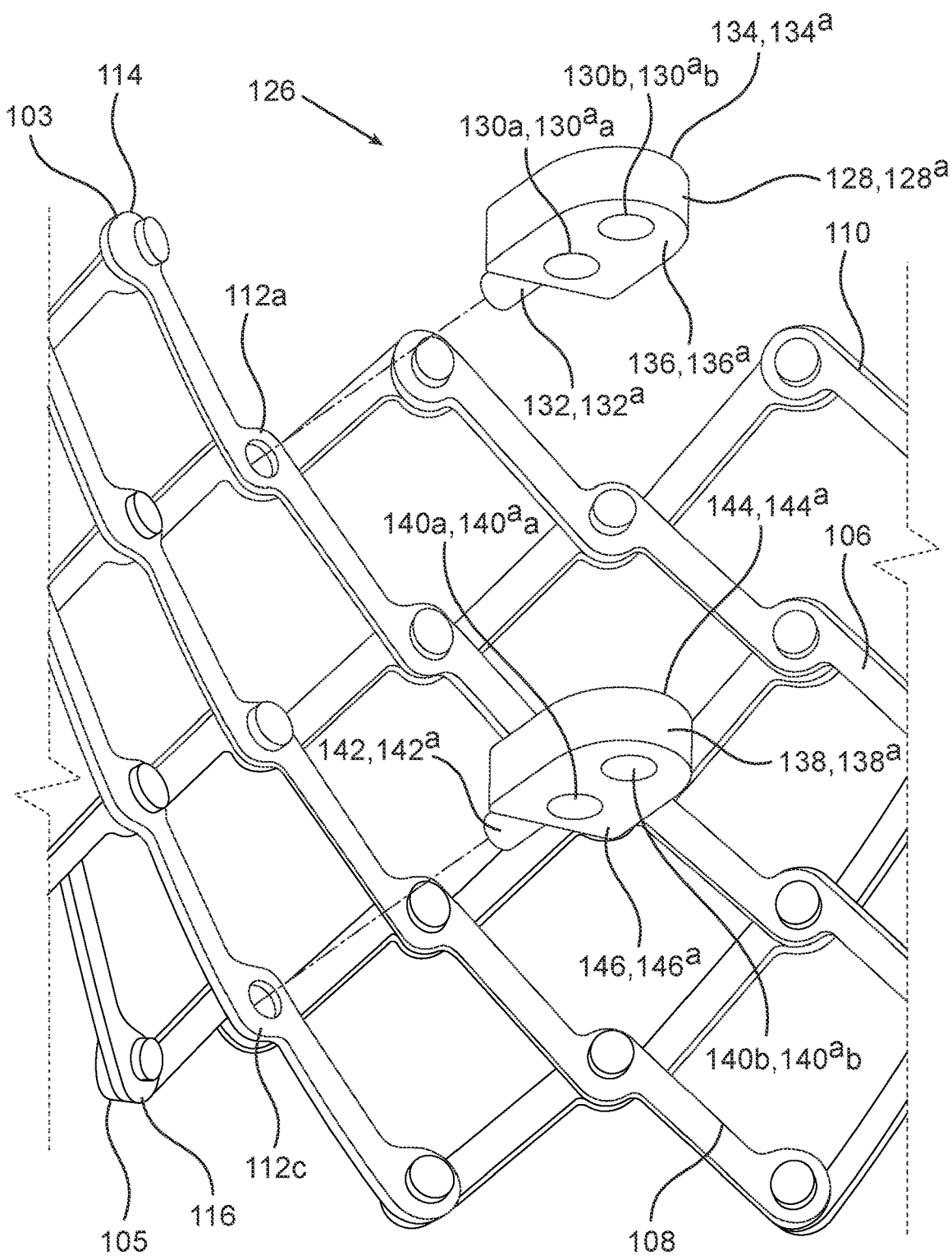

FIG. 3 shows an enlarged view of a portion of a prosthetic valve, with components of an expansion and locking mechanism pre-assembled to the frame of the valve, according to some embodiments.

Figure 4:
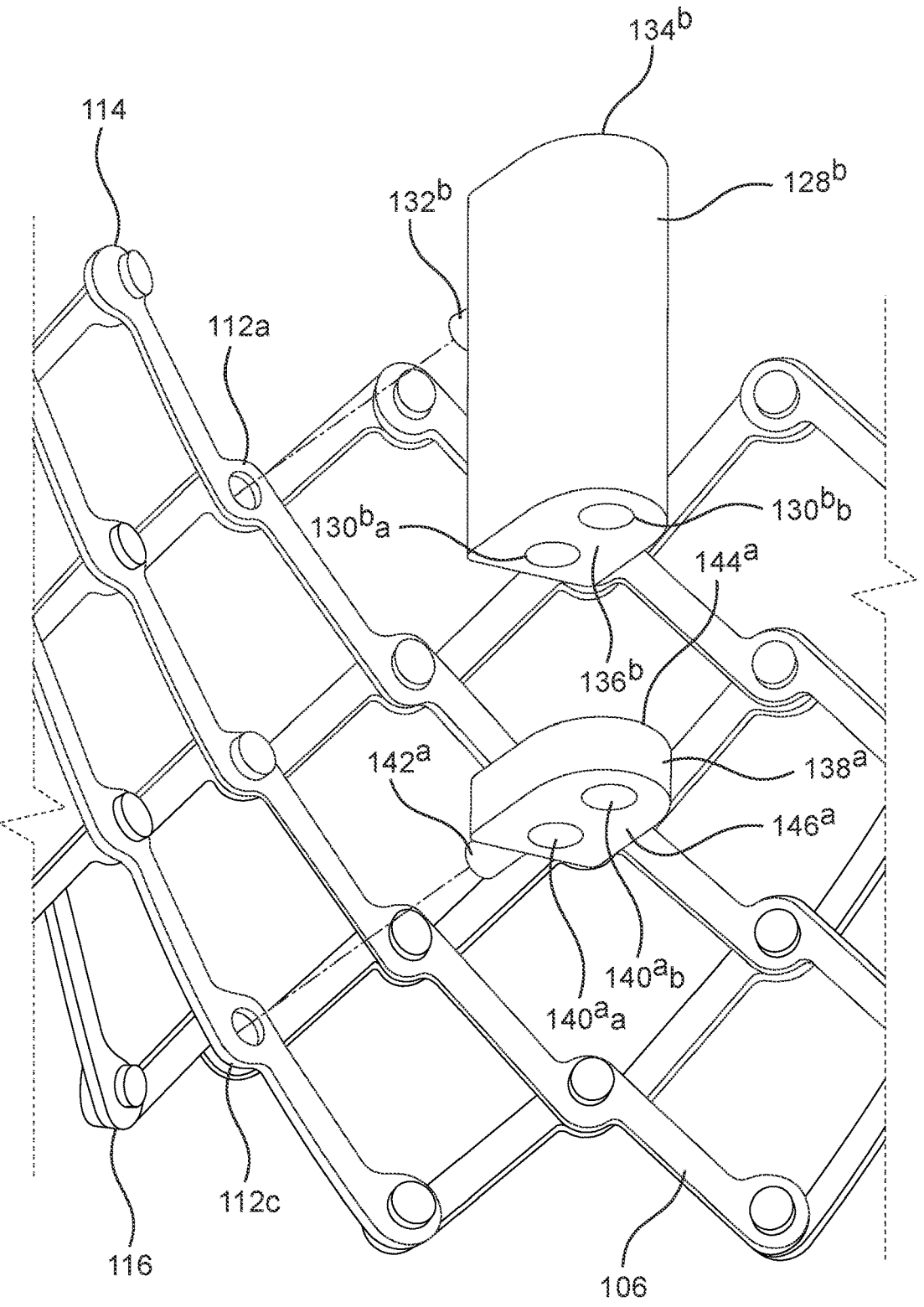

FIG. 4 shows an enlarged view of a portion of a prosthetic valve, with components of an expansion and locking mechanism pre-assembled to the frame of the valve, according to additional embodiments.

FIGS. 5A-5F show various stages of a valve expansion procedure utilizing an actuation assembly in combination with an expansion and locking assembly, according to some embodiments.

FIGS. 6A-6F show various stages of a valve expansion procedure utilizing an actuation assembly in combination with an expansion and locking assembly, according to additional embodiments.

FIGS. 7A-7F show various stages of a valve expansion procedure utilizing an actuation assembly in combination with an expansion and locking assembly, according to additional embodiments.

FIGS. 8A-8F show various stages of a valve expansion procedure utilizing an actuation assembly in combination with an expansion and locking assembly, according to additional embodiments.

FIGS. 9A-9F show various stages of a valve expansion procedure utilizing an actuation assembly in combination with an expansion and locking assembly, according to additional embodiments.

FIGS. 10A-10E show various stages of a valve expansion procedure utilizing an actuation assembly in combination with an expansion and locking assembly, according to additional embodiments.

Figure 11:
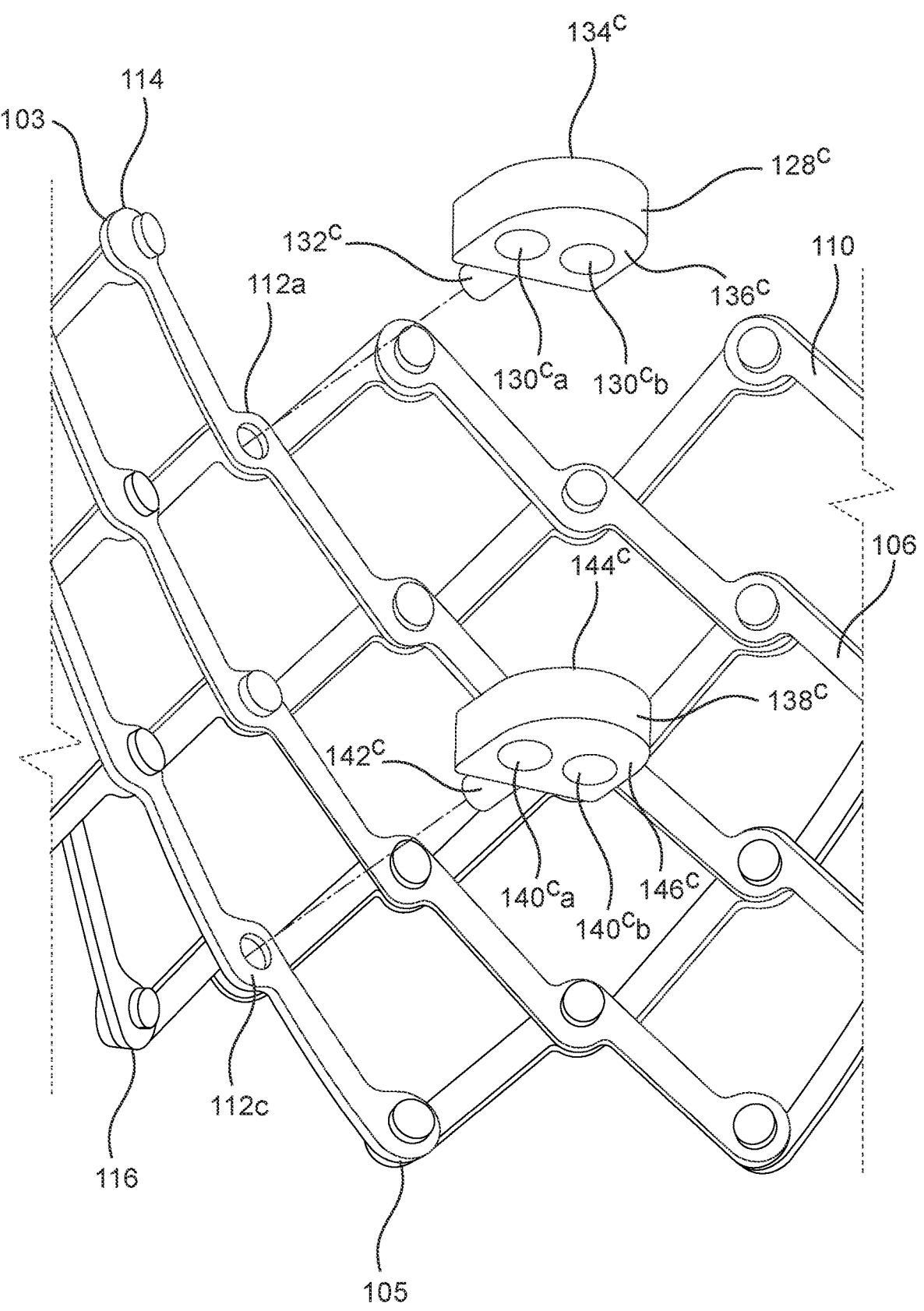

FIG. 11 shows an enlarged view of a portion of a prosthetic valve, with components of an expansion and locking mechanism pre-assembled to the frame of the valve, according to additional embodiments.

DETAILED DESCRIPTION OF SOME EMBODIMENTS

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present, or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the terms "have" or "includes" means "comprises." As used herein, "and/or" means "and" or "or," as well as "and" and "or".

Directions and other relative references may be used to facilitate discussion of the drawings and principles herein, but are not intended to be limiting. For example, certain terms may be used such as "inner," "outer," "upper," "lower," "inside," "outside,", "top," "bottom," "interior," "exterior," "left," right," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same.

Throughout the figures of the drawings, different superscripts for the same reference numerals are used to denote different embodiments of the same elements. Embodiments of the disclosed devices and systems may include any combination of different embodiments of the same elements. Specifically, any reference to an element without a superscript may refer to any alternative embodiment of the same element denoted with a superscript. In order to avoid undue clutter from having too many reference numbers and lead lines on a particular drawing, some components will be introduced via one or more drawings and not explicitly identified in every subsequent drawing that contains that component.

FIG. 1 shows a view in perspective of a delivery assembly 10, according to some embodiments. The delivery assembly 10 can include a prosthetic valve 100 and a delivery apparatus 12. The prosthetic valve 100 can be on or releasably coupled to the delivery apparatus 12. The delivery apparatus can include a handle 30 at a proximal end thereof, a nosecone shaft 24 extending distally from the handle 30, a nosecone 26 attached to the distal end of the nosecone shaft 24, a delivery shaft 22 extending over the nosecone shaft 24, and optionally an outer shaft 20 extending over the delivery shaft 22.

The term "proximal", as used herein, generally refers to the side or end of any device or a component of a device, which is closer to the handle 30 or an operator of the handle 30 when in use.

The term "distal", as used herein, generally refers to the side or end of any device or a component of a device, which is farther from the handle 30 or an operator of the handle 30 when in use.

The term "prosthetic valve", as used herein, refers to any type of a prosthetic valve deliverable to a patient's target site over a catheter, which is radially expandable and compressible between a radially compressed, or crimped, state, and a radially expanded state. Thus, a prosthetic valve 100 can be crimped or retained by a delivery apparatus 12 in a compressed state during delivery, and then expanded to the expanded state once the prosthetic valve 100 reaches the implantation site. The expanded state may include a range of diameters to which the valve may expand, between the compressed state and a maximal diameter reached at a fully expanded state. Thus, a plurality of partially expanded states may relate to any expansion diameter between radially compressed or crimped state, and maximally expanded state.

The term "plurality", as used herein, means more than one.

A prosthetic valve 100 of the current disclosure may include any prosthetic valve configured to be mounted within the native aortic valve, the native mitral valve, the native pulmonary valve, and the native tricuspid valve. While a delivery assembly 10 described in the current disclosure, includes a delivery apparatus 12 and a prosthetic valve 100, it should be understood that the delivery apparatus 12 according to any embodiment of the current disclosure can be used for implantation of other prosthetic devices aside from prosthetic valves, such as stents or grafts.

According to some embodiments, the prosthetic valve 100 is a mechanically expandable valve, and the delivery apparatus 12, further comprises a plurality of actuation assemblies 40 extending from the handle 30 through the delivery shaft 22. In the illustrated embodiment, the prosthetic valve 100 has three actuation assemblies 40, however, in other embodiments a greater or fewer number of actuation assemblies 40 can be used.

The prosthetic valve 100 can be delivered to the site of implantation via a delivery assembly 10 carrying the valve 100 in a radially compressed or crimped state, toward the target site, to be mounted against the native anatomy, by expanding the valve 100 via a mechanical expansion mechanism, as will be elaborated below.

The delivery assembly 10 can be utilized, for example, to deliver a prosthetic aortic valve for mounting against the aortic annulus, to deliver a prosthetic mitral valve for mounting against the mitral annulus, or to deliver a prosthetic valve for mounting against any other native annulus.

The nosecone 26 can be connected to the distal end of the nosecone shaft 24. A guidewire (not shown) can extend through a central lumen of the nosecone shaft 24 and an inner lumen of the nosecone 26, so that the delivery apparatus 12 can be advanced over the guidewire through the patient's vasculature.

A distal end portion of the outer shaft 20 can extend over the prosthetic valve 100 and contact the nosecone 26 in a delivery configuration of the delivery apparatus 12. Thus, the distal end portion of the outer shaft 20 can serve as a delivery capsule that contains, or houses, the prosthetic valve 100 in a radially compressed or crimped state for delivery through the patient's vasculature.

The outer shaft 20 and the delivery shaft 22 can be configured to be axially movable relative to each other, such that a proximally oriented movement of the outer shaft 20 relative to the delivery shaft 22, or a distally oriented movement of the delivery shaft 22 relative to the outer shaft 20, can expose the prosthetic valve 100 from the outer shaft 20. In some configurations, the prosthetic valve 100 is not housed within the outer shaft 20 during delivery. Thus, according to some optional configurations, the delivery apparatus 12 does not necessarily include an outer shaft 20.

As mentioned above, the proximal ends of the nosecone shaft 24, the delivery shaft 22, components of the actuation assemblies 40, and when present—the outer shaft 20, can be coupled to the handle 30. During delivery of the prosthetic valve 100, the handle 30 can be maneuvered by an operator (e.g., a clinician or a surgeon) to axially advance or retract components of the delivery apparatus 12, such as the nosecone shaft 24, the delivery shaft 22, and/or the outer shaft 20, through the patient's vasculature, as well as to expand or contract the prosthetic valve 100, for example by maneuvering the actuation assemblies 40, and to disconnect the prosthetic valve 100 from the delivery apparatus 12, as will be further elaborated throughout the current specification.

According to some embodiments, the handle 30 can include one or more operating interfaces, such as steerable or rotatable adjustment knobs 32, levers, sliders, buttons and other actuating mechanisms, which are operatively connected to different components of the delivery apparatus 12 and configured to produce axial movement of the delivery apparatus 12 in the proximal and distal directions, as well as to expand or contract the prosthetic valve 100 via various adjustment and activation mechanisms as will be further described below.

The handle 30 may further comprises one or more visual or auditory informative elements (not shown) configured to provide visual or auditory information and/or feedback to a user or operator of the delivery apparatus 12, such as a display, LED lights, speakers and the like.

FIG. 2 shows an exemplary mechanically expandable prosthetic valve 100 in an expanded state, according to some embodiments. The prosthetic valve 100 can comprise an inflow end portion 104 defining an inflow end 105, and an outflow end portion 102 defining an outflow end 103. In some instances, the outflow end 103 is the distal end of the prosthetic valve 100, and the inflow end 105 is the proximal end of the prosthetic valve 100. Alternatively, depending for example on the delivery approach of the valve, the outflow end can be the proximal end of the prosthetic valve, and the inflow end can be the distal end of the prosthetic valve. Soft components of the valve, such as leaflets and skirts (as will be elaborated herein below) are omitted from FIG. 2 for purposes of clarity.

The term "outflow", as used herein, refers to a region of the prosthetic valve through which the blood flows through and out of the valve 100, for example between the valve's central longitudinal axis and the outflow end 103.

The term "inflow", as used herein, refers to a region of the prosthetic valve through which the blood flows into the valve 100, for example between inflow end 105 and the valve's central longitudinal axis.

The valve 100 comprises a frame 106 composed of interconnected struts 110, and may be made of various suitable materials, such as stainless steel, cobalt-chrome alloy (e.g. MP35N alloy), or nickel titanium alloy such as Nitinol. According to some embodiments, the struts 110 are arranged in a lattice-type pattern. In the embodiment illustrated in FIG. 2, the struts 110 are positioned diagonally, or offset at an angle relative to, and radially offset from, the valve's central longitudinal axis, when the valve 100 is in an expanded state. It will be clear that the struts 110 can be offset by other angles than those shown in FIG. 2, such as being oriented substantially parallel to the valve's central longitudinal axis.

According to some embodiments, the struts 110 are pivotably coupled to each other. In the exemplary embodiment shown in FIG. 2, the end portions of the struts 110 are forming apices 114 at the outflow end 103 and apices 116 at the inflow end 105. The struts 110 can be coupled to each other at additional junctions 112 formed between the outflow apices 114 and the inflow apices 116. The junctions 112 can be equally spaced apart from each other, and/or from the apices 114, 116 along the length of each strut 110. Frame 106 may comprise openings or apertures at the regions of apices 114, 116 and junctions 112 of the struts 110. Respective hinges can be included at locations where the apertures of struts 110 overlap each other, via fasteners 118, such as rivets or pins, which extend through the apertures. The hinges can allow the struts 110 to pivot relative to one another as the frame 106 is radially expanded or compressed.

In alternative embodiments, the struts are not coupled to each other via respective hinges, but are otherwise pivotable or bendable relative to each other, so as to permit frame expansion or compression. For example, the frame can be formed from a single piece of material, such as a metal tube, via various processes such as, but not limited to, laser cutting, electroforming, and/or physical vapor deposition, while retaining the ability to collapse/expand radially in the absence of hinges and like.

The frame 106 further comprises a plurality of cells 108, defined between intersecting portions of struts 110. The shape of each cell 108, and the angle between intersecting portions of struts 110 defining the cell borders, vary during expansion or compression of the prosthetic valve 100. Further details regarding the construction of the frame and the prosthetic valve are described in U.S. Publication Nos. 2018/0153689; 2018/0344456; 2019/0060057, all of which are incorporated herein by reference.

A prosthetic valve 100 further comprises one or more leaflets 120 (see FIG. 1), e.g., three leaflets, configured to regulate blood flow through the prosthetic valve 100 from the inflow end 105 to the outflow end 103. The prosthetic valve 100 can include three leaflets 120 arranged to collapse in a tricuspid arrangement, or any other number of leaflets 120. The leaflets 120 are made of a flexible material, derived from biological materials (e.g., bovine pericardium or pericardium from other sources), bio-compatible synthetic materials, or other suitable materials. The leaflets may be coupled to the frame 106 via commissures, either directly or attached to other structural elements connected to the frame 106 or embedded therein, such as commissure posts. Further details regarding prosthetic valves, including the manner in which leaflets may be mounted to their frames, are described in U.S. Pat. Nos. 6,730,118, 7,393,360, 7,510,575, 7,993,394 and 8,252,202, and U.S. Patent Application No. 62/614,299, all of which are incorporated herein by reference.

According to some embodiments, the prosthetic valve 100 may further comprise at least one skirt or sealing member, such as the inner skirt 122 (see FIG. 1). The inner skirt 122 can be mounted on the inner surface of the frame 106, configured to function, for example, as a sealing member to prevent or decrease perivalvular leakage. The inner skirt 122 can further function as an anchoring region for the leaflets 120 to the frame 106, and/or function to protect the leaflets 120 against damage which may be caused by contact with the frame 106, for example during valve crimping or during working cycles of the prosthetic valve 100. Additionally, or alternatively, the prosthetic valve 100 can comprise an outer skirt (not shown) mounted on the outer surface of the frame 106, configure to function, for example, as a sealing member retained between the frame 106 and the surrounding tissue of the native annulus against which the prosthetic valve 100 is mounted, thereby reducing risk of paravalvular leakage past the prosthetic valve 100. Any of the inner skirt 122 and/or outer skirt can be made of various suitable biocompatible materials, such as, but not limited to, various synthetic materials (e.g., PET) or natural tissue (e.g. pericardial tissue).

According to some embodiments, a prosthetic valve 100, which can be a mechanical prosthetic valve, comprises at least one expansion and locking assembly 126, and preferably a plurality of expansion and locking assemblies 126. The expansion and locking assemblies 126 are configured to facilitate expansion of the valve 100, and in some instances, to lock the valve 100 at an expanded state, preventing unintentional recompression thereof, as will elaborated in greater detail hereinbelow. Although FIG. 2 illustrates three expansion and locking assemblies 126, mounted to the frame 106, and optionally equally spaced from each other around an inner surface thereof, it should be clear that a different number of expansion and locking assemblies 126 may be utilized, that the expansion and locking assemblies 126 can be mounted to the frame 106 around its outer surface, and that the circumferential spacing between expansion and locking assemblies 126 can be unequal.

The prosthetic valve 100 can be radially expanded by maintaining the outflow end 103 of the frame 106 at a fixed position while applying a force in the axial direction against the inflow end 105 toward the outflow end 103. Alternatively, the prosthetic valve 100 can be expanded by applying an axial force against the outflow end 103 while maintaining the inflow end 105 at a fixed position, or by applying opposing axial forces to the outflow and inflow ends 103, 105, respectively.

FIG. 3 shows an enlarged view of a portion of the prosthetic valve 100, with components of the expansion and locking assembly 126 pre-assembled to the frame 106, according to some embodiments. The expansion and locking assembly 126 comprises a guide member 128, coupled to a component of the valve 100, such as the frame 106, at a first location, and a base member 138 coupled to a component of the valve 100, such as the frame 106, at a second location, axially spaced from the first location.

The guide member 128 comprises a guide member fastener 132, which may be formed as a rivet or a pin extending radially outward from the guide member 128, configured to be received within respective openings or apertures of struts 110 intersecting at a junction 112 or an apex 114, 116. The guide member 128 may be provided in the form of a plate defined between a guide member first surface 134, facing away from the base member 138, and a guide member second surface 136, facing the base member 138.

The guide member 128 further comprises at least two guide channels or guide member through-holes 130, such as guide member through-holes $130^a$ and $130^b$ shown in FIG. 3, extending between the guide member first surface 134 and the guide member second surface 136. The guide through-holes are spaced from each other. FIG. 3 shows an exemplary embodiment of the guide member $128^a$, wherein the guide member through-holes $130^a$a and $130^a$b are radially spaced from each other.

The base member 138 comprises a base member fastener 142, which may be formed as a rivet or a pin extending radially outward from the base member 138, configured to be received within respective openings or apertures of struts 110 intersecting at a junction 112 or an apex 114, 116. The base member 138 may be provided in the form of a plate defined between a base member first surface 144, facing the guide member 128, and a base member second surface 146, facing away from the guide member 128.

The base member 138 further comprises at least two base channels or base member through-holes 140, such as base member through-holes 140$^a$ and 140$^b$ shown in FIG. 3, extending between the base member first surface 144 and the base member second surface 146. The base through-holes are spaced from each other. FIG. 3 shows an exemplary embodiment of the base member 138$^a$, wherein the base member through-holes 140$^a$a and 140$^a$b are radially spaced from each other.

According to some embodiments, the first location is a proximal location, and the second location is a distal location, as illustrated throughout the Figures. However, it will be understood that in alternative embodiments, the first location can be a distal location, while the second location can be a proximal location.

According to some embodiments, the guide member first surface 134 is a guide member proximal surface, the guide member second surface 136 is a guide member distal surface, the base member first surface 144 is a base member proximal surface, and the base member second surface 146 is a base member distal surface, as illustrated throughout the Figures. However, it will be understood that in alternative embodiments, the guide member first surface is a guide member distal surface, the guide member second surface is a guide member proximal surface, the base member first surface is a base member distal surface, and the base member second surface is a base member proximal surface.

According to some embodiments, either one of the guide member 128 and/or the base member 138 is an axially elongated member, instead of a plate-like member. FIG. 4 shows an exemplary embodiment of an axially elongated guide member 128$^b$, wherein the guide through-holes are formed as guide channels 130$^b$. While shown separately, it will be clear that a base member 138 can be formed as a similar elongated base member, provided with base through-holes are formed as base channels.

In some configurations, the guide member 128 and the base member 138 can be similarly formed. However, in alternative configurations, the guide member 128 may be different from the base member 138. For example, both the guide member 128 and the base member 138 can share a similar outer shape or contour, yet have different dimensions. In other configurations, different types of guide members 128 and base member 138 may be used in combination with each other. For example. FIG. 4 shows a configuration in which the expansion and locking assembly (126) is composed of an elongated guide member 128$^b$ and a plate-like base member 138$^a$. This combination is shown for the purpose of illustration and not limitation, and other combination are contemplated, such an elongated guide member 128$^b$ combined with an elongated base member 138$^b$ (not shown), a plate-like guide member 128$^a$ combined with an elongated base member 138$^b$, and a plate-like guide member 128$^a$ combined with a plate-like base member 138$^a$, as shown in FIG. 3.

According to some embodiments, the first location to which the guide member 128 is coupled is an apex, such as an outflow apex 114. According to some embodiments, the first location to which the guide member 128 is coupled is a non-apical junction 112$a$ at the outflow end portion 102, distal to the outflow apices 114, as illustrated throughout the Figures. The non-apical junction 112$a$ can be the most proximal junction 112, which is distal to the outflow apices 114.

According to some embodiments, the second location to which the base member 138 is coupled is an apex, such as an inflow apex 116. According to some embodiments, the second location to which the base member 138 is coupled is a junction 112$c$ at the inflow end portion 104, proximal to the inflow apices 116, as illustrated throughout the Figures. The junction 112$c$ can be the most distal junction 112, which is proximal to the inflow apices 116.

Reference is now made to FIGS. 5A-5F, showing different stages of expanding and locking a prosthetic valve 100, according to some embodiments. Each expansion and locking assembly 126 further comprises a wire 148 extending through the guide member through-holes 130 and the base member through-holes 140, wherein the wire 148 is a flexible, plastically deformable wire, comprising a wire base end portion 150, defining a bight or a U-shaped loop along the base member second surface 146 between both base member through-holes 140, and a couple of wire axial portion 152 extending from the wire base end portion 150, through the base member through-holes 140, between the base member 138 and the guide member 128, through the guide member through-holes 130, and to some extent, beyond the guide member first surface 134, such as proximal to the guide member first surface 134.

According to some embodiments, the diameter of the wire 148 is uniform across its length, such that any reference to the diameter for wire 148, refers to the diameter of every section thereof, including each wire axial portion 152.

According to some embodiments, the diameter of each of the guide member through-holes 130 is dimensioned to accommodate the diameter of the wire 148 extending therethrough. According to some embodiments, the diameter of the guide member through-holes 130 is not greater than 150% of the diameter of the wire 148. According to some embodiments, the diameter of the guide member through-holes 130 is not greater than 120% of the diameter of the wire 148. According to some embodiments, the diameter of the guide member through-holes 130 is not greater than 110% of the diameter of the wire 148. According to some embodiments, the diameter of the guide member through-holes 130 is not greater than 105% of the diameter of the wire 148.

According to some embodiments, the diameter of each of the base member through-holes 140 is dimensioned to accommodate the diameter of the wire 148 extending therethrough. According to some embodiments, the diameter of the base member through-holes 140 is not greater than 150% of the diameter of the wire 148. According to some embodiments, the diameter of the base member through-holes 140 is not greater than 120% of the diameter of the wire 148. According to some embodiments, the diameter of the base member through-holes 140 is not greater than 110% of the diameter of the wire 148. According to some embodiments, the diameter of the base member through-holes 140 is not greater than 105% of the diameter of the wire 148.

Each actuation assembly 40 comprises a sleeve 42 having a sleeve outer surface 46 and a sleeve distal end 44. The sleeve 42 is configured to accommodate a portion of the wire 148 through at least one sleeve channel 50, such that the sleeve 42 and the portion of the wire 148 extending therethrough are axially movable relative to each other. The sleeve 42 extends distally from the handle 30, and terminates at a sleeve distal end 44. Axial movement of the sleeve 42 and the portion of the wire 148 accommodated therein, relative to each other, in a specific direction, is configured to radially expand the frame 106. The sleeve 42 can be, for example, a tube or sheath having sufficient rigidity such that it can apply a distally directed force to the frame 106 or to the guide member 128, without bending or buckling.

The at least one sleeve channel 50 is configured to accommodate a portion of the wire 148 extending into the at least one sleeve channel 50 through at least one sleeve distal opening 48 formed at the sleeve distal end 44. In some embodiments, the at least one channel 50 comprises at least two channels 50a and 50b, each of which configured to accommodate at least a portion of a wire axial portion, such as wire axial portions 152a and 152b, extending into the channels 50a and 50b through sleeve distal opening 48a and 48b, respectively.

The sleeve 42 is dimensioned such that the sleeve distal end 44 can abut or press against the guide member 128, and more specifically, the guide member first surface 134, in a manner that prevents the guide member 128 from sliding or moving in a first direction (e.g., in a proximal direction) beyond the sleeve distal end 44.

FIGS. 5A-5F schematically show an actuation assembly 40$^a$ of a delivery apparatus (12), used in combination with an expansion and locking assembly 126 comprising a wire 148$^a$, according to some applications of the present invention. Actuation assembly 40$^a$ comprises a sleeve 42$^a$ provided with two sleeve channels 50$^a$, wherein each sleeve channel 50$^a$ extends between a sleeve distal opening 48$^a$ defined at the sleeve distal end 44$^a$, and a sleeve side opening 52$^a$ defined at the sleeve outer surface 46$^a$, such that each sleeve side opening 52$^a$ is proximal to the sleeve distal opening 48$^a$, and is substantially orthogonal to the plane of the sleeve distal opening 48$^a$, and/or to the plane of the sleeve distal end 44$^a$.

Each sleeve channel 50$^a$ is configured to guide a corresponding wire axial portion 152$^a$ of a wire 148$^a$, such that each wire axial portion 152$^a$ extends into the corresponding sleeve channel 50$^a$ through the sleeve distal opening 48$^a$, along the path defined by the sleeve channel 50$^a$, and out of the corresponding sleeve side opening 52$^a$. In the configuration shown in FIG. 5A, each wire axial portion 152$^a$ further extends proximally from the sleeve side opening 52, along the sleeve outer surface 46$^a$ and in parallel with the sleeve 42$^a$, potentially all the way toward, and optionally into, the handle 30.

Figure 5A:
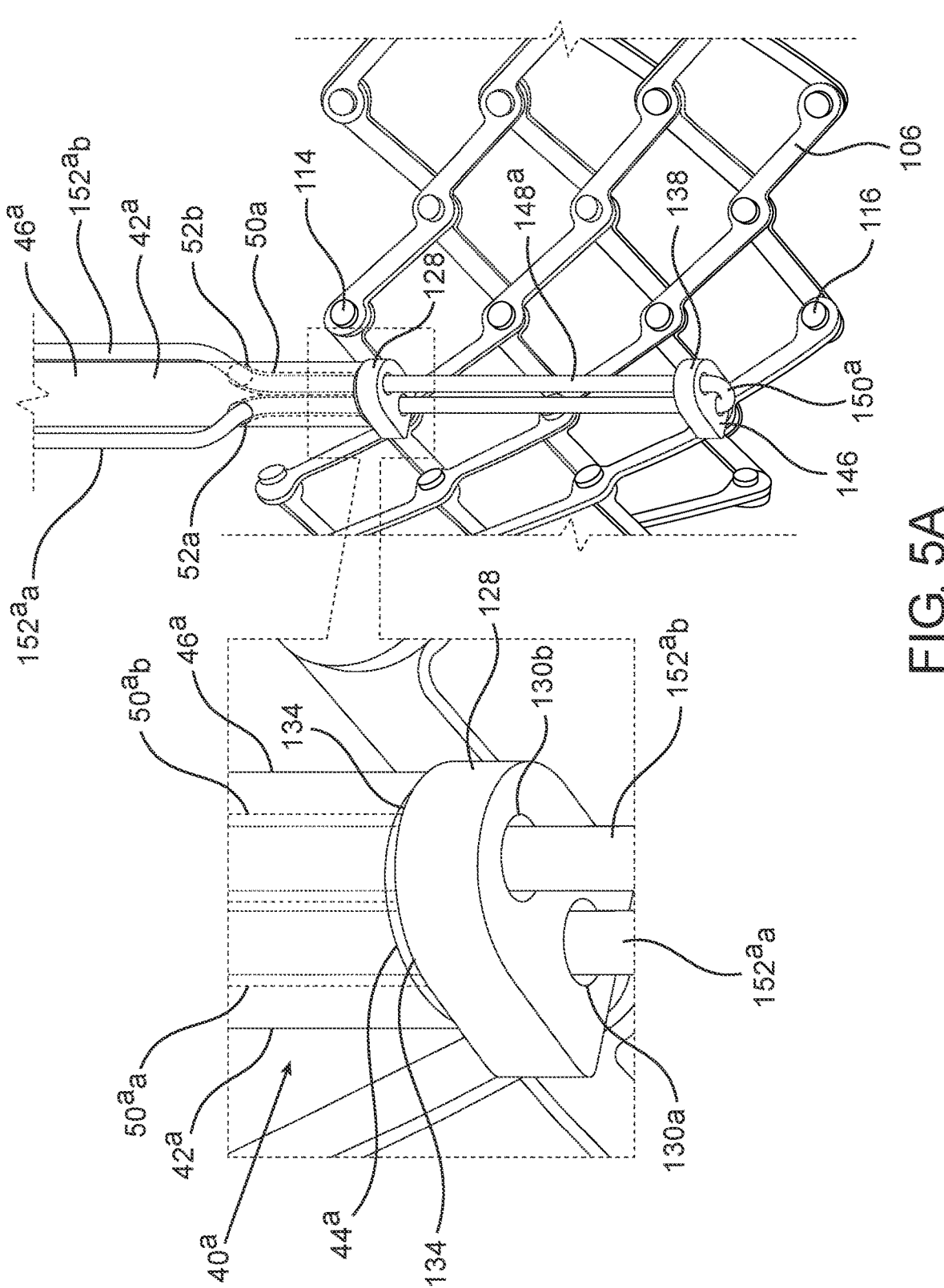

FIG. 5A shows an initial step, in which the prosthetic valve (100) is in a state which is not a fully expanded state of the valve, prior to actuation of the expansion and locking assembly 126 by the actuation assembly 40$^a$. The valve (100) may be delivered to the site of implantation in a compressed or crimped state, such that the state shown in FIG. 5A can be representative of the valve (100) positioned at the desired site of implantation, potentially exposed from an external capsule or an external shaft, such as the delivery shaft 22 or the outer shaft 20, if it was covered by such a capsule or shaft during the delivery to the implantation site via the delivery apparatus 12. The state shown in FIG. 5A can be a crimped or fully compressed state of the valve (100), as well as a partially compressed, or partially expanded, state of the valve (100).

The wire 148$^a$ comprises a wire base end portion 150$^a$ looped over the base member second surface 146 between the base member through-holes 140, wherein both of its wire axial portions 152$^a$ extend proximally from the wire base end portion 150$^a$ through the base member through-holes 140. Specifically, wire axial portion 152$^a$a extends from the wire base end portion 150$^a$, through base member through-hole 140$^a$, toward and into guide member through-hole 130$^a$, into sleeve distal opening 48$^a$a, along sleeve channel 50$^a$a, exiting from sleeve side opening 52$^a$ out of the sleeve

42$^a$, and extending proximally therefrom, adjacent sleeve outer surface 46$^a$. Similarly, wire axial portion 152$^a$b extends from the wire base end portion 150$^a$, through base member through-hole 140$^b$, toward and into guide member through-hole 130$^b$, into sleeve distal opening 48$^a$b, along sleeve channel 50$^a$b, exiting from sleeve side opening 52$^b$ out of the sleeve 42$^a$, and extending proximally therefrom, adjacent sleeve outer surface 46$^a$.

According to some embodiments, the diameter the sleeve channels 50$^a$ is dimensioned to accommodate the diameter of the wire 148$^a$ extending therethrough. According to some embodiments, the diameter of the sleeve channels 50$^a$ is not greater than 150% of the diameter of the wire 148. According to some embodiments, the diameter of the guide sleeve channels 50$^a$ is not greater than 120% of the diameter of the wire 148. According to some embodiments, the diameter of the sleeve channels 50$^a$ is not greater than 110% of the diameter of the wire 148. According to some embodiments, the diameter of the sleeve channels 50$^a$ is not greater than 105% of the diameter of the wire 148.

According to some embodiments, the sleeve 42$^a$ is positioned in the state shown in FIG. 5A in contact with the guide member 128, and more specifically, the sleeve distal end 44$^a$ is in contact, and potentially pressed against, the guide member first surface 134. In some configurations, the valve (100) may be delivered to the site of implantation such that the sleeve distal end 44$^a$ is spaced from the guide member 128. In such configuration, the sleeve 42$^a$ can be advanced, for example, by maneuvering the handle 30, toward the guide member 128, once the valve 100 is positioned at the site of implantation, such that the sleeve distal end 44$^a$ is in contact, and potentially pressed against, the guide member first surface 134.

Figures 5B, 5C:
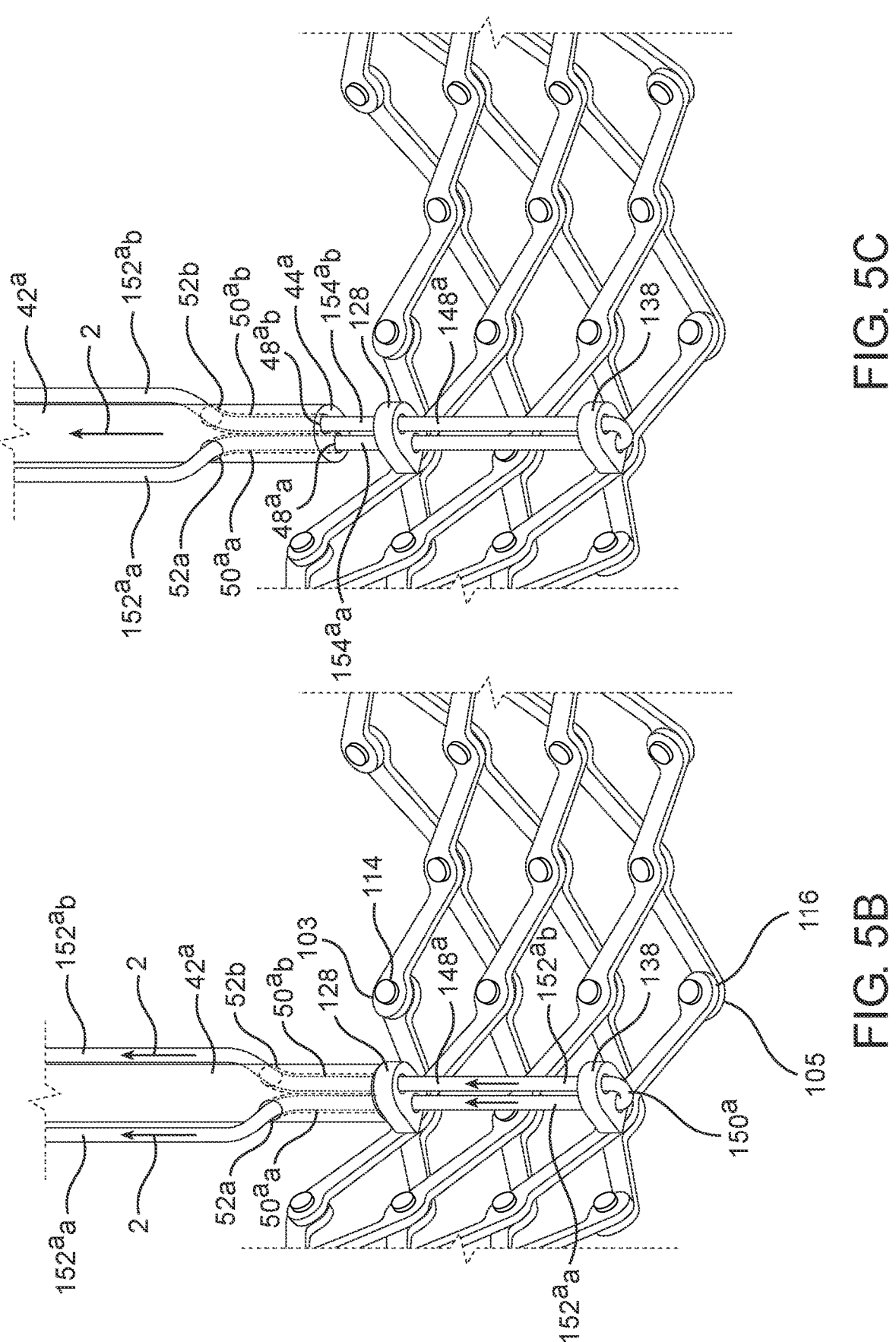

FIG. 5B illustrates a further stage of expanding and locking the prosthetic valve (100), wherein both wire axial portions 152$^a$ are simultaneously pulled in a first direction 2, while the sleeve 42$^a$ is pressed against the guide member 128, and more specifically, while the sleeve distal end 44$^a$ is pressed against the guide member first surface 134, to provide a counter-force against the guide member 128.

When both wire axial portions 152$^a$ are simultaneously pulled in a first direction 2, the wire base end portion 150$^a$, which is pressed against the base member second portion 146, pulls the base member 138 therewith in the same direction. The counter-force provided by the sleeve 42$^a$ against the guide member 128, allows the base member 138 to be pulled toward the guide member 128.

Approximation of the base member 138 and the guide member 128 to each other can be achieved in numerous ways. According to some embodiments, the guide member 128 is held firmly in place by the sleeve 42$^a$, while the pull force applied to the wire axial portions 152$^a$ serves to approximate the base member 138 thereto. According to other embodiments, the force applied to the wire axial portions 152$^a$ serves to apply tension to the wire 148$^a$, which is sufficient to hold the base member 138 firmly in place, while the counter force applied by the sleeve 42$^a$ serves to push the guide member 128 in a second direction 4, toward the base member 138. According to yet other embodiments, the pull force applied to the wire axial portions 152$^a$ in the first direction 2, and the push or counter force applied by the sleeve 42$^a$ in an opposite second direction 4, serve to simultaneously push the guide member 128 in a second direction 4, and pull the base member 138 in a first direction 2, so as to approximate them to each other.

According to some embodiments, the first direction 2 is a proximally oriented direction, and the second direction 4 (shown, for example, in FIG. 5D-5E) is a distally oriented direction.

As the guide member 128 is coupled to the frame 106 at a first location (for example, via guide member fastener 132), and the base member 138 is coupled to the frame 106 at a second location (for example, via base member fastener 142), approximation of the guide member 128 and the base member 138 toward each other, causes the first location and the second location to move toward each other, thereby causing the frame 106 to foreshorten axially and expand radially.

The struts 110 to which the guide member 128 is connected, are free to pivot relative to the guide member fastener 132 and to one another as the frame 106 is expanded or compressed. In this manner, the guide member fastener 132 serves as a coupling means that forms a pivotable connection between those struts 110. Similarly, struts 110 to which the base member 138 is connected, are also free to pivot relative to the base member fastener 142 and to one another as the frame 106 is expanded or compressed. In this manner, the base member fastener 142 also serves as a coupling means that forms a pivotable connection between those struts 110.

FIG. 5C shows a further stage of expanding and locking the prosthetic valve (100), wherein the sleeve 42$^a$ is pulled in a first direction 2 (e.g., the proximal direction), away from the guide member 128, once the valve (100) reaches the desired expansion diameter. As shown, pulling the sleeve 42$^a$ to create a gap between the sleeve distal end 44$^a$ and the guide member first surface 134, exposes portions of the wire axial portions 152$^a$.

In general, the sections of the wire axial portions 152 extending between the guide member first surface 134 and the sleeve distal end 44, when the sleeve 42 is pulled away from the guide member 128 once a desired expansion diameter is reached, are defined as axial lock portions 154. Particularly with reference to FIG. 5C, axial lock portions 154$^a$a and 154$^a$b are shown to extend between the guide member first surface 134 and the sleeve distal end 44$^a$.

According to some embodiments, the sleeve 42$^a$ is pulled in the first direction 2 such that the sleeve distal end 44$^a$ remains distal to, or substantially at the level of, the outflow apices 114. According to some embodiments, the sleeve 42$^a$ is pulled in the first direction 2 such that the sleeve distal end 44$^a$ remains distal to, or substantially at the level of, the outflow end 103.

It is to be noted that at this stage, if the physician is not satisfied with the expansion diameter of the prosthetic valve (100), the sleeve 42$^a$ can be pushed back toward the guide member 128, until the sleeve distal end 44$^a$ contacts the guide member first surface 134, and the frame 106 may be re-expanded further according to any of the methods described above with respect to FIG. 5B.

Figures 5D, 5E:
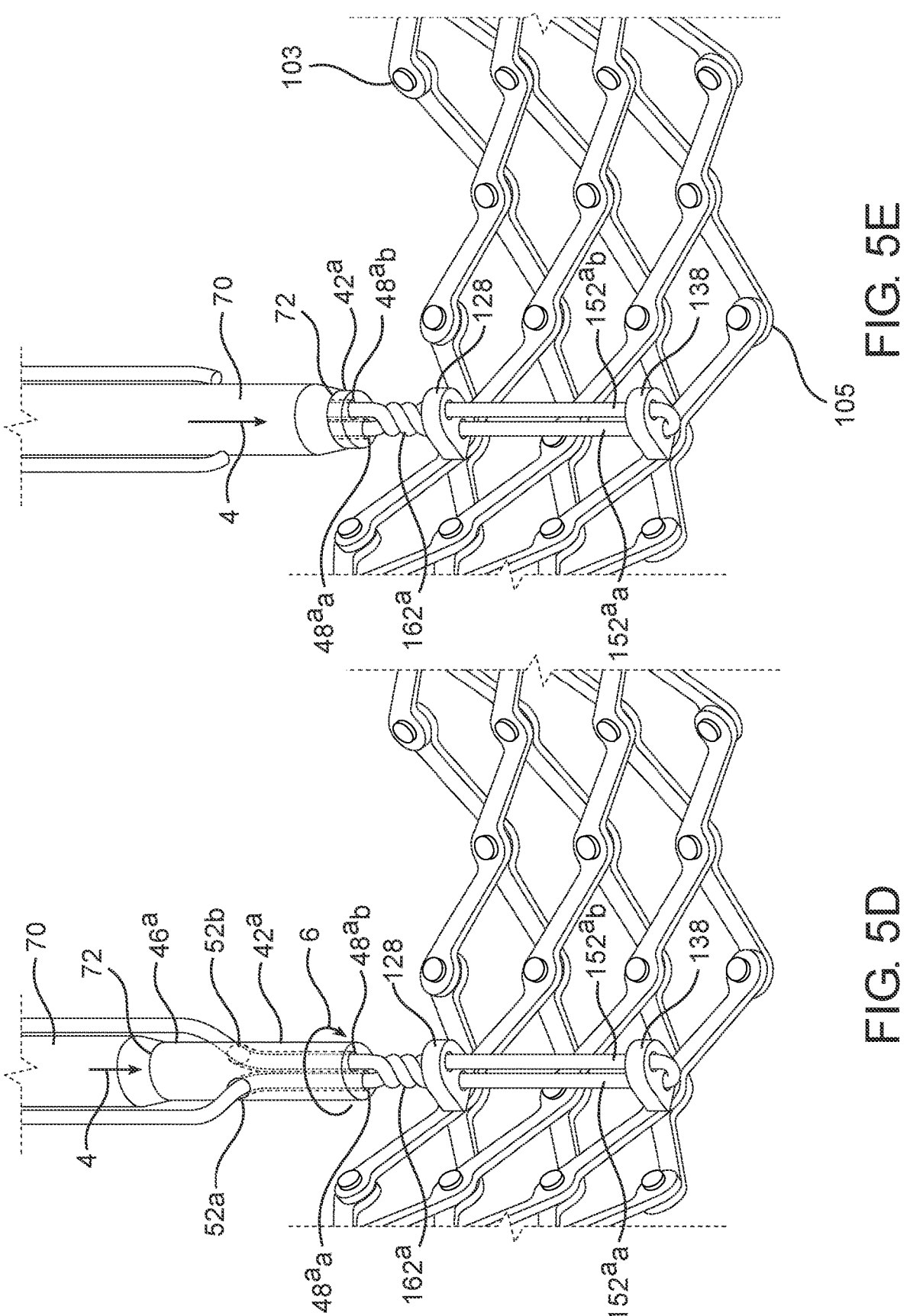

FIG. 5D shows a further stage of expanding and locking the prosthetic valve (100), wherein the sleeve 42$^a$ is rotated around its axis of symmetry, for example in a rotational direction 6 shown in FIG. 5D, such that the axial lock portions 154$^a$a and 154$^a$b are helically intertwined and/or twisted over each other, forming a twist 162$^a$ extending over the guide member first surface 134. In some embodiments, the twist 162$^a$ is proximal to the guide member first surface 134.

According to some embodiments, the actuation assembly 40$^a$ further comprises a cutting shaft 70, extending concentrically over the sleeve 42$^a$ from the handle 30. The cutting shaft 70 is axially movable relative to the sleeve 42$^a$, for example via manipulation of an appropriate knob 32 of the handle 30. The cutting shaft 70 comprises a blade 72 at its distal end, equipped with a sharp edge, extending over the sleeve outer surface 46.

The cutting shaft 70 is positioned such that prior to forming the twist 162$^a$, its blade 72 is distanced away from the sleeve side openings 52. For example, the cutting shaft 70 is positioned such that prior to forming the twist 162$^a$, its blade 72 is positioned proximal to the sleeve side openings 52.

As further shown in FIG. 5D, once the twist 162$^a$ is formed, the cutting shaft 70 is slid in a second direction 4 (e.g., the distal direction), toward the sleeve side openings 52. According to some embodiments, the blade 72 is sharp enough to cut the wire 148$^a$. In such embodiments, once the blade 72 slides over the sleeve side openings 52, it cuts the wire axial portions 152$^a$ extending therefrom, as illustrated in the subsequent stage shown in FIG. 5E.

Figure 5F:
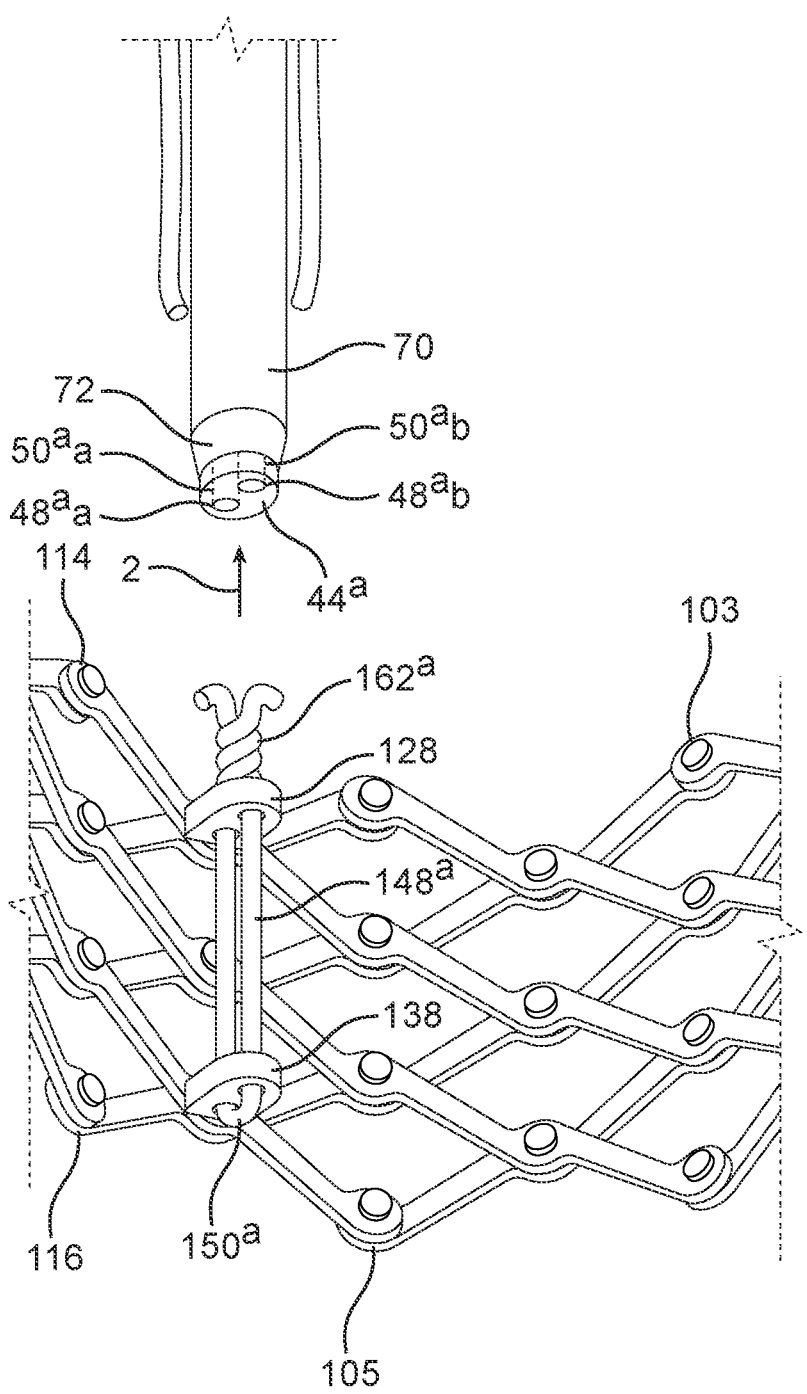

FIG. 5F shows a final stage of expanding and locking the prosthetic valve (100), wherein the actuation assembly 40$^a$ is pulled in the first direction (e.g., the proximal direction), along with the cut-off sections of the wire axial portions 152$^a$, allowing the excess portions of the wire axial portions 152$^a$ that remained within the sleeve 42$^a$ to slide out of the respective sleeve channels 50$^a$, while the delivery apparatus 12 may be retrieved from the patient's body, leaving the prosthetic valve (100) implanted in the patient.

The plastic deformation of the wire 148$^a$, and specifically that of the axial lock portions 154$^a$, prevents them from unwinding, such that the axial lock portions 154$^a$a and 154$^a$b remain intertwined with each other, together forming the twist 162$^a$, even once the wire 148$^a$ is cut of and released from the actuation assembly 40$^a$.

In this final expanded state, the wire axial portions 152$^a$a and 152$^a$a are tensioned between the guide member 128 and the base member 138, wherein the wire base end portion 150$^a$ disposed over the base member second surface 146, and the twist 162$^a$ disposed the guide member first surface 134, prevent the guide member 128 and the base member 138 from being distanced away from each other, effectively locking the frame 106 in the expanded diameter.

The patient's native anatomy, such as the native aortic annulus in the case of transcatheter aortic valve implantation, may exert radial forces against the prosthetic valve (100) that would strive to compress it. However, twist 162$^a$, formed over the guide member first surface 134, serves as a locking feature preventing such forces from compressing the frame 106, thereby ensuring that the frame 106 remains locked in the desired radially expanded state.

According to some embodiments, the length of the remaining twist 162$^a$ does not extend beyond, or proximal to, the outflow apices 114. According to some embodiments, the length of the remaining twist 162$^a$ does not extend beyond, or proximal to, the outflow end 103.

According to some embodiments, each actuation assembly 40$^a$ further comprises an overtube (not shown), concentric with the sleeve 42$^a$ and disposed external to the sleeve 42$^a$, the cutting shaft 70, and the sections of the wire axial portions 152$^a$ extending parallel to the sleeve 42$^a$, external to the sleeve outer surface 46$^a$.

According to some embodiments, there is provided a method of expanding and locking a prosthetic valve (100), comprising a step of providing a delivery assembly (10) that includes a prosthetic valve (100) equipped with at least one, and preferably a plurality of expansion and locking assemblies 126 that include a guide member 128 attached to the frame 106 at a first location, a base member 138 attached to the frame 106 at a second location axially spaced from the first location, and a wire 148$^a$ comprising two wire axial portions 152$^a$ extending from a wire base end portion 150$^a$ looped over a base member second surface 146, through base member through-holes 140, toward and through guide member through-holes 130.

The delivery assembly (10) also includes a delivery apparatus (12) equipped with at least one, and preferably a plurality of actuation assemblies 40$^a$, wherein each actuation assembly 40$^a$ includes sleeve 42$^a$ having two sleeve channels 50$^a$, such that the wire axial portions 152$^a$ extend from the guide member 128, through sleeve distal openings 48$^a$, along the sleeve channels 50$^a$, and out of the sleeve 42$^a$ through sleeve side openings 52.

According to some embodiments, the method further comprises a step of approximating the sleeve 42$^a$ to the guide member 128, such that they may, for example, contact each other.

According to some embodiments, the method further comprises a step of utilizing the actuation assembly 40$^a$ and the wire 148$^a$ to expand the frame (106) by approximating the guide member 128 and the base member 138 to each other.

According to some embodiments, the step of utilizing the actuation assembly 40$^a$ and the wire 148$^a$ to expand the frame (106) includes simultaneously applying a pull force in a first direction 2 on both wire axial portions 152$^a$, so as to pull the base member 138 in the first direction 2, while the sleeve 42$^a$ is pressed against the guide member 128, applying a counterforce thereto, so as to hold the guide member 128 in place.

According to some embodiments, the step of utilizing the actuation assembly 40$^a$ and the wire 148$^a$ to expand the frame (106) includes applying a push force in a second direction 4 by the sleeve 42$^a$, so as to push the guide member 128 in a second direction 4, while the wire 148$^a$ applies a counter force, via its wire base end portion 150$^a$, against the base member 138, so as to hold the base member 138 in place.

According to some embodiments, the step of utilizing the actuation assembly 40$^a$ and the wire 148$^a$ to expand the frame (106) includes simultaneously applying a pull force in a first direction 2 on both wire axial portions 152$^a$, so as to pull the base member 138 in the first direction 2, while applying a push force in a second direction 4 by the sleeve 42$^a$, so as to push the guide member 128 in a second direction 4.

According to some embodiments, the method further comprises a step of pulling the sleeve 42 away from the guide member 128, thereby exposing the axial lock portions 154$^a$ of the wire 148$^a$.

According to some embodiments, the method further comprises a step of rotating the sleeve 42 around its axis of symmetry, so as to intertwine both axial lock portions 154$^a$ over each other, forming a twist disposed over the guide member 128.

According to some embodiments, the method further comprises a step of sliding a cutting shaft 70 equipped with a blade 72 in a second direction 4 toward and over the sleeve side openings 52, thereby cutting the sections of the axial lock portions 154$^a$ exiting the sleeve 42$^a$ out of the sleeve side openings 52.

According to some embodiments, the method further comprises a step of retrieving the delivery apparatus (12), including the actuation assemblies 40$^a$, away from the prosthetic valve (100), thereby allowing the slacks of the wire axial portions 152$^a$ that remained within the sleeve 42$^a$ to slide out of the sleeve channels 50$^a$.

According to some embodiments, the step of retrieving the delivery apparatus (12) also includes retrieving the proximal cut-off sections of the wire axial portions 152$^a$.

The terms coupled, engaged, connected and attached, as used herein, are interchangeable. Similarly, the term decoupled, disengaged, disconnected and detached, as used herein, are interchangeable.

According to some embodiments, the handle 30 can comprise control mechanisms which may include steerable or rotatable knobs 32, levers, buttons and such, which in some implementation may be manually controllable by an operator to produce axial and/or rotatable movement of different components of the delivery apparatus 12, as well as the wire 148. For example, the embodiment of handle 30 illustrated in FIG. 1 comprises first, second, third and fourth knobs 32$a$. 32$b$. 32$c$ and 32$d$, respectively.

According to some embodiments, knob 32$a$ can be a rotatable or otherwise operable knob configured to produce radial expansion. For example, rotation of the knob 32$d$ can pull both wire axial portions 152$^a$ while keeping the sleeve 42$^a$ stationary in position. Alternatively, knob 32$a$ can be configured to push the sleeve 42$^a$ while keeping the wire axial portions 152$^a$ tensioned stationary in position. In another alternative, knob 32$a$ can be configured to push the sleeve 42$^a$ while both wire axial portions 152$^a$ are also pulled.

According to some embodiments, knob 32$b$ can be configured to pull the sleeve 42$^a$ in a first direction 2, for example—to space it away from the guide member 128.

According to some embodiments, knob 32$c$ can be a rotatable or otherwise operable knob configured to rotate the sleeve 42$^a$ around its axis of symmetry, so as to facilitate formation of a twist 162$^a$ by intertwining the axial lock portions 154$^a$ over each other.

According to some embodiments, knob 32$d$ can be configured to advance a cutting shaft 70) in a second direction 4, toward and over side openings 52 of the sleeve 42$^a$, so as to cut the wire axial portions 152$^a$ extending therefrom.

The handle 30 may include more or less than the four knobs 32 described herein above, configured to fulfill only some of the functionalities described for knobs 32$a$. 32$b$. 32$c$ and 32$d$, and/or additional functionalities. Any of the knobs 32$a$. 32$b$. 32$c$ and 32$d$ may be implemented, in alternative embodiments, as other types of buttons, levers, knobs and the like, such as push/pull knobs which may be actuated by sliding or moving the knobs axially.

According to other embodiments, control mechanisms in the handle 30 and/or other components of the delivery apparatus 12 can be electrically, pneumatically and/or hydraulically controlled. According to some embodiments, the handle 30 can house one or more electric motors which can be actuated by an operator, such as by pressing a button or a switch on the handle 30, to produce movement of components of the delivery apparatus 12. For example, the handle 30 may include one or more motors operable to produce linear movement of components of the actuation assemblies 40$^a$ and/or wires 148$^a$. According to some embodiments, one or more manual or electric control mechanism is configured to produce simultaneous linear and/or rotational movement of all of the wires 148$^a$, the sleeves 42$^a$, and/or the cutting shafts 70.

FIGS. 6A-6F schematically show an actuation assembly 40$^a$ of a delivery apparatus (12), used in combination with an expansion and locking assembly 126 comprising a wire 148$^b$, according to some applications of the present invention. Actuation assembly 40$^a$ shown in FIGS. 6A-6F may be identical to that shown and described above with respect to FIGS. 5A-5F, and may be implemented according to any of the embodiments described for actuation assembly 40$^a$ hereinabove.

Specifically, actuation assembly 40$^a$ comprises a sleeve 42$^a$ provided with two sleeve channels 50$^a$, wherein each sleeve channel 50$^a$ extends between a sleeve distal opening 48$^a$ defined at the sleeve distal end 44$^a$, and a sleeve side opening 52$^a$ defined at the sleeve outer surface 46$^a$, such that each sleeve side opening 52$^a$ is proximal to the sleeve distal opening 48$^a$, and is substantially orthogonal to the plane of the sleeve distal opening 48$^a$, and/or to the plane of the sleeve distal end 44$^a$.

According to some embodiments, actuation assembly 40$^a$ further comprises a couple of pull members 54$^a$, extending from the handle 30 and coupled to the wire axial portions 152$^b$. The wire 148$^b$ is similar to wire 148$^a$ described above with respect to FIGS. 5A-5F, except that the wire axial portions 152$^b$ do not extend proximally all the way to the handle 30, but are rather coupled, for example at their proximal ends, to respective pull members 54$^a$.

Each sleeve channel 50$^a$ is configured to guide a corresponding portion of a wire axial portion 152$^b$ and a corresponding portion of a pull member 54$^a$ attached thereto, such that each wire axial portion 152$^b$ extends into the corresponding sleeve channel 50$^a$ through the sleeve distal opening 48$^a$, partially following the path defined by the sleeve channel 50$^a$, wherein it may terminate within the sleeve channel 50$^a$, having its end (e.g., its proximal end) attached to a respective pull member 54$^a$, which in turn continues to follow the path defined by the sleeve channel 50$^a$ so as to exit out of the corresponding sleeve side opening 52$^a$. In the configuration shown in FIG. 5A, each pull member 54$^a$ further extends proximally from the sleeve side opening 52, along the sleeve outer surface 46$^a$ and in parallel with the sleeve 42$^a$, potentially all the way toward, and optionally into, the handle 30.

Figure 6A:
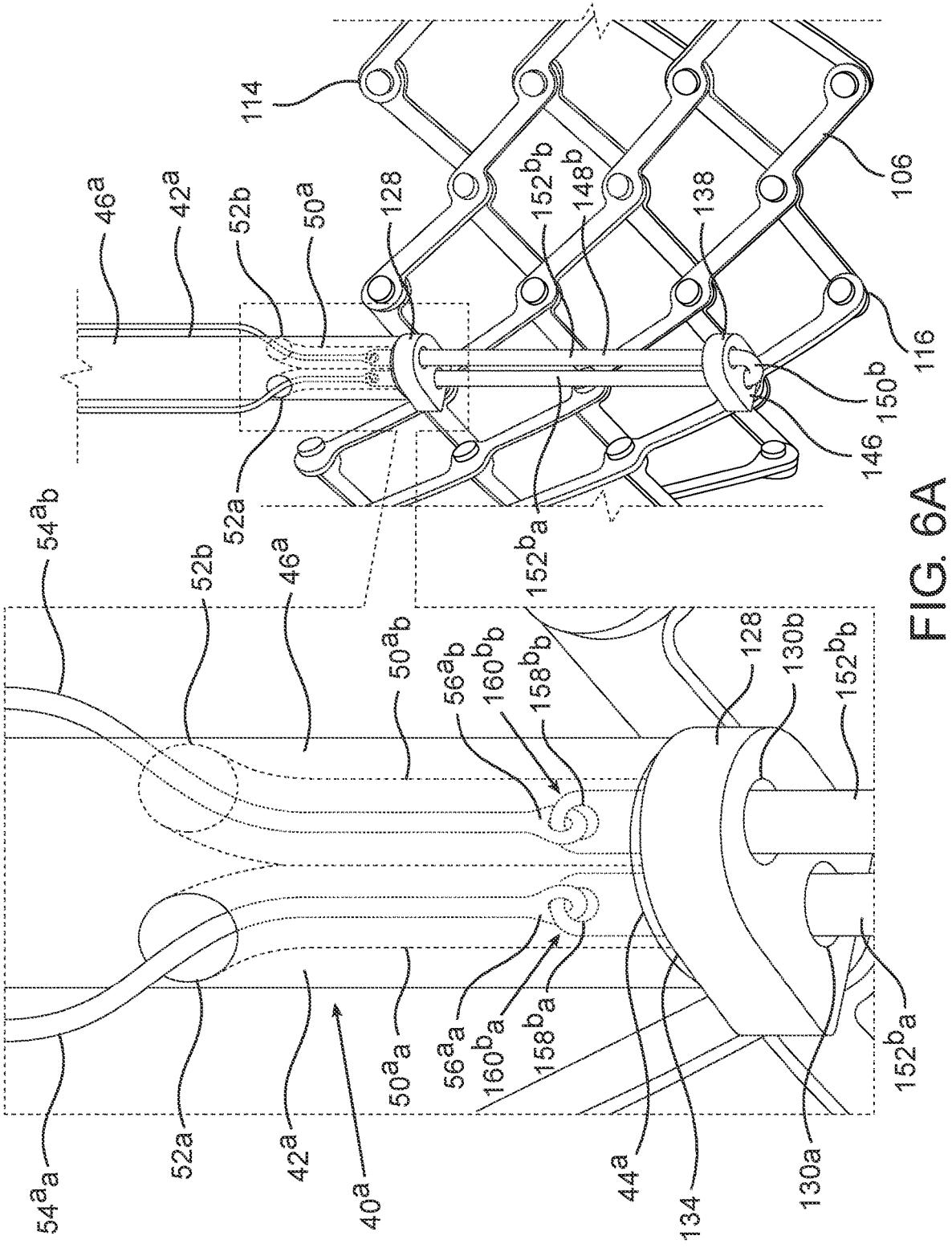

According to some embodiments, each wire axial portion 152$^b$ comprises an attachment interface 160$^b$, for attachment to a distal end of a corresponding pull member 54$^a$. According to some embodiments, the attachment interface 160$^b$ comprises a loop or an eyelet 158$^b$, as shown in FIG. 6A. The pull member 54$^a$ can include a similar eyelet or a pull member loop 56$^a$, configured to interface and attach with the eyelet 158$^b$.

While the attachment between the ends of the wire axial portions 152$^b$ and the pull member 54$^a$ is shown in the form of loops and/or eyelets, it is to be understood that they may be attached to each other by any other attachment means known in the art, including: stitching, welding, gluing, tying and the like.

Unlike the wire 148$^b$, which is made of a plastically deformable material, the pull members 54$^a$ can be made of soft flexible materials, and may include: non-metallic wires, strings, cables, ropes, sutures, and the like.

FIG. 6A shows an initial step, in which the prosthetic valve (100) is in a state which is not a fully expanded state of the valve, prior to actuation of the expansion and locking assembly 126 by the actuation assembly 40$^a$. The valve (100) may be delivered to the site of implantation in a compressed or crimped state, such that the state shown in FIG. 6A can be representative of the valve (100) positioned at the desired site of implantation, potentially exposed from an external capsule or an external shaft, such as the delivery shaft 22 or the outer shaft 20, if it was covered by such a capsule or shaft during the delivery to the implantation site via the delivery apparatus 12. The state shown in FIG. 6A can be a crimped or fully compressed state of the valve (100), as well as a partially compressed, or partially expanded, state of the valve (100).

The wire 148$^b$ comprises a wire base end portion 150$^b$ looped over the base member second surface 146 between the base member through-holes 140, wherein both of its wire axial portions 152$^b$ extend proximally from the wire base end portion 150$^b$ through the base member through-holes 140. Specifically, wire axial portion 152$^b$a extends from the wire base end portion 150$^b$, through base member through-hole 140$^a$, toward and into guide member through-hole 130$^a$, and into sleeve distal opening 48$^a$a, partially along sleeve channel 50$^a$a. The wire axial portion 152$^b$ terminates within the sleeve channel 50$^a$a with an interface 160$^b$a in the form of an eyelet 158$^b$a, which is coupled to a pull member loop 56$^a$a of a pull member 54$^a$a. The pull member 54$^a$a extends therefrom along the remainder of the sleeve channel 50$^a$a, exiting from sleeve side opening 52$^a$ out of the sleeve 42$^a$, and extends proximally therefrom, adjacent sleeve outer surface 46$^a$.

Similarly, wire axial portion 152$^b$b extends from the wire base end portion 150$^b$, through base member through-hole 140$^b$, toward and into guide member through-hole 130$^b$, and into sleeve distal opening 48$^a$b, partially along sleeve channel 50$^a$b. The wire axial portion 152$^b$ terminates within the sleeve channel 50$^a$b with an attachment interface 160$^b$b in the form of an eyelet 158$^b$b, which is coupled to a pull member loop 56$^a$b of a pull member 54$^a$b. The pull member 54$^a$b extends therefrom along the remainder of the sleeve channel 50$^a$b, exiting from sleeve side opening 52$^b$ out of the sleeve 42$^a$, and extends proximally therefrom, adjacent sleeve outer surface 46$^a$.

According to some embodiments, the diameter the sleeve channels 50$^a$ is dimensioned to accommodate the diameter of the wire 148$^b$ as well as that of the pull member 54$^a$ extending therethrough. The diameter of the pull members 54$^a$ can be similar or different than that of the wire 148$^b$. While the pull members 54$^a$ are illustrated to be thinner than the wire in FIG. 6A, it is to be understood that this is shown for illustrative purpose only, and that in alternative embodiments, the pull members 54$^a$ can have the same diameter as that of the wire 148$^b$, or may be thicker than the wire 148$^b$.

According to some embodiments, the diameter of the sleeve channels 50$^a$ is not greater than 150% of the diameter of the pull members 54$^a$. According to some embodiments, the diameter of the guide sleeve channels 50$^a$ is not greater than 120% of the diameter of the pull members 54$^a$. According to some embodiments, the diameter of the sleeve channels 50$^a$ is not greater than 110% of the diameter of the pull members 54$^a$. According to some embodiments, the diameter of the sleeve channels 50$^a$ is not greater than 105% of the diameter of the pull members 54$^a$.

According to some embodiments, the attachment interface 160$^b$ connecting the wire axial portion 152$^b$ with the pull member 54$^a$ can be wider (at its widest dimension) than either one of the wire axial portion 152$^b$ or the pull member 54$^a$. In such embodiments, the diameter the sleeve channels 50$^a$ is dimensioned to accommodate the attachment interface 160$^b$.

According to some embodiments, the diameter of the sleeve channels 50$^a$ is not greater than 150% of the width of the attachment interface 160$^b$. According to some embodiments, the diameter of the guide sleeve channels 50$^a$ is not greater than 120% of the width of the attachment interface 160$^b$. According to some embodiments, the diameter of the sleeve channels 50$^a$ is not greater than 110% of the width of the attachment interface $160^b$. According to some embodiments, the diameter of the sleeve channels $50^a$ is not greater than 105% of the width of the attachment interface $160^b$.

According to some embodiments, the sleeve $42^a$ is positioned in the state shown in FIG. 6A in contact with the guide member 128, and more specifically, the sleeve distal end $44^a$ is in contact, and potentially pressed against, the guide member first surface 134. In some configurations, the valve (100) may be delivered to the site of implantation such that the sleeve distal end $44^a$ is spaced from the guide member 128. In such configuration, the sleeve $42^a$ can be advanced, for example, by maneuvering the handle 30, toward the guide member 128, once the valve 100 is positioned at the site of implantation, such that the sleeve distal end $44^a$ is in contact, and potentially pressed against, the guide member first surface 134.

Figures 6B, 6C:
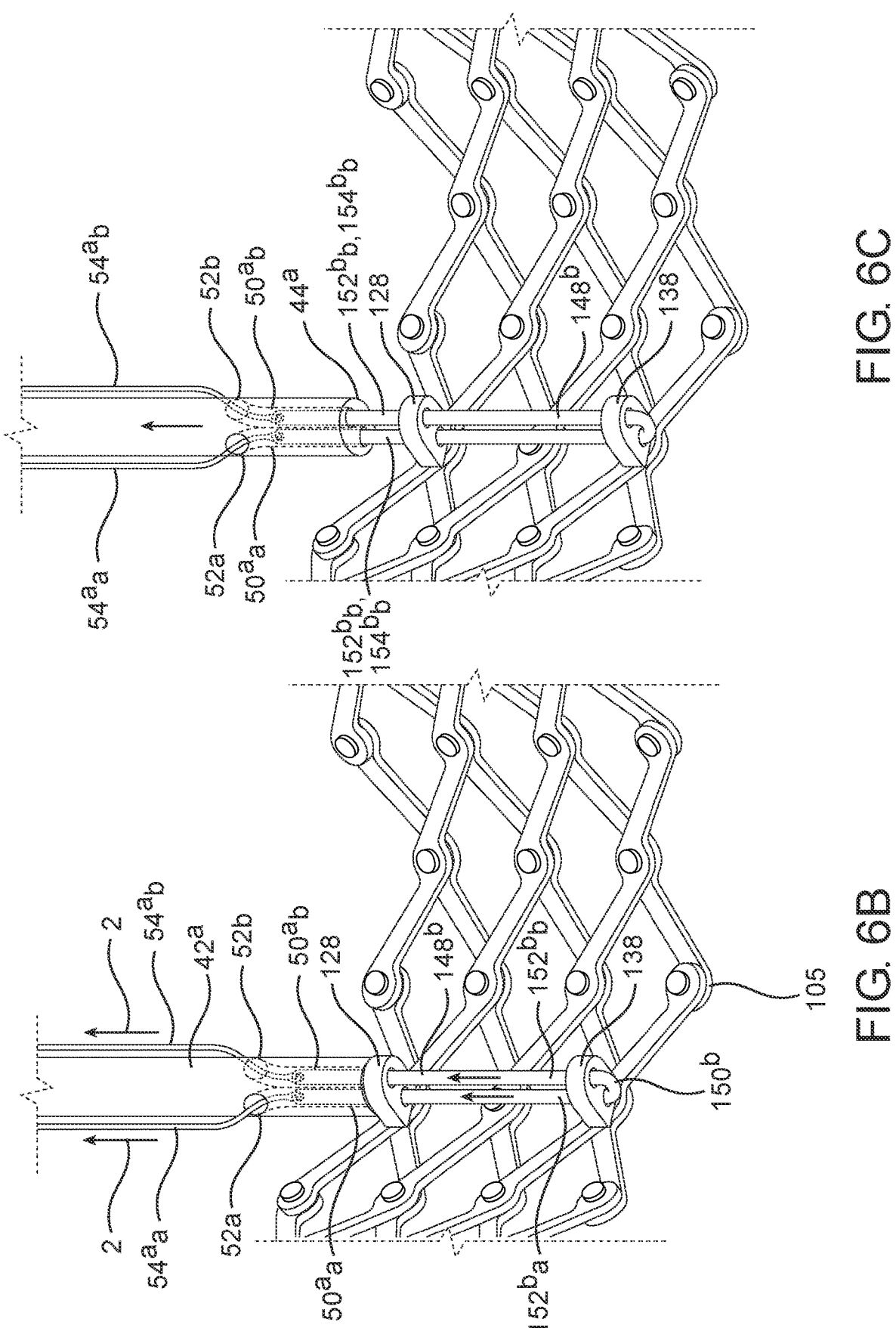

FIG. 6B illustrates a further stage of expanding and locking the prosthetic valve (100), wherein both pull members $54^a$ are simultaneously pulled in a first direction 2, pulling both wire axial portions $152^b$ there-along, while the sleeve $42^a$ is pressed against the guide member 128, and more specifically, while the sleeve distal end $44^a$ is pressed against the guide member first surface 134, to provide a counter-force against the guide member 128.

When both pull members $54^a$, along with the wire axial portions $152^b$ attached thereto, are simultaneously pulled in a first direction 2, the wire base end portion $150b$, which is pressed against the base member second portion 146, pulls the base member 138 therewith in the same direction. The counter-force provided by the sleeve $42^a$ against the guide member 128, allows the base member 138 to be pulled toward the guide member 128.

Approximation of the base member 138 and the guide member 128 to each other can be achieved in numerous ways. According to some embodiments, the guide member 128 is held firmly in place by the sleeve $42^a$, while the pull force applied to the pull members $54^a$, which in turn is applied to the wire axial portions $152^b$, serves to approximate the base member 138 thereto. According to other embodiments, the force applied to the pull members $54^a$, and hence, to the wire axial portions $152^b$, serves to apply tension to the wire $148^b$, which is sufficient to hold the base member 138 firmly in place, while the counter force applied by the sleeve $42^a$ serves to push the guide member 128 in a second direction 4, toward the base member 138. According to yet other embodiments, the pull force applied to the pull members $54^a$, and hence, to the wire axial portions $152^b$, in the first direction 2, and the push or counter force applied by the sleeve $42^a$ in an opposite second direction 4, serve to simultaneously push the guide member 128 in a second direction 4, and pull the base member 138 in a first direction 2, so as to approximate them to each other.

As the guide member 128 is coupled to the frame 106 at a first location (for example, via guide member fastener 132), and the base member 138 is coupled to the frame 106 at a second location (for example, via base member fastener 142), approximation of the guide member 128 and the base member 138 toward each other, causes the first location and the second location to move toward each other, thereby causing the frame 106 to foreshorten axially and expand radially.

FIG. 6C shows a further stage of expanding and locking the prosthetic valve (100), wherein the sleeve $42^a$ is pulled in a first direction 2 (e.g., the proximal direction), away from pulling the sleeve $42^a$ to create a gap between the sleeve distal end $44^a$ and the guide member first surface 134, exposes axial lock portions $154^b$a and $154^b$b, which extend between the guide member first surface 134 and the sleeve distal end $44^a$.

According to some embodiments, the sleeve $42^a$ is pulled in the first direction 2 such that the sleeve distal end $44^a$ remains distal to, or substantially at the level of, the outflow apices 114. According to some embodiments, the sleeve $42^a$ is pulled in the first direction 2 such that the sleeve distal end $44^a$ remains distal to, or substantially at the level of, the outflow end 103. According to some embodiments, as further shown in FIG. 6C, the sleeve $42^a$ is pulled away from the guide member 128 to such a distance, that the attachment interfaces $160^b$ remain in the corresponding sleeve channels $50^a$.

It is to be noted that at this stage, if the physician is not satisfied with the expansion diameter of the prosthetic valve (100), the sleeve $42^a$ can be pushed back toward the guide member 128, until the sleeve distal end $44^a$ contacts the guide member first surface 134, and the frame 106 may be re-expanded further according to any of the methods described above with respect to FIG. 6B.

Figures 6D, 6E:
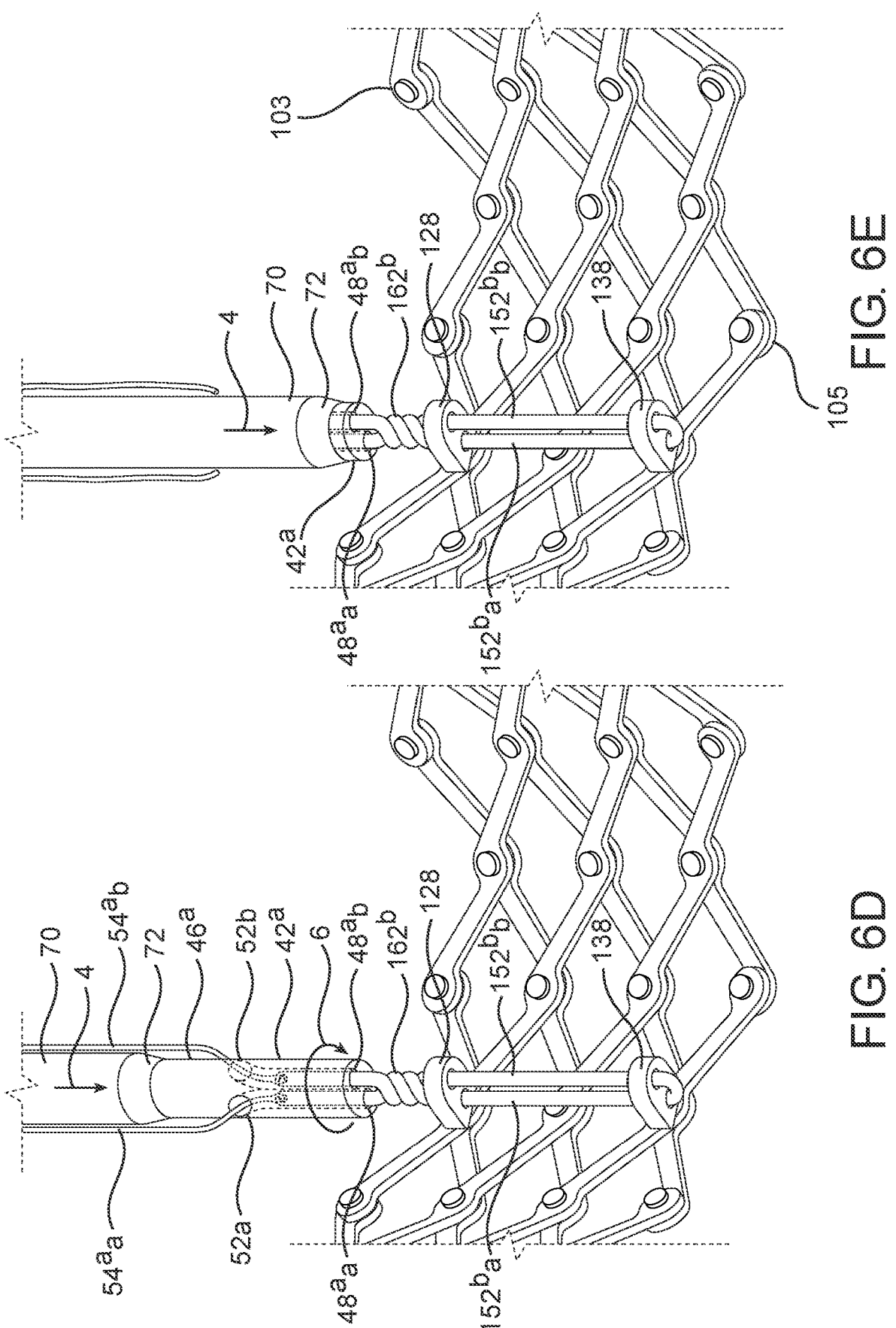

FIG. 6D shows a further stage of expanding and locking the prosthetic valve (100), wherein the sleeve $42^a$ is rotated around its axis of symmetry, for example in a rotational direction 6 shown in FIG. 6D, such that the axial lock portions $154^b$a and $154^b$b are helically intertwined and/or twisted over each other, forming a twist $162^b$ extending over the guide member first surface 134. In some embodiments, the twist $162^b$ is proximal to the guide member first surface 134.

As mentioned above, the attachment interfaces $160^b$ preferably remain within the corresponding sleeve channels $50^a$, such that rotation of the sleeve $42^a$ will effectively force the axial lock portions $154^b$ to twist over each other. If the sleeve $42^a$ is pulled further prior to such rotation, in a manner that the attachment interfaces $160^b$ would have been out of (e.g., distal to) the sleeve channels $50^a$, rotation of the sleeve $42^a$ would have twisted the softer pull members $54^a$, which could reversibly intertwine with each other instead of translating the rotational movement to the axial lock portions $154^b$, thereby failing to form the twist $162^b$.

According to some embodiments, the actuation assembly $40^a$ further comprises the cutting shaft 70, which may be identical to the cutting shaft 70 described herein above with respect to FIGS. 5D-5E, and extends concentrically over the sleeve $42^a$ from the handle 30. The cutting shaft 70 comprises a blade 72 at its distal end, equipped with a sharp edge, extending over the sleeve outer surface 46.

The cutting shaft 70 is positioned such that prior to forming the twist $162^b$, its blade 72 is distanced away from the sleeve side openings 52. For example, the cutting shaft 70 is positioned such that prior to forming the twist $162^b$, its blade 72 is positioned proximal to the sleeve side openings 52.

As further shown in FIG. 6D, once the twist $162^b$ is formed, the cutting shaft 70 is slid in a second direction 4 (e.g., the distal direction), toward the sleeve side openings 52. According to some embodiments, the blade 72 is sharp enough to cut the pull members $54^a$. In such embodiments, once the blade 72 slides over the sleeve side openings 52, it cuts the pull members $54^a$ extending therefrom, as illustrated in the subsequent stage shown in FIG. 6E.

Figure 6F:
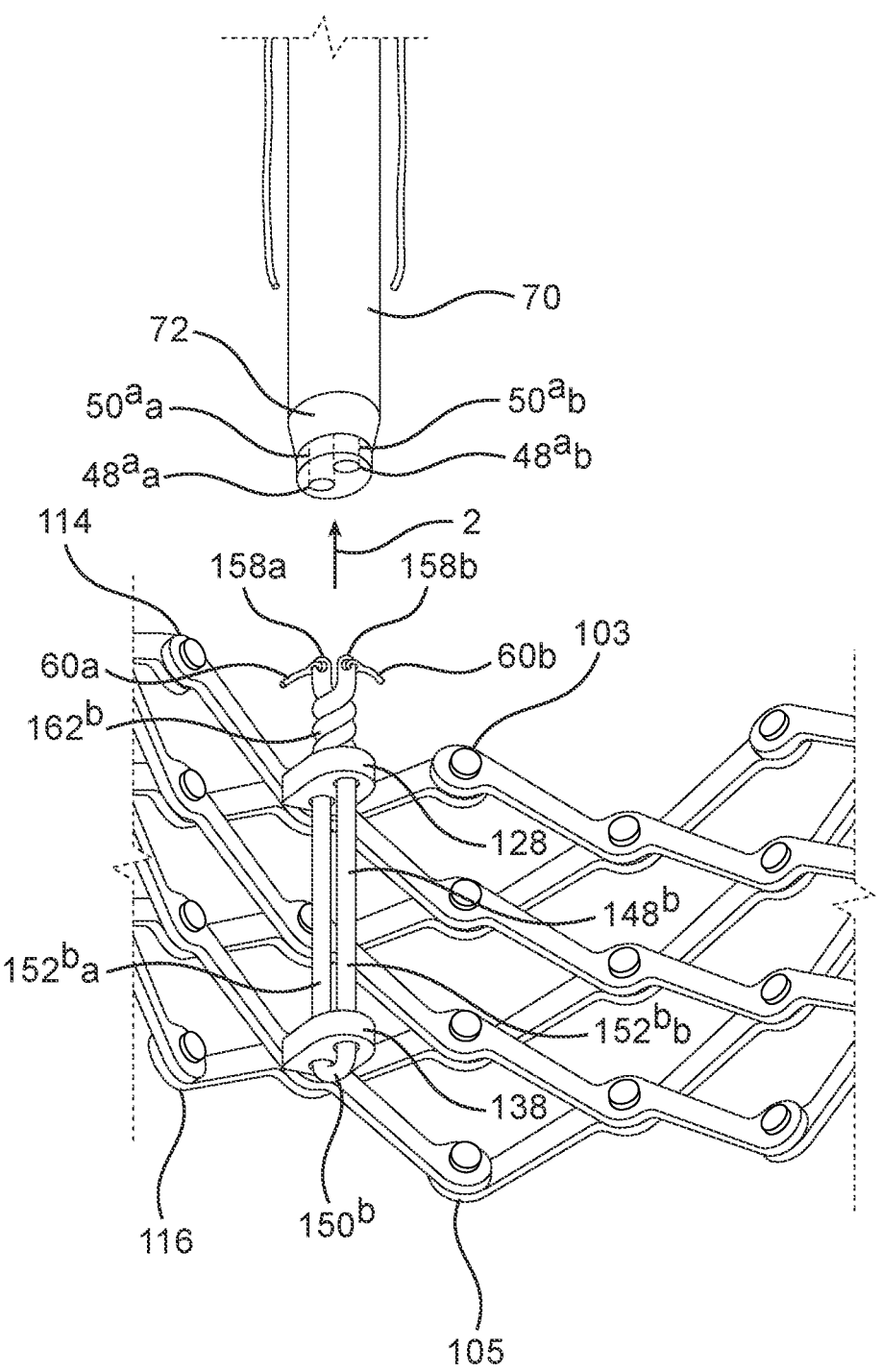

FIG. 6F shows a final stage of expanding and locking the prosthetic valve (100), wherein the actuation assembly $40^a$ is pulled in the first direction (e.g., the proximal direction), along with the cut-off sections of the pull members $54^a$, allowing the portions of the wire axial portions $152^a$ and the slacks 60 of the pull members 54$^a$ that remained within the sleeve 42$^a$ to slide out of the respective sleeve channels 50$^a$, while the delivery apparatus 12 may be retrieved from the patient's body, leaving the prosthetic valve (100) implanted in the patient.

The plastic deformation of the wire 148$^b$, and specifically that of the axial lock portions 154$^b$, prevents them from unwinding, such that the axial lock portions 154$^b$a and 154$^b$b remain intertwined with each other, together forming the twist 162$^b$, even once the pull members 54$^a$ are cut and the wire 148$^b$ is released from the actuation assembly 40$^a$.

In this final expanded state, the wire axial portions 152$^b$a and 152$^b$a are tensioned between the guide member 128 and the base member 138, wherein the wire base end portion 150$^b$ disposed over the base member second surface 146, and the twist 162$^b$ disposed the guide member first surface 134, prevent the guide member 128 and the base member 138 from being distanced away from each other, effectively locking the frame 106 in the expanded diameter.

The patient's native anatomy, such as the native aortic annulus in the case of transcatheter aortic valve implantation, may exert radial forces against the prosthetic valve (100) that would strive to compress it. However, twist 162$^b$, formed over the guide member first surface 134, serves as a locking feature preventing such forces from compressing the frame 106, thereby ensuring that the frame 106 remains locked in the desired radially expanded state.

According to some embodiments, the attachment interfaces 160$^b$ at the end of the twist 162$^b$ do not extend beyond, or proximal to, the outflow apices 114. According to some embodiments, the attachment interfaces 160$^b$ at the end of the twist 162$^b$ do not extend beyond, or proximal to, the outflow end 103.

The configuration described hereinabove with respect to FIGS. 6A-6F, may be advantageous over the configuration described with respect to FIGS. 5A-5F, as it may be easier for the blade 72 of a cutting shaft 70 to cut soft and flexible pull members 54$^a$, which can be in the form of strings or sutures, than cutting a stiffer wire 148, which can include metallic wires. Moreover, cutting soft and flexible pull members 54$^a$ may result in favorable atraumatic end portions of the slacks 60, while cutting stiffer wires 148 may result in undesirably sharp ends.

According to some embodiments, each actuation assembly 40$^a$ further comprises an overtube (not shown), concentric with the sleeve 42$^a$ and disposed external to the sleeve 42$^a$, the cutting shaft 70, and the sections of the pull members 54$^a$ extending parallel to the sleeve 42$^a$, external to the sleeve outer surface 46$^a$.

According to some embodiments, there is provided a method of expanding and locking a prosthetic valve (100), comprising a step of providing a delivery assembly (10) that includes a prosthetic valve (100) equipped with a plurality of expansion and locking assemblies 126 that include a guide member 128 attached to the frame 106 at a first location, a base member 138 attached to the frame 106 at a second location axially spaced from the first location, and a wire 148$^b$ comprising two wire axial portions 152$^b$ extending from a wire base end portion 150$^b$ looped over a base member second surface 146, through base member through-holes 140, toward and through guide member through-holes 130.

The delivery assembly (10) also includes a delivery apparatus (12) equipped with a plurality of actuation assemblies 40$^a$, wherein each actuation assembly 40$^a$ includes sleeve 42$^a$ having two sleeve channels 50$^a$, and two pull members 54$^a$ attached to the ends of the wire axial portions 152$^a$, such that the wire axial portions 152$^a$ extend from the guide member 128, through sleeve distal openings 48$^a$, into a sleeve channels 50$^a$, where they connect to respective pull members 54$^a$ via attachment interfaces 160$^b$, and wherein the pull members 54$^a$ extend further along the sleeve channels 50$^a$, and of the sleeve 42$^a$ through sleeve side openings 52.

According to some embodiments, the method further comprises a step of approximating the sleeve 42$^a$ to the guide member 128, such that they may, for example, contact each other.

According to some embodiments, the method further comprises a step of utilizing the actuation assembly 40$^a$ and the wire 148$^a$ to expand the frame (106) by approximating the guide member 128 and the base member 138 to each other.

According to some embodiments, the step of utilizing the actuation assembly 40$^a$ and the wire 148$^b$ to expand the frame (106) includes simultaneously applying a pull force in a first direction 2 on both pull members 54$^a$, so as to pull the base member 138 in the first direction 2, while the sleeve 42$^a$ is pressed against the guide member 128, applying a counterforce thereto, so as to hold the guide member 128 in place.

According to some embodiments, the step of utilizing the actuation assembly 40$^a$ and the wire 148$^b$ to expand the frame (106) includes applying a push force in a second direction 4 by the sleeve 42$^a$, so as to push the guide member 128 in a second direction 4, while the wire 148$^b$ applies a counter force, via its wire base end portion 150$^b$, against the base member 138, so as to hold the base member 138 in place.

According to some embodiments, the step of utilizing the actuation assembly 40$^a$ and the wire 148$^b$ to expand the frame (106) includes simultaneously applying a pull force in a first direction 2 on both pull members 54$^a$, so as to pull the base member 138 in the first direction 2, while applying a push force in a second direction 4 by the sleeve 42$^a$, so as to push the guide member 128 in a second direction 4.

According to some embodiments, the method further comprises a step of pulling the sleeve 42$^a$ away from the guide member 128, thereby exposing the axial lock portions 154$^b$ of the wire 148$^b$.

According to some embodiments, the step of pulling the sleeve 42$^a$ away from the guide member 128 is executed such that the attachment interfaces 160$^b$ remain within the sleeve channels 50$^a$.

According to some embodiments, the method further comprises a step of rotating the sleeve 42$^a$ around its axis of symmetry, so as to intertwine both axial lock portions 154$^b$ over each other, forming a twist 162$^b$ disposed over the guide member 128.

According to some embodiments, the method further comprises a step of sliding a cutting shaft 70 equipped with a blade 72 in a second direction 4 toward and over the sleeve side openings 52, thereby cutting the sections of the pull members 54$^a$ exiting the sleeve 42$^a$ out of the sleeve side openings 52.

According to some embodiments, the method further comprises a step of retrieving the delivery apparatus (12), including the actuation assemblies 40$^a$, away from the prosthetic valve (100), thereby allowing the slacks 60 of the pull members 54$^a$, along with the portions of the wire axial portions 152$^b$ that remained within the sleeve 42$^a$, to slide out of the sleeve channels 50$^a$.

According to some embodiments, the step of retrieving the delivery apparatus (12) also includes retrieving the proximal cut-off sections of the pull members 54$^a$.

According to some embodiments, knob $32a$ can be a rotatable or otherwise operable knob configured to produce radial expansion. For example, rotation of the knob $32d$ can pull both pull members $54^a$ while keeping the sleeve $42^a$ stationary in position. Alternatively, knob $32a$ can be configured to push the sleeve $42^a$ while keeping the pull members $54^a$ tensioned stationary in position. In another alternative, knob $32a$ can be configured to push the sleeve $42^a$ while both pull members $54^a$ are also pulled.

According to some embodiments, knob $32b$ can be configured to pull the sleeve $42^a$ in a first direction 2, for example—to space it away from the guide member 128.

According to some embodiments, knob $32c$ can be a rotatable or otherwise operable knob configured to rotate the sleeve $42^a$ around its axis of symmetry, so as to facilitate formation of a twist $162^b$ by intertwining the axial lock portions $154^b$ over each other.

According to some embodiments, knob $32d$ can be configured to advance a cutting shaft 70) in a second direction 4, toward and over side openings 52 of the sleeve $42^a$, so as to cut the pull members $54^a$ extending therefrom.

According to some embodiments, the handle 30 can house one or more electric motors which can be actuated by an operator, such as by pressing a button or a switch on the handle 30, to produce movement of components of the delivery apparatus 12. For example, the handle 30 may include one or more motors operable to produce linear movement of components of the actuation assemblies $40^a$, including pull members $54^a$. According to some embodiments, one or more manual or electric control mechanism is configured to produce simultaneous linear and/or rotational movement of all of the pull members $54^a$, the sleeves $42^a$, and/or the cutting shafts 70.

FIGS. 7A-7F schematically show an actuation assembly $40^b$ of a delivery apparatus (12), used in combination with an expansion and locking assembly 126 comprising a wire $148^c$ according to some applications of the present invention. Actuation assembly $40^b$ comprises a sleeve $42^b$ provided with two sleeve channels $50^b$, wherein each sleeve channel $50^b$ extends axially along the length of the sleeve $42^b$, from a corresponding sleeve distal opening $48^b$ defined at the sleeve distal end $44^b$, proximally toward the handle 30.

According to some embodiments, actuation assembly $400^b$ further comprises a couple of pull members $54^b$, extending from the handle 30 and coupled to the wire axial portions $152^c$. The wire $148^c$ may be similar to wire $148^b$ described above with respect to FIGS. 6A-6F, except that the attachment interfaces $160^c$ must include loops or eyelets $158^c$ through which the pull members $54^b$ can be looped.

Each sleeve channel $50^b$ is configured to receive a portion of a wire axial portion $152^c$, and two strands $58^b$ of the corresponding pull member $54^b$. Each wire axial portion $152^c$ partially extends into, and terminates within, a corresponding sleeve channel $50^a$. In the configuration shown in FIG. 7A, each pull member $54^b$ is looped through an eyelet $158^c$ from which two strands $58^b$ thereof extend further in a proximal direction, through the sleeve channel $50^a$, potentially all the way toward, and optionally into, the handle 30.

Figure 7A:
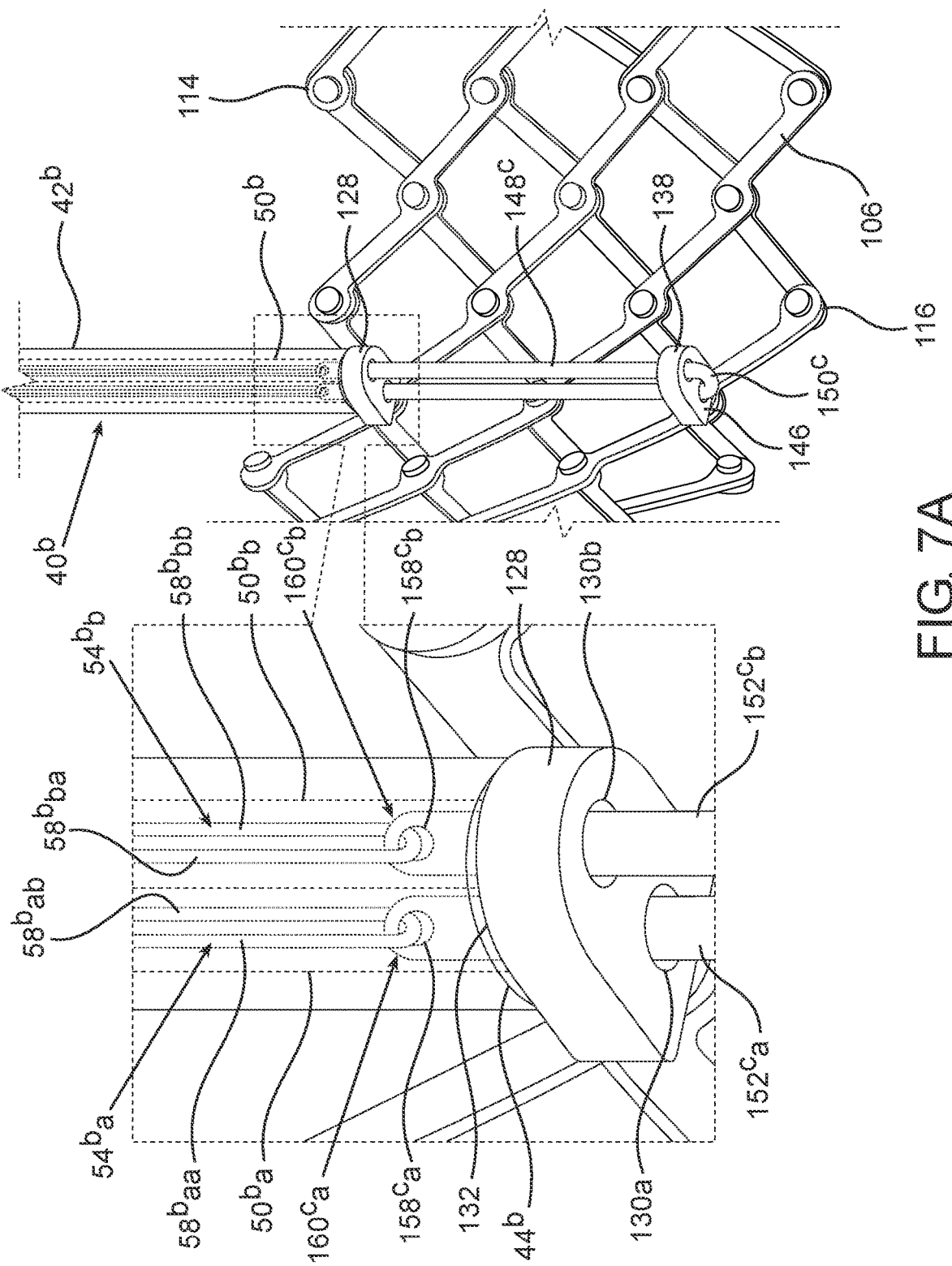

Each pull member $54^b$ is releasably coupled to a corresponding wire axial portion $152^c$. As stated above, each wire axial portion $152^c$ comprises an attachment interface 160), through which a corresponding pull member $54^b$ is looped. According to some embodiments, the attachment interface $160^c$ comprises a loop or an eyelet $158^c$ as shown in FIG. 7A. The pull member $54^b$ is looped through the eyelet $158^c$ such that two strands $58^b$ thereof extend from its loop through the eyelet $158^c$ parallel to each other, proximally along the sleeve channel $50^b$.

Similar to pull members $54^a$, the pull members 546 can be made of soft flexible materials, and may include: non-metallic wires, strings, cables, ropes, sutures, and the like.

FIG. 7A shows an initial step, in which the prosthetic valve (100) is in a state which is not a fully expanded state of the valve, prior to actuation of the expansion and locking assembly 126 by the actuation assembly $40^b$. The valve (100) may be delivered to the site of implantation in a compressed or crimped state, such that the state shown in FIG. 7A can be representative of the valve (100) positioned at the desired site of implantation, potentially exposed from an external capsule or an external shaft, such as the delivery shaft 22 or the outer shaft 20, if it was covered by such a capsule or shaft during the delivery to the implantation site via the delivery apparatus 12. The state shown in FIG. 7A can be a crimped or fully compressed state of the valve (100), as well as a partially compressed, or partially expanded, state of the valve (100).

The wire $148^c$ comprises a wire base end portion $150^c$ looped over the base member second surface 146 between the base member through-holes 140, wherein both of its wire axial portions $152^c$ extend proximally from the wire base end portion $150^c$ through the base member through-holes 140. Specifically, wire axial portion $152^c$a extends from the wire base end portion $150^c$ through base member through-hole $140^a$, toward and into guide member through-hole $130^a$, and into sleeve distal opening $48^b$a, partially along sleeve channel $50^b$a. The wire axial portion $152^c$a terminates within the sleeve channel $50^b$a with an interface $160^c$a in the form of an eyelet $158^c$a. A pull member $54^b$a is looped through the $158^c$a, having two strands $58^b$aa and $58^b$ab thereof, extending proximally therefrom along the remainder of the sleeve channel $50^b$a.

Similarly, wire axial portion $152^c$b extends from the wire base end portion $150^c$ through base member through-hole $140^b$, toward and into guide member through-hole $130^b$, and into sleeve distal opening $48^b$b, partially along sleeve channel $50^b$b. The wire axial portion $152^c$b terminates within the sleeve channel $50^b$b with an interface $160^c$b in the form of an eyelet $158^c$b. A pull member $54^b$b is looped through the $158^c$b, having two strands $58^b$ba and $58^b$bb thereof, extending proximally therefrom along the remainder of the sleeve channel $50^b$b.

According to some embodiments, the diameter the sleeve channels $50^b$ is dimensioned to accommodate the diameter of the wire $148^c$, and is also wide enough to accommodate two strands 586 of a pull member $54^b$ extending therethrough.

According to some embodiments, the diameter of the sleeve channels $50^b$ is not greater than 150% of the diameter of the wire $148^c$. According to some embodiments, the diameter of the sleeve channels $50^b$ is not greater than 120% of the diameter of the wire $148^c$ According to some embodiments, the diameter of the sleeve channels $50^b$ is not greater than 110% of the diameter of the wire $148^c$ According to some embodiments, the diameter of the sleeve channels $50^b$ is not greater than 105% of the diameter of the wire $148^c$.

According to some embodiments, the diameter of the sleeve channels $50^b$ is not greater than 400% of the diameter of a single strand $58^b$ of the pull members $54^b$. According to some embodiments, the diameter of the sleeve channels $50^b$ is not greater than 300% of the diameter of a single strand $58^b$ of the pull members $54^b$. According to some embodiments, the diameter of the sleeve channels $50^b$ is not greater than 250% of the diameter of a single strand 58$^b$ of the pull members 54$^b$. According to some embodiments, the diameter of the sleeve channels 50$^b$ is not greater than 210% of the diameter of a single strand 58$^b$ of the pull members 54$^b$.

According to some embodiments, the diameter of the sleeve channels 50$^b$ is not greater than 150% of the width of the attachment interface 160$^c$ According to some embodiments, the diameter of the sleeve channels 50$^b$ is not greater than 120% of the width of the attachment interface 160$^c$ According to some embodiments, the diameter of the sleeve channels 50$^b$ is not greater than 110% of the width of the attachment interface 160$^c$ According to some embodiments, the diameter of the sleeve channels 50$^b$ is not greater than 105% of the width of the attachment interface 160$^c$.

According to some embodiments, the sleeve 42$^b$ is positioned in the state shown in FIG. 7A in contact with the guide member 128, and more specifically, the sleeve distal end 44$^b$ is in contact, and potentially pressed against, the guide member first surface 134. In some configurations, the valve (100) may be delivered to the site of implantation such that the sleeve distal end 44$^b$ is spaced from the guide member 128. In such configuration, the sleeve 42$^b$ can be advanced, for example, by maneuvering the handle 30, toward the guide member 128, once the valve 100 is positioned at the site of implantation, such that the sleeve distal end 44$^b$ is in contact, and potentially pressed against, the guide member first surface 134.

Figures 7B, 7C:
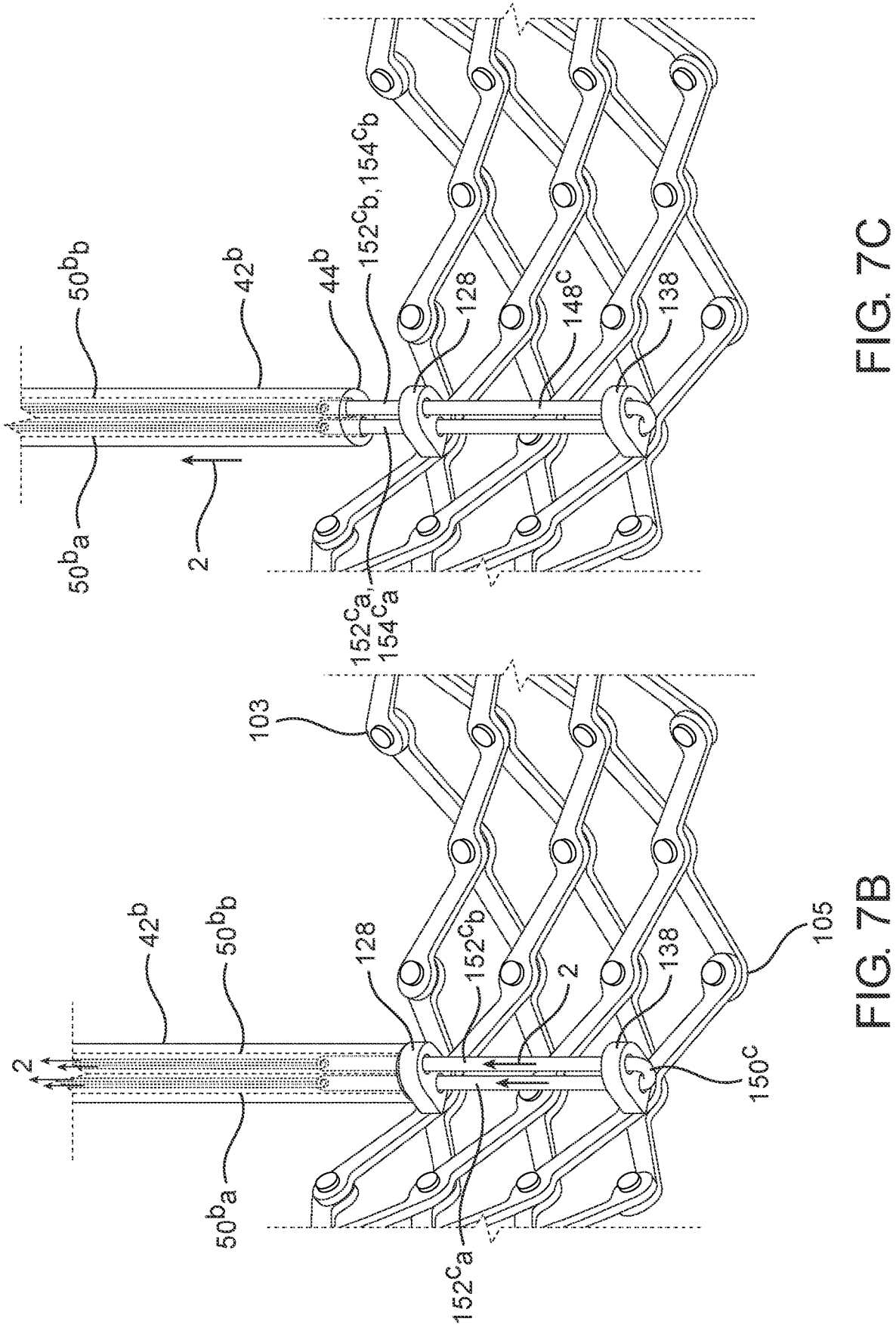

FIG. 7B illustrates a further stage of expanding and locking the prosthetic valve (100), wherein both pull members 546 are simultaneously pulled in a first direction 2, pulling both wire axial portions 152$^c$ there-along, while the sleeve 42$^b$ is pressed against the guide member 128, and more specifically, while the sleeve distal end 44$^b$ is pressed against the guide member first surface 134, to provide a counter-force against the guide member 128.

When all four strands 58$^b$ of both pull members 54$^b$, along with the wire axial portions 152$^c$ coupled thereto, are simultaneously pulled in a first direction 2, the wire base end portion 150$^c$ which is pressed against the base member second portion 146, pulls the base member 138 therewith in the same direction. The counter-force provided by the sleeve 42$^b$ against the guide member 128, allows the base member 138 to be pulled toward the guide member 128.

Approximation of the base member 138 and the guide member 128 to each other can be achieved in numerous ways. According to some embodiments, the guide member 128 is held firmly in place by the sleeve 42$^b$, while the pull force applied to the strands 58$^b$ of pull members 54$^b$, which in turn is applied to the wire axial portions 152$^c$ serves to approximate the base member 138 thereto. According to other embodiments, the force applied to the strands 58$^b$ of pull members 54$^b$, and hence, to the wire axial portions 152$^c$ serves to apply tension to the wire 148$^c$ which is sufficient to hold the base member 138 firmly in place, while the counter force applied by the sleeve 42$^b$ serves to push the guide member 128 in a second direction 4, toward the base member 138. According to yet other embodiments, the pull force applied to the strands 58$^b$ of pull members 54$^b$, and hence, to the wire axial portions 152$^c$ in the first direction 2, and the push or counter force applied by the sleeve 42$^b$ in an opposite second direction 4, serve to simultaneously push the guide member 128 in a second direction 4, and pull the base member 138 in a first direction 2, so as to approximate them to each other.

As the guide member 128 is coupled to the frame 106 at a first location (for example, via guide member fastener 132), and the base member 138 is coupled to the frame 106 at a second location (for example, via base member fastener 142), approximation of the guide member 128 and the base member 138 toward each other, causes the first location and the second location to move toward each other, thereby causing the frame 106 to foreshorten axially and expand radially.

FIG. 7C shows a further stage of expanding and locking the prosthetic valve (100), wherein the sleeve 42$^b$ is pulled in a first direction 2 (e.g., the proximal direction), away from pulling the sleeve 42$^b$ to create a gap between the sleeve distal end 44$^b$ and the guide member first surface 134, exposes axial lock portions 154$^c$a and 154$^c$b, which extend between the guide member first surface 134 and the sleeve distal end 44$^b$.

According to some embodiments, the sleeve 42$^b$ is pulled in the first direction 2 such that the sleeve distal end 44$^b$ remains distal to, or substantially at the level of, the outflow apices 114. According to some embodiments, the sleeve 42$^b$ is pulled in the first direction 2 such that the sleeve distal end 44$^b$ remains distal to, or substantially at the level of, the outflow end 103. According to some embodiments, as further shown in FIG. 7C, the sleeve 42$^b$ is pulled away from the guide member 128 to such a distance, that the attachment interfaces 160$^c$ remain in the corresponding sleeve channels 50$^b$.

It is to be noted that at this stage, if the physician is not satisfied with the expansion diameter of the prosthetic valve (100), the sleeve 42$^b$ can be pushed back toward the guide member 128, until the sleeve distal end 44$^b$ contacts the guide member first surface 134, and the frame 106 may be re-expanded further according to any of the methods described above with respect to FIG. 7B.

Figures 7D, 7E:
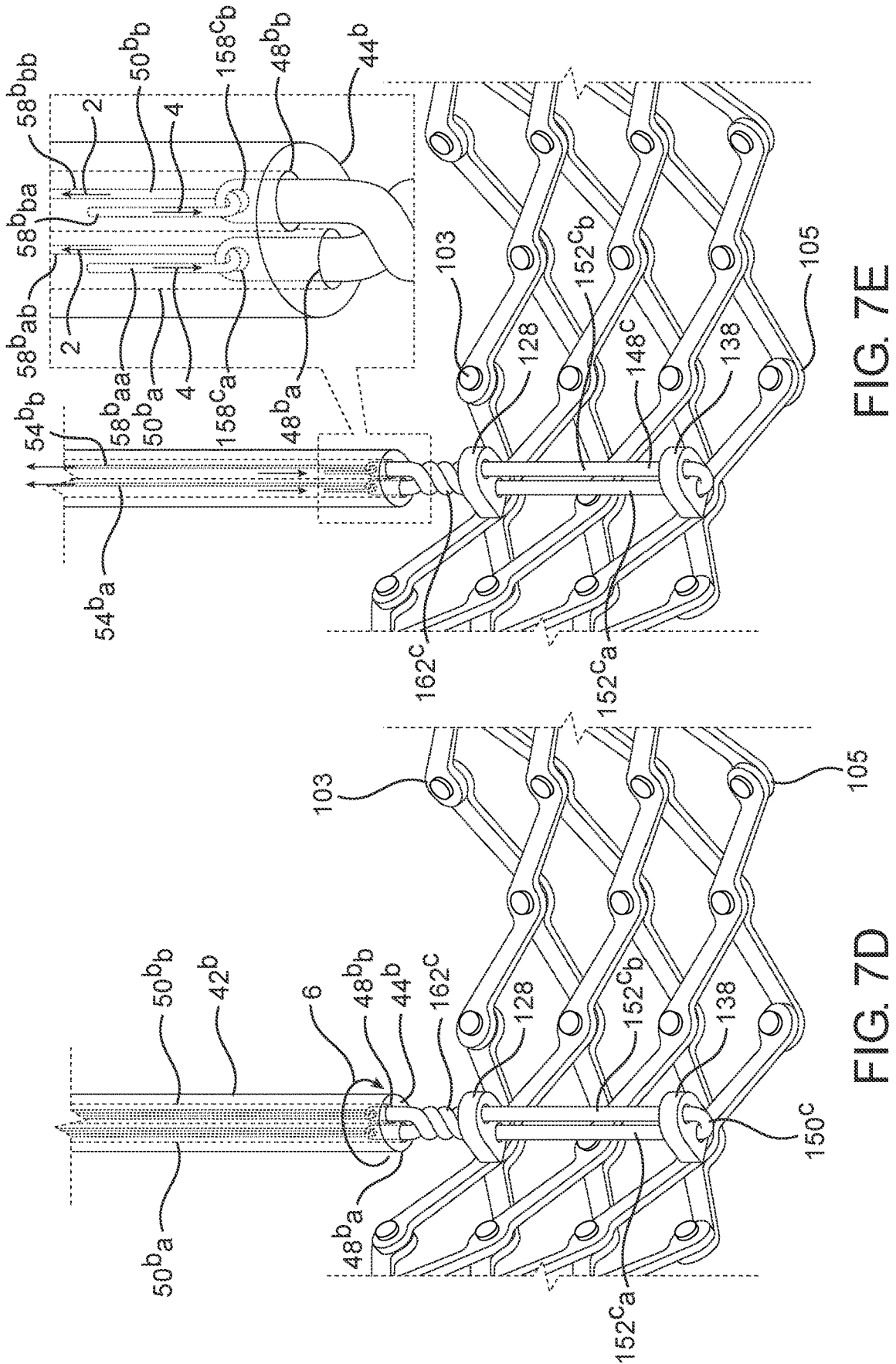

FIG. 7D shows a further stage of expanding and locking the prosthetic valve (100), wherein the sleeve 42$^b$ is rotated around its axis of symmetry, for example in a rotational direction 6 shown in FIG. 7D, such that the axial lock portions 154$^c$a and 154$^c$b are helically intertwined and/or twisted over each other, forming a twist 162$^c$ extending over the guide member first surface 134. In some embodiments, the twist 162$^c$ is proximal to the guide member first surface 134.

As mentioned above, the attachment interfaces 160$^c$ preferably remain within the corresponding sleeve channels 50$^b$, such that rotation of the sleeve 42$^b$ will effectively force the axial lock portions 154$^c$ to twist over each other. If the sleeve 42$^b$ is pulled further prior to such rotation, in a manner that the attachment interfaces 160$^b$ would have been exposed out of (e.g., distal to) the sleeve channels 50$^b$, rotation of the sleeve 42$^b$ would have twisted the softer pull members 54$^b$, which could reversibly intertwine with each other instead of translating the rotational movement to the axiallock portions 154$^c$, thereby failing to form the twist 162$^c$.

FIG. 7E shows a further stage of expanding and locking the prosthetic valve (100), wherein the pull members 54$^b$ are released from the wire axial portions 152$^c$ In order to facilitate the release of pull members 54$^b$, a single strand 58$^b$ of each pull member 54$^b$ is pulled in a first direction 2, while the other strand 58$^b$ is allowed to freely move in the opposite second direction 4, toward the eyelet 158$^b$, until it is released from the eyelet 158$^c$ For example, in the embodiment illustrated in FIG. 7E, strands 58$^b$ab and 58$^b$bb are pulled in a first direction (e.g., proximally-toward, and potentially into, the handle 30), while the opposite strands 58$^b$aa and 58$^b$ba are freely pulled toward the eyelets 158$^c$a and 158$^c$b, respectively, until their free ends are released through these eyelets. Optionally, the pull members 54$^b$a and 54$^b$b may be further pulled in the first direction 2 to retract them from the sleeve channels 50$^b$a and 50$^b$c.

Figure 7F:
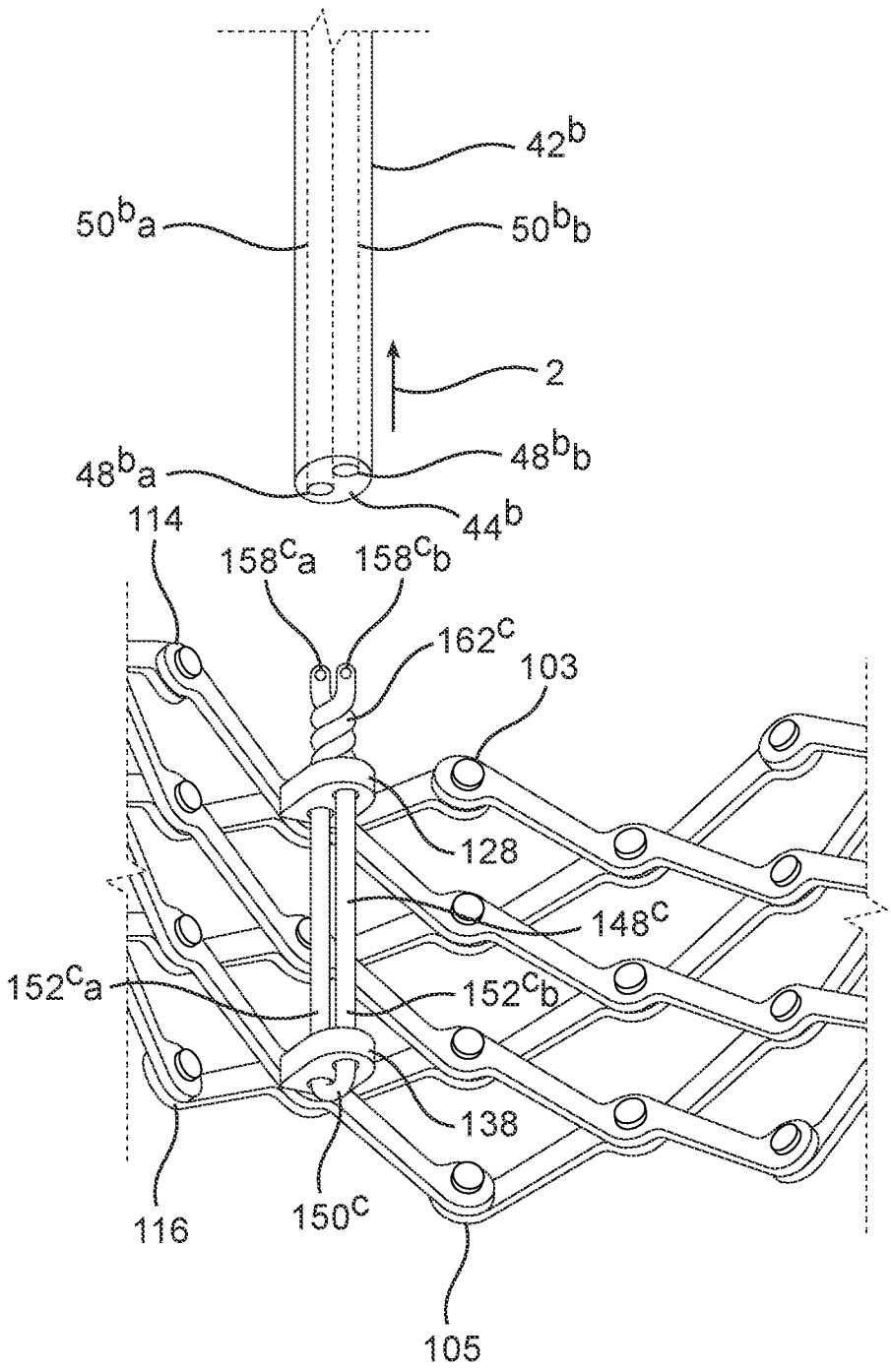

FIG. 7F shows a final stage of expanding and locking the prosthetic valve (100), wherein the actuation assembly 40$^b$ is pulled in the first direction 2 (e.g., the proximal direction), allowing the portions of the wire axial portions 152$^c$ that remained within the sleeve 42$^b$ to slide out of the respective sleeve channels 50$^b$, while the delivery apparatus 12 may be retrieved from the patient's body, leaving the prosthetic valve (100) implanted in the patient.

The plastic deformation of the wire 148$^b$, and specifically that of the axial lock portions 154$^c$ prevents them from unwinding, such that the axial lock portions 154$^c$a and 154$^c$b remain intertwined with each other, together forming the twist 162$^c$ even once the wire 148$^c$ is released from the actuation assembly 406.

In this final expanded state, the wire axial portions 152$^c$a and 152$^c$a are tensioned between the guide member 128 and the base member 138, wherein the wire base end portion 150$^c$ disposed over the base member second surface 146, and the twist 162$^c$ disposed the guide member first surface 134, prevent the guide member 128 and the base member 138 from being distanced away from each other, effectively locking the frame 106 in the expanded diameter.

The patient's native anatomy, such as the native aortic annulus in the case of transcatheter aortic valve implantation, may exert radial forces against the prosthetic valve (100) that would strive to compress it. However, twist 162$^c$ formed over the guide member first surface 134, serves as a locking feature preventing such forces from compressing the frame 106, thereby ensuring that the frame 106 remains locked in the desired radially expanded state.

According to some embodiments, the attachment interfaces 160$^c$ at the end of the twist 162$^c$ do not extend beyond, or proximal to, the outflow apices 114. According to some embodiments, the attachment interfaces 160$^c$ at the end of the twist 162$^c$ do not extend beyond, or proximal to, the outflow end 103.

According to some embodiments, there is provided a method of expanding and locking a prosthetic valve (100), comprising a step of providing a delivery assembly (10) that includes a prosthetic valve (100) equipped with a plurality of expansion and locking assemblies 126 that include a guide member 128 attached to the frame 106 at a first location, a base member 138 attached to the frame 106 at a second location axially spaced from the first location, and a wire 148$^c$ comprising two wire axial portions 152$^c$ extending from a wire base end portion 150$^c$ looped over a base member second surface 146, through base member through-holes 140, toward and through guide member through-holes 130.

The delivery assembly (10) also includes a delivery apparatus (12) equipped with a plurality of actuation assemblies 40$^b$, wherein each actuation assembly 40$^b$ includes sleeve 42$^b$ having two sleeve channels 50$^b$, and two pull members 54$^b$ releasably coupled to the ends of the wire axial portions 152$^c$, such that the wire axial portions 152$^c$ extend from the guide member 128, through sleeve distal openings 48$^b$, into a sleeve channels 50$^b$, where they terminate with eyelets 158$^c$ through which the pull members 54$^b$ are looped, and wherein two strands 58$^b$ of each pull member 54$^b$ extend proximally from the corresponding eyelet 158$^c$ along the sleeve channel 50$^b$.

According to some embodiments, the method further comprises a step of approximating the sleeve 42$^b$ to the guide member 128, such that they may, for example, contact each other.

According to some embodiments, the method further comprises a step of utilizing the actuation assembly 40$^b$ and the wire 148$^c$ to expand the frame (106) by approximating the guide member 128 and the base member 138 to each other.

According to some embodiments, the step of utilizing the actuation assembly 40$^b$ and the wire 148$^c$ to expand the frame (106) includes simultaneously applying a pull force in a first direction 2 on all four strands 58$^b$ of both pull members 54$^b$, so as to pull the base member 138 in the first direction 2, while the sleeve 42$^b$ is pressed against the guide member 128, applying a counterforce thereto, so as to hold the guide member 128 in place.

According to some embodiments, the step of utilizing the actuation assembly 40$^b$ and the wire 148$^c$ to expand the frame (106) includes applying a push force in a second direction 4 by the sleeve 42$^b$, so as to push the guide member 128 in a second direction 4, while the wire 148$^c$ applies a counter force, via its wire base end portion 150$^c$, against base member 138, so as to hold the base member 138 in place.

According to some embodiments, the step of utilizing the actuation assembly 40$^b$ and the wire 148$^c$ to expand the frame (106) includes simultaneously applying a pull force in a first direction 2 on all four strands 58$^b$ of both pull members 54$^b$, so as to pull the base member 138 in the first direction 2, while applying a push force in a second direction 4 by the sleeve 42$^b$, so as to push the guide member 128 in a second direction 4.

According to some embodiments, the method further comprises a step of pulling the sleeve 42$^b$ away from the guide member 128, thereby exposing the axial lock portions 154$^c$ of the wire 148$^c$.

According to some embodiments, the step of pulling the sleeve 42$^b$ away from the guide member 128 is executed such that the eyelets 158$^c$ remain within the sleeve channels 50$^b$.

According to some embodiments, the method further comprises a step of rotating the sleeve 420 around its axis of symmetry, so as to intertwine both axial lock portions 154$^c$ over each other, forming a twist 162$^c$ disposed over the guide member 128.

According to some embodiments, the method further comprises a step of releasing the pull members 54$^b$ from the wire 148$^c$ by pulling a single strand 58$^b$ of each pull member 54$^b$ in a first direction, while allowing the opposite strand 58$^b$ to freely move toward a corresponding eyelet 158$^c$, until it is released therefrom.

According to some embodiments, the method further comprises a step of retrieving the delivery apparatus (12), including the actuation assemblies 40$^b$, away from the prosthetic valve (100), thereby allowing the portions of the wire axial portions 152$^c$ that remained within the sleeve 42$^b$, to slide out of the sleeve channels 50$^b$.

According to some embodiments, knob 32a can be a rotatable or otherwise operable knob configured to produce radial expansion. For example, rotation of the knob 32d can pull all four strands 58$^b$ of both pull members 54$^b$ while keeping the sleeve 42$^b$ stationary in position. Alternatively, knob 32a can be configured to push the sleeve 42$^b$ while keeping all four strands 58$^b$ of the pull members 54$^b$ tensioned stationary in position. In another alternative, knob 32a can be configured to push the sleeve 42$^b$ while both pull members 54$^b$ are also pulled.

According to some embodiments, knob 32b can be configured to pull the sleeve 42$^b$ in a first direction 2, for example—to space it away from the guide member 128.

According to some embodiments, knob $32c$ can be a rotatable or otherwise operable knob configured to rotate the sleeve $42^b$ around its axis of symmetry, so as to facilitate formation of a twist $162^c$ by intertwining the axial lock portions $154^c$ over each other.

According to some embodiments, knob $32d$ can be configured to pull one strand $58^b$ of each pull member $546$ in the first direction, and release the opposite strand $58^b$ of each pull member $546$ to freely move in the opposite second direction $4$, to facilitate release of the pull members $54^b$ from the wire $148$.

According to some embodiments, the handle $30$ can house one or more electric motors which can be actuated by an operator, such as by pressing a button or a switch on the handle $30$, to produce movement of components of the delivery apparatus $12$. For example, the handle $30$ may include one or more motors operable to produce linear movement of components of the actuation assemblies $40^b$, including the strands $58^b$ of pull members $54^b$. According to some embodiments, one or more manual or electric control mechanism is configured to produce simultaneous linear and/or rotational movement of all of the pull members $54^b$ and/or the sleeves $42^b$.

FIGS. 8A-8F schematically show an actuation assembly $40^c$ of a delivery apparatus ($12$), used in combination with an expansion and locking assembly $126$ comprising a wire $148^d$, according to some applications of the present invention. Actuation assembly $40^c$ comprises a sleeve $42^c$ provided with a sleeve lumen or channel $50€$, which extends axially along the length of the sleeve $42^c$, from a sleeve distal opening $48^c$ defined at the sleeve distal end $44^c$, proximally toward the handle $30$.

According to some embodiments, actuation assembly $40^c$ further comprises a pull member $54^c$, extending from handle $30$, and releasably coupled to the wire $148^d$. Unlike wires $148^a$, $148^b$, or $148^c$, the wire $148^d$ defines a closed loop, instead of terminating with two separate end portions of the wire axial portions ($152$). Specifically, wire axial portions $152^d$ of wire $148^d$ are continuously joined at one end (e.g., the distal end of wire $148^d$) at wire base end portion $150^d$, and at the opposite end (e.g., the proximal end of wire $148^d$) at a similarly, yet inversely U-shaped, pull end portion $156^d$, defined as the upper or proximal loop portion of the wire $148^d$.

Similar to pull members $54^a$ or $54^b$, the pull member $54^c$ can comprise soft flexible materials, and may include: non-metallic wires, strings, cables, ropes, sutures, and the like. However, the pull member $54^c$ is further attached a pull-member fastener ($62$) at its distal end. The pull-member fastener is configured to releasably connect with the pull end portion $156^d$ of the wire $148^d$.

According to some embodiments, as illustrated in FIGS. 8A-8F, the fastener is a quick release hook $62$. In the embodiment illustrated in FIG. 8A, the quick release hook $62$ comprises an eyelet (for example, at its proximal end) through which the pull member $54^c$ is looped, such that two strands thereof are shown to extend proximally from the loop. It is to be understood that this mode of attachment is shown by way of illustration and not limitation, and that the pull member $54^c$ can be attached to a pull-member fastener, such as a quick release hook $62$, in any other manner of attachment known in the art, including gluing, welding, suturing, and the like.

It will be further understood that two parallel strands of the pull member $54^c$ are shown by way of illustration and not limitation, and that the pull member $54^c$ can similarly include a single strand attached at its distal end to a pull-member fastener, such as a quick release hook $62$. If the pull member $54^c$ is implemented with two parallel strands, as illustrated for example in FIGS. 8A-8F, any reference to the pull member $54^c$ being pulled in a proximal direction $2$, refers to simultaneously pulling both strands thereof.

Figure 8A:
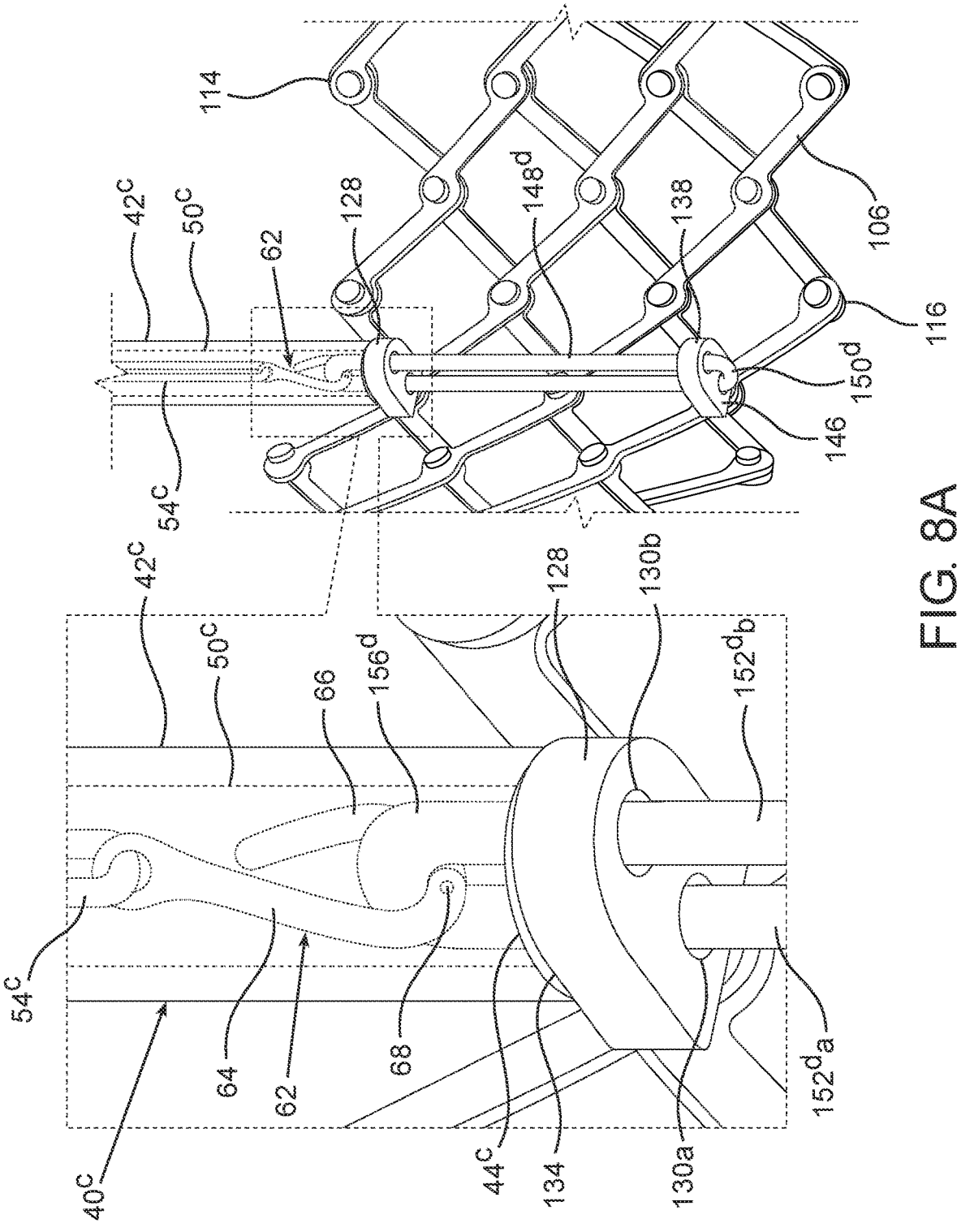

The quick release hook $62$ can include a hook body $64$ defining a partial loop, and a spring-loaded gate $66$ hinged to the hook body $64$ at hinge $68$. The quick release hook $62$ can have an open configuration in a free state thereof, and a closed configuration. FIG. 8A shows the quick release hook $62$ in a closed configuration, wherein the free end of the spring-loaded gate $66$ is forced toward the hook body $64$, such that the hook body $64$ and the spring-loaded gate $66$ enclose, together, an internal space of the quick release hook $62$, through which the pull end portion $156^d$ of the wire $148^d$ is looped.

The wire axial portions $152^a$ partially extends into the sleeve channel $50€$, such that the pull end portion $156^d$ is positioned therein. The sleeve channel $50c$ is configured to accommodate a portion of a wire axial portions $152^d$ and the pull end portion $156^d$, the quick release hook $62$ coupled to the pull end portion $156^d$, and the pull member $54^c$ extending therefrom, potentially all the way toward, and optionally into, the handle $30$.

FIG. 8A shows an initial step, in which the prosthetic valve ($100$) is in a state which is not a fully expanded state of the valve, prior to actuation of the expansion and locking assembly $126$ by the actuation assembly $40^c$ The valve ($100$) may be delivered to the site of implantation in a compressed or crimped state, such that the state shown in FIG. 8A can be representative of the valve ($100$) positioned at the desired site of implantation, potentially exposed from an external capsule or an external shaft, such as the delivery shaft $22$ or the outer shaft $20$, if it was covered by such a capsule or shaft during the delivery to the implantation site via the delivery apparatus $12$. The state shown in FIG. 8A can be a crimped or fully compressed state of the valve ($100$), as well as a partially compressed, or partially expanded, state of the valve ($100$).

The wire $148^d$ comprises a wire base end portion $150^d$ looped over the base member second surface $146$ between the base member through-holes $140$, wherein both of its wire axial portions $152^d$ extend proximally from the wire end portion $150^d$ through the base member through-holes $140$. Specifically, wire axial portion $152^d a$ extends from the wire base end portion $150^d$, through base member through-hole $140a$, toward and into guide member through-hole $130a$. Similarly, wire axial portion $152^d b$ extends from the wire base end portion $150^d$, through base member through-hole $140^b$, toward and into guide member through-hole $130^b$. Both wire axial portions $152^d a$ and $152^d b$ further extend from the guide member through-holes $130$ into the sleeve channel $50^c$ through sleeve distal opening $48^c$, and are joined at the pull end portion $156^d$.

According to some embodiments, the diameter the sleeve channel $50^c$ is dimensioned to accommodate the quick release hook $62$ and the pull end portion $156^d$ looped therethrough. While illustrated to have a uniform diameter, in some implementations the sleeve channel $50^c$ can have a non-uniform profile, comprising a wider distal portion dimensioned to accommodate the quick release hook $62$, and a narrower portion extending therefrom toward the handle $30$, dimensioned to accommodate the pull member $54^c$ (embodiment not shown). In the initial state shown in FIG. 8A, prior to initiation of valve expansion, the quick release hook $62$ is retained within the sleeve channel $50^c$ in a closed configuration, thereby preventing spontaneous release of the pull end portion $156^d$ therefrom.

While the spring-loaded gate 66 strives to spring away from the hook body 64, it is bound by the inner walls of the sleeve channel $50^c$ such that the quick release hook 62 is retained in the closed configuration within the sleeve $42^c$.

According to some embodiments, the diameter of the sleeve channels $50^c$ is large enough to accommodate the quick release hook 62 in a closed configuration thereof, yet narrow enough to prevent the spring-loaded gate 66 to spring away from the hook body 64 in a manner that will transition the quick release hook 62 to the open configuration.

According to some embodiments, the sleeve $42^c$ is positioned in the state shown in FIG. 8A in contact with the guide member 128, and more specifically, the sleeve distal end $44^c$ is in contact, and potentially pressed against, the guide member first surface 134. In some configurations, the valve (100) may be delivered to the site of implantation such that the sleeve distal end $44^c$ is spaced from the guide member 128. In such a configuration, the sleeve $42^c$ can be advanced, for example, by maneuvering the handle 30, toward the guide member 128, once the valve 100 is positioned at the site of implantation, such that the sleeve distal end $44^c$ is in contact, and potentially pressed against, the guide member first surface 134.

Figures 8B, 8C:
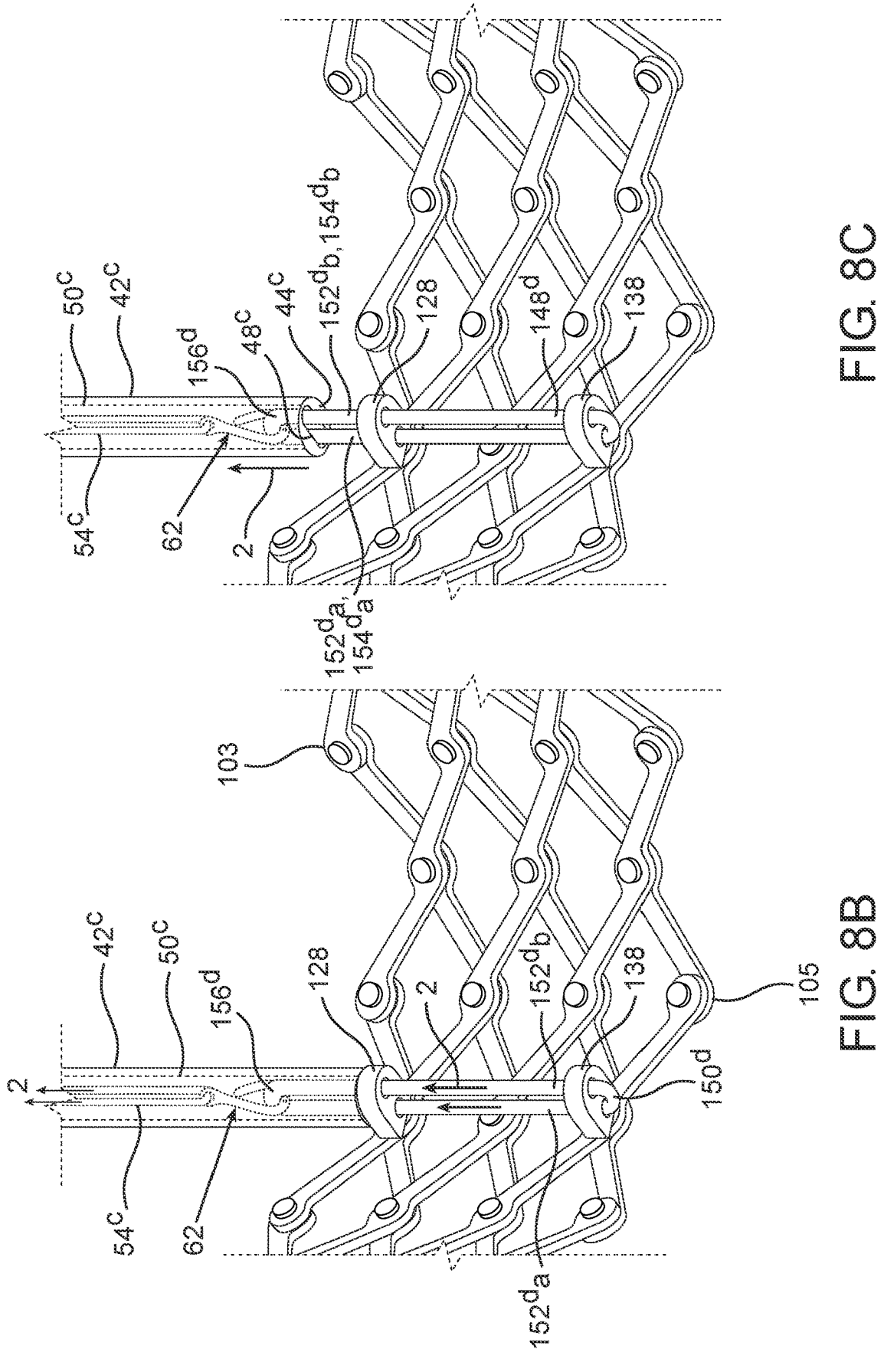

FIG. 8B illustrates a further stage of expanding and locking the prosthetic valve (100), wherein the pull member $54^c$ is pulled in a first direction 2, pulling the quick release hook 62 and the pull end portion $156^d$ coupled thereto, with both of the wire axial portions $152^d$, there-along, while the sleeve $42^c$ is pressed against the guide member 128, and more specifically, while the sleeve distal end $44^c$ is pressed against the guide member first surface 134, to provide a counter-force against the guide member 128.

When the pull member $54^c$ along with the wire axial portions $152^d$ coupled thereto via the quick release hook 62 and the pull end portion $156^d$, are pulled in a first direction 2, the wire base end portion $150^d$, which is pressed against the base member second portion 146, pulls the base member 138 therewith in the same direction. The counter-force provided by the sleeve $42^c$ against the guide member 128, allows the base member 138 to be pulled toward the guide member 128.

Approximation of the base member 138 and the guide member 128 to each other can be achieved in numerous ways. According to some embodiments, the guide member 128 is held firmly in place by the sleeve $42^c$, while the pull force applied to the pull member $54^c$, which in turn is applied to the wire axial portions $152^d$, serves to approximate the base member 138 thereto. According to other embodiments, the force applied to the pull member $54^c$, and hence, to the wire axial portions $152^d$, serves to apply tension to the wire $148^d$, which is sufficient to hold the base member 138 firmly in place, while the counter force applied by the sleeve $42^c$ serves to push the guide member 128 in a second direction 4, toward the base member 138. According to yet other embodiments, the pull force applied to the pull member $54^c$, and hence, to the wire axial portions $152^d$, in the first direction 2, and the push or counter force applied by the sleeve $42^c$ in an opposite second direction 4, serve to simultaneously push the guide member 128 in a second direction 4, and pull the base member 138 in a first direction 2, so as to approximate them to each other.

As the guide member 128 is coupled to the frame 106 at a first location (for example, via guide member fastener 132), and the base member 138 is coupled to the frame 106 at a second location (for example, via base member fastener 142), approximation of the guide member 128 and the base member 138 toward each other, causes the first location and the second location to move toward each other, thereby causing the frame 106 to foreshorten axially and expand radially.

FIG. 8C shows a further stage of expanding and locking the prosthetic valve (100), wherein the sleeve $42^c$ is pulled in a first direction 2 (e.g., the proximal direction), away from the guide member 128, once the valve (100) reaches the desired expansion diameter. As shown, pulling the sleeve $42^c$ to create a gap between the sleeve distal end $44^c$ and the guide member first surface 134, exposes axial lock portions $154^d$a and $154^d$b, which extend between the guide member first surface 134 and the sleeve distal end $44^c$.

According to some embodiments, the sleeve $42^c$ is pulled in the first direction 2 such that the sleeve distal end $44^c$ remains distal to, or substantially at the level of, the outflow apices 114. According to some embodiments, the sleeve $42^c$ is pulled in the first direction 2 such that the sleeve distal end $44^c$ remains distal to, or substantially at the level of, the outflow end 103. According to some embodiments, as further shown in FIG. 8C, the sleeve $42^b$ is pulled away from the guide member 128 to such a distance, that the quick release hook remains in the sleeve channel $50^c$.

It is to be noted that at this stage, if the physician is not satisfied with the expansion diameter of the prosthetic valve (100), the sleeve $42^c$ can be pushed back toward the guide member 128, until the sleeve distal end $44^c$ contacts the guide member first surface 134, and the frame 106 may be re-expanded further according to any of the methods described above with respect to FIG. 8B.

Figures 8D, 8E:
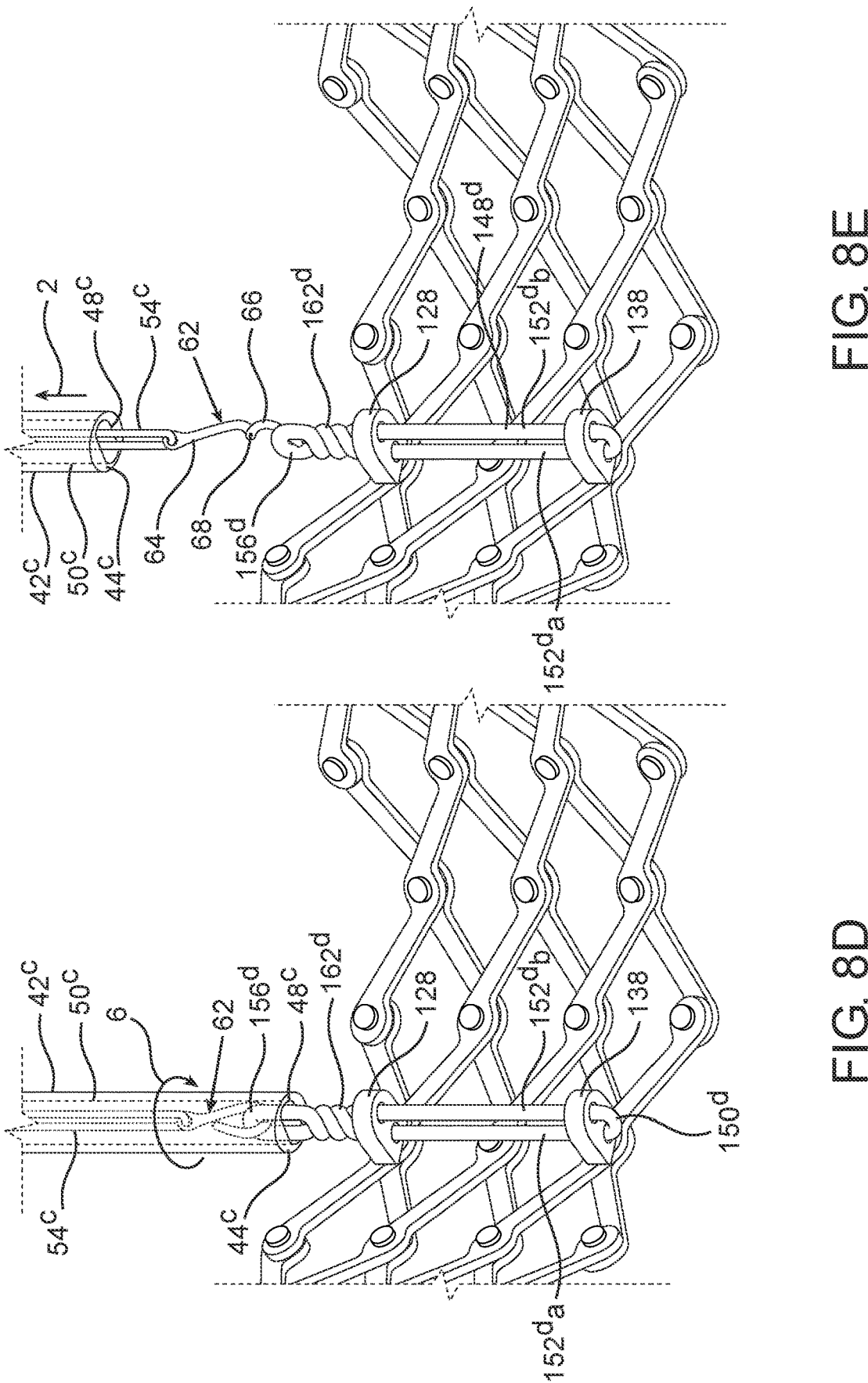

FIG. 8D shows a further stage of expanding and locking the prosthetic valve (100), wherein the sleeve $42^c$ is rotated around its axis of symmetry, for example in a rotational direction 6 shown in FIG. 8D, such that the axial lock portions $154^d$a and $154^d$b are helically intertwined and/or twisted over each other, forming a twist $162^d$ extending over the guide member first surface 134. In some embodiments, the twist $162^d$ is proximal to the guide member first surface 134.

FIG. 8E shows a further stage of expanding and locking the prosthetic valve (100), wherein the pull member $54^c$ is released from the wire $148^d$. In order to facilitate the release of pull member $54^c$, the sleeve $42^c$ is pulled in the first direction 2 (e.g., the proximal direction) relative to the quick release hook 62, until the quick release hook 62 is sufficiently exposed to allow the spring-loaded gate 66 to spring away from the hook body 64, thereby transitioning it to the open configuration shown in FIG. 8E. In this configuration, the pull end portion $156^d$ can be released from the quick release hook 62.

Figure 8F:
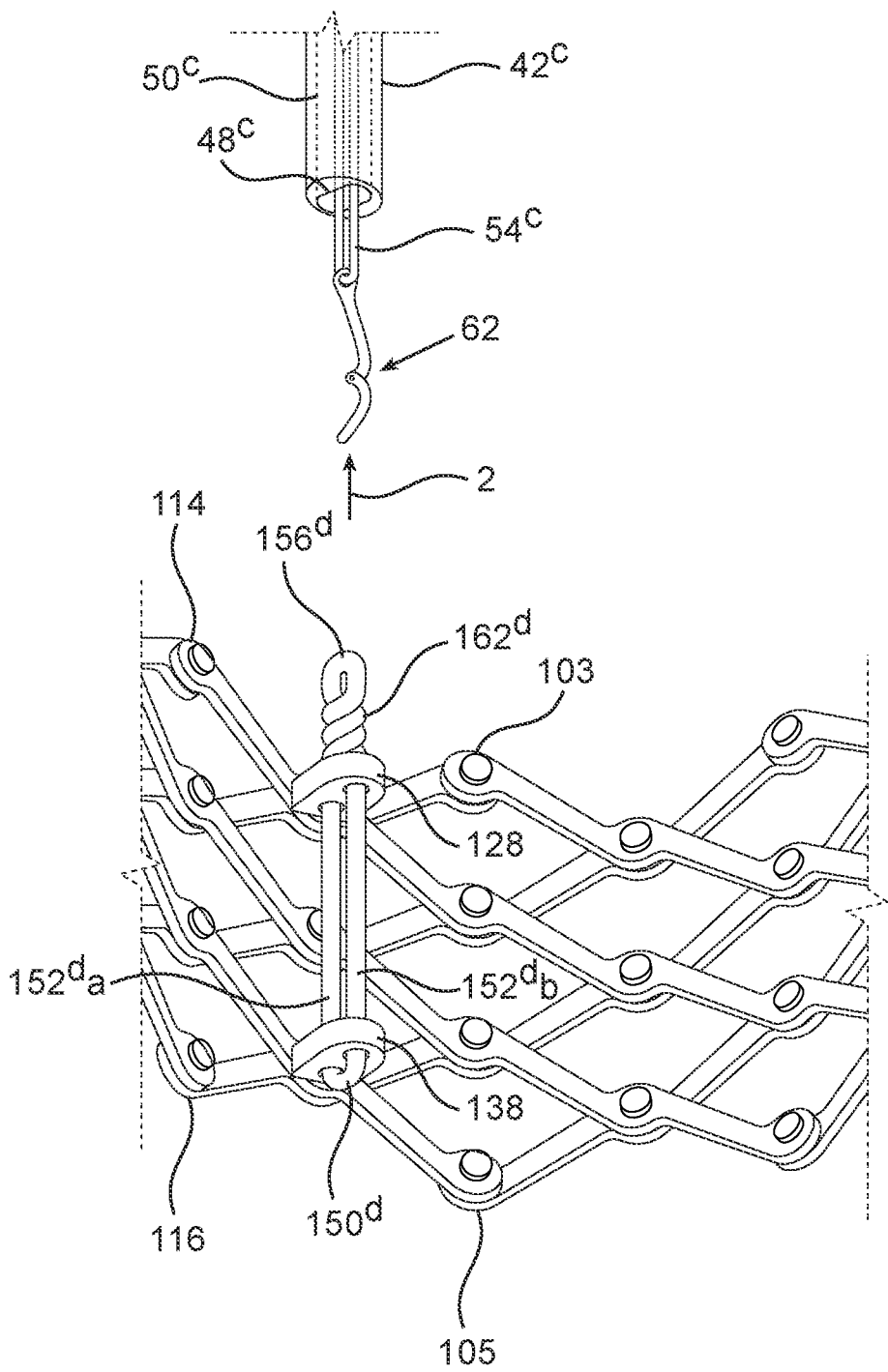

FIG. 8F shows a final stage of expanding and locking the prosthetic valve (100), wherein the actuation assembly $40^c$ is pulled in the first direction 2 (e.g., the proximal direction), allowing the pull end portion $156^d$ to slide away from the quick release hook 62, while the delivery apparatus 12 may be retrieved from the patient's body, leaving the prosthetic valve (100) implanted in the patient.

The plastic deformation of the wire $148^d$, and specifically that of the axial lock portions $154^d$, prevents them from unwinding, such that the axial lock portions $154^d$a and $154^d$b remain intertwined with each other, together forming the twist $162^d$, even once the wire $148^d$ is released from the actuation assembly $40^c$.

In this final expanded state, the wire axial portions $152^d$a and $152^d$a are tensioned between the guide member 128 and the base member 138, wherein the wire base end portion 150$^d$ disposed over the base member second surface 146, and the twist 162$^d$ disposed the guide member first surface 134, prevent the guide member 128 and the base member 138 from being distanced away from each other, effectively locking the frame 106 in the expanded diameter.

The patient's native anatomy, such as the native aortic annulus in the case of transcatheter aortic valve implantation, may exert radial forces against the prosthetic valve (100) that would strive to compress it. However, twist 162$^d$, formed over the guide member first surface 134, serves as a locking feature preventing such forces from compressing the frame 106, thereby ensuring that the frame 106 remains locked in the desired radially expanded state.

According to some embodiments, the pull end portion 156$^d$ at the end of the twist 162$^a$ does not extend beyond, or proximal to, the outflow apices 114. According to some embodiments, the pull end portion 156$^d$ at the end of the twist 162$^d$ does not extend beyond, or proximal to, the outflow end 103.

According to some embodiments, there is provided a method of expanding and locking a prosthetic valve (100), comprising a step of providing a delivery assembly (10) that includes a prosthetic valve (100) equipped with a plurality of expansion and locking assemblies 126 that include a guide member 128 attached to the frame 106 at a first location, a base member 138 attached to the frame 106 at a second location axially spaced from the first location, and a wire 148$^d$ comprising two wire axial portions 152$^d$ joined at one end of the wire 148$^d$ at a wire base end portion 150$^d$, and at the opposite end of the wire 148$^d$ at a pull end portion 156$^d$. The wire base end portion 150$^d$ is looped over a base member second surface 146, and the wire axial portions 152$^d$ extend therefrom through base member through-holes 140, toward and through guide member through-holes 130.

The delivery assembly (10) also includes a delivery apparatus (12) equipped with a plurality of actuation assemblies 40$^c$, wherein each actuation assembly 40$^c$ includes sleeve 42$^c$ having a sleeve lumen or channel 50$^c$, a pull member 54$^c$ releasably coupled via a quick release hook 62, to the pull end portion 156$^d$, such that the wire axial portions 152$^d$ extend from the guide member 128, through a sleeve distal opening 48$^c$, into the sleeve channel 50$^c$, in which the pull end portion 156$^d$ is looped through the quick release hook 62, and wherein the pull member 54$^c$ is attached to the quick release hook 62 and extends proximally therefrom along the sleeve channel 50$^c$.

According to some embodiments, the method further comprises a step of approximating the sleeve 42$^c$ to the guide member 128, such that they may, for example, contact each other.

According to some embodiments, the method further comprises a step of utilizing the actuation assembly 40$^c$ and the wire 148$^d$ to expand the frame (106) by approximating the guide member 128 and the base member 138 to each other.

According to some embodiments, the step of utilizing the actuation assembly 40$^c$ and the wire 148$^d$ to expand the frame (106) includes simultaneously applying a pull force in a first direction 2 on the pull member 54$^c$, so as to pull the base member 138 in the first direction 2, while the sleeve 42$^c$ is pressed against the guide member 128, applying a counterforce thereto, so as to hold the guide member 128 in place.

According to some embodiments, the step of utilizing the actuation assembly 40$^c$ and the wire 148$^d$ to expand the frame (106) includes applying a push force in a second direction 4 by the sleeve 42$^c$, so as to push the guide member

128 in a second direction 4, while the wire 148$^d$ applies a counter force, via its wire base end portion 150$^d$, against the base member 138, so as to hold the base member 138 in place.

According to some embodiments, the step of utilizing the actuation assembly 40$^c$ and the wire 148$^d$ to expand the frame (106) includes simultaneously applying a pull force in a first direction 2 on the pull member 54$^d$, so as to pull the base member 138 in the first direction 2, while applying a push force in a second direction 4 by the sleeve 42$^c$, so as to push the guide member 128 in a second direction 4.

According to some embodiments, the method further comprises a step of pulling the sleeve 42$^c$ away from the guide member 128, thereby exposing the axial lock portions 154$^d$ of the wire 148$^d$.

According to some embodiments, the step of pulling the sleeve 42$^c$ away from the guide member 128 is executed such that the quick release hook 62 remains within the sleeve channel 50$^c$.

According to some embodiments, the method further comprises a step of rotating the sleeve 42$^c$ around its axis of symmetry, so as to intertwine both axial lock portions 154$^d$ over each other, forming a twist 162$^a$ disposed over the guide member 128.

According to some embodiments, the method further comprises a step of releasing the pull member 54$^d$ from the wire 148$^d$, by pulling the sleeve 42$^c$ relative to the quick release hook 62, sufficiently to expose the quick release hook 62 and allow a spring-loaded gate 66 thereof to spring away to its free state, thereby transitioning the quick release hook 62 to an open configuration thereof.

According to some embodiments, the method further comprises a step of retrieving the delivery apparatus (12), including the actuation assemblies 40$^c$, away from the prosthetic valve (100), thereby allowing the pull end portion 156$^d$ to slide away from the quick release hook 62.

According to some embodiments, knob 32$a$ can be a rotatable or otherwise operable knob configured to produce radial expansion. For example, rotation of the knob 32$d$ can pull the pull member 54$^c$ while keeping the sleeve 42$^c$ stationary in position. Alternatively, knob 32$^a$ can be configured to push the sleeve 42$^c$ while keeping the pull member 54$^c$ tensioned stationary in position. In another alternative, knob 32$a$ can be configured to push the sleeve 42$^c$ while the pull member 54$^c$ is also pulled.

According to some embodiments, knob 32$b$ can be configured to pull the sleeve 42$^c$ in a first direction 2, for example—to space it away from the guide member 128.

According to some embodiments, knob 32$c$ can be a rotatable or otherwise operable knob configured to rotate the sleeve 42$^c$ around its axis of symmetry, so as to facilitate formation of a twist 162$^d$ by intertwining the axial lock portions 154$^d$ over each other.

According to some embodiments, knob 32$b$ can be further utilized to further pull the sleeve 42$^c$ in a first direction 2, for example—to expose the quick release hook and allow it to transition to the open configuration, thereby facilitating release of the pull member 54$^c$ from the wire 148$^d$.

According to some embodiments, the handle 30 can house one or more electric motors which can be actuated by an operator, such as by pressing a button or a switch on the handle 30, to produce movement of components of the delivery apparatus 12. For example, the handle 30 may include one or more motors operable to produce linear movement of components of the actuation assemblies 40$^c$, including the pull members 54$^c$ and/or the sleeves 42$^c$. According to some embodiments, one or more manual or electric control mechanism is configured to produce simultaneous linear and/or rotational movement of all of the pull members $54^c$ and/or the sleeves $42^c$.

While a specific type of a pull-member fastener, is demonstrated as a quick release hook 62 hereinabove with respect to FIGS. 8A-8F, it is to be understood that other types of releasable fasteners are contemplated, as long as they may be retained in a configuration that does not allow spontaneous release of the pull end portion $156^d$ therefrom, prior to formation of a twist $162^d$, and may be controllably released from the pull end portion $156^a$ thereafter.

FIGS. 9A-9F schematically show another embodiment of an actuation assembly $40^c$ of a delivery apparatus (12), used in combination with an expansion and locking assembly 126 comprising a wire $148^d$. Actuation assembly $40^c$ can be similar to the actuation assembly described above with respect to FIGS. 8A-8F. Specifically, actuation assembly $40^c$ comprises a sleeve $42^c$ provided with a sleeve lumen or channel $50^c$, which extends axially along the length of the sleeve $42^c$, from a sleeve distal opening $48^c$ defined at the sleeve distal end $44^c$, proximally toward the handle 30.

Wire $148^b$ shown in FIGS. 9A-9F may be identical to the wire described above with respect to FIGS. 8A-8F, defining a closed loop. Specifically, wire axial portions $152^d$ of wire $148^d$ are continuously joined at one end (e.g., the distal end of wire $148^d$) at wire base end portion $150^d$, and at the opposite end (e.g., the proximal end of wire $148^d$) at a similarly, yet inversely U-shaped, pull end portion $156^d$, defined as the upper or proximal loop portion of the wire $148^d$.

According to some embodiments, actuation assembly $40^c$ further comprises a pull member $54^d$, extending from the handle 30 and releasably coupled to the pull end portion $156^d$, without a quick release hook (62). The sleeve channel $50^c$ is configured to receive a portion of wire axial portions $152^d$, along with the pull end portion $156^d$ joining them, and two strands $58^d$ of the pull member $54^d$. In the configuration shown in FIG. 9A, the pull member $54^d$ is looped through the pull end portion $156^d$, from which two strands $58^d$ thereof extend further in a proximal direction, through the sleeve channel $50^c$, potentially all the way toward, and optionally into, the handle 30.

Similar to pull members $54^a$, $54^b$, or $54^c$, the pull member $54^c$ can be made of soft flexible materials, and may include: non-metallic wires, strings, cables, ropes, sutures, and the like.

Figure 9A:
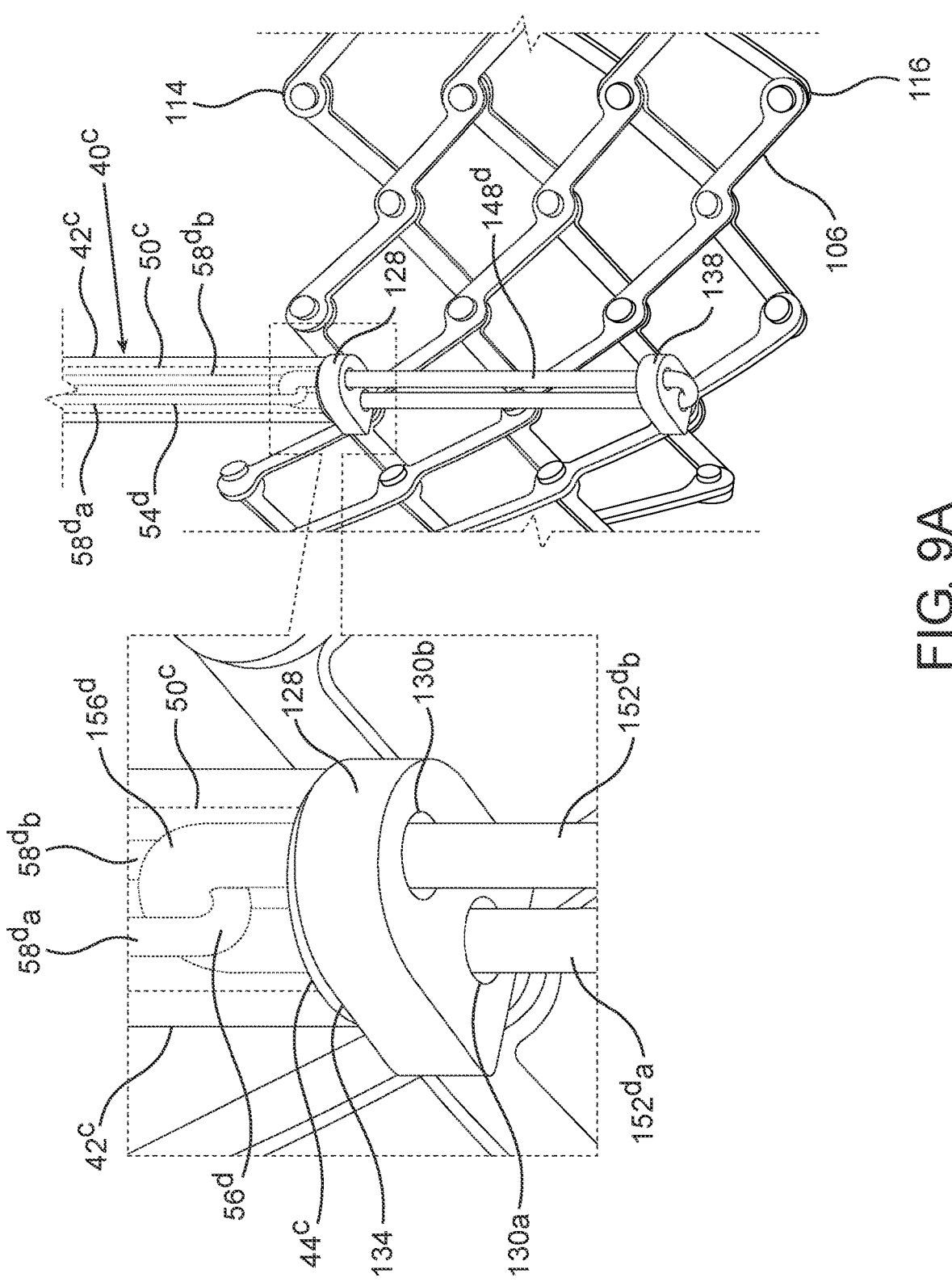

FIG. 9A shows an initial step, in which the prosthetic valve (100) is in a state which is not a fully expanded state of the valve, prior to actuation of the expansion and locking assembly 126 by the actuation assembly $40^c$. The valve (100) may be delivered to the site of implantation in a compressed or crimped state, such that the state shown in FIG. 9A can be representative of the valve (100) positioned at the desired site of implantation, potentially exposed from an external capsule or an external shaft, such as the delivery shaft 22 or the outer shaft 20, if it was covered by such a capsule or shaft during the delivery to the implantation site via the delivery apparatus 12. The state shown in FIG. 9A can be a crimped or fully compressed state of the valve (100), as well as a partially compressed, or partially expanded, state of the valve (100).

The wire $148^d$ comprises a wire base end portion $150^d$ looped over the base member second surface 146 between the base member through-holes 140, wherein both of its wire axial portions $152^d$ extend proximally from the wire base end portion $150^d$ through the base member through-holes 140. Specifically, wire axial portion $152^d$a extends from the wire base end portion $150^d$, through base member through-hole $140^a$, toward and into guide member through-hole $130^a$. Similarly, wire axial portion $152^d$b extends from the wire base end portion $150^d$, through base member through-hole $140^b$, toward and into guide member through-hole $130^b$. Both wire axial portions $152^d$a and $152^d$b further extend from the guide member through-holes 130 into the sleeve channel $50^c$ through sleeve distal opening $48^c$, and are joined at the pull end portion $156^d$.

According to some embodiments, the diameter the sleeve channel $50^c$ is dimensioned to accommodate two wire axial portions $152^a$ along with the pull end portion $156^d$ joining them, and is also wide enough to accommodate two strands $58^d$ of the pull member $54^d$ extending therethrough.

According to some embodiments, the diameter of the sleeve channel $50^c$ is not greater than 400% of the diameter of a single strand $58^d$ of the pull member $54^d$. According to some embodiments, the diameter of the sleeve channel $50^c$ is not greater than 300% of the diameter of a single strand $58^d$ of the pull member $54^d$. According to some embodiments, the diameter of the sleeve channel $50^c$ is not greater than 250% of the diameter of a single strand $58^a$ of the pull member $54^d$. According to some embodiments, the diameter of the sleeve channel $50^c$ is not greater than 210% of the diameter of a single strand $58^d$ of the pull member $54^d$.

According to some embodiments, the diameter of the sleeve channel $50^c$ is not greater than 400% of the diameter of a single wire axial portion $152^d$. According to some embodiments, the diameter of the sleeve channel $50^c$ is not greater than 300% of the diameter of a single wire axial portion $152^d$. According to some embodiments, the diameter of the sleeve channel $50^c$ is not greater than 250% of the diameter of a single wire axial portion $152^d$. According to some embodiments, the diameter of the sleeve channel $50^c$ is not greater than 210% of the diameter of a single wire axial portion $152^d$.

According to some embodiments, the diameter of the sleeve channel 50€ is not greater than 150% of the width of the pull end portion $156^d$, defined as the distance between the two outermost edges of the wire axial portion $152^d$ joined by the pull end portion $156^d$. According to some embodiments, the diameter of the sleeve channel $50^c$ is not greater than 120% of the width of the pull end portion $156^d$. According to some embodiments, the diameter of the sleeve channel $50c$ is not greater than 110% of the width of the pull end portion $156^d$. According to some embodiments, the diameter of the sleeve channel $50^c$ is not greater than 105% of the width of the pull end portion $156^d$.

According to some embodiments, the sleeve $42^c$ is positioned in the state shown in FIG. 9A in contact with the guide member 128, and more specifically, the sleeve distal end $44^c$ is in contact, and potentially pressed against, the guide member first surface 134. In some configurations, the valve (100) may be delivered to the site of implantation such that the sleeve distal end $44^c$ is spaced from the guide member 128. In such a configuration, the sleeve $42^c$ can be advanced, for example, by maneuvering the handle 30, toward the guide member 128, once the valve 100 is positioned at the site of implantation, such that the sleeve distal end $44^c$ is in contact, and potentially pressed against, the guide member first surface 134.

Figures 9B, 9C:
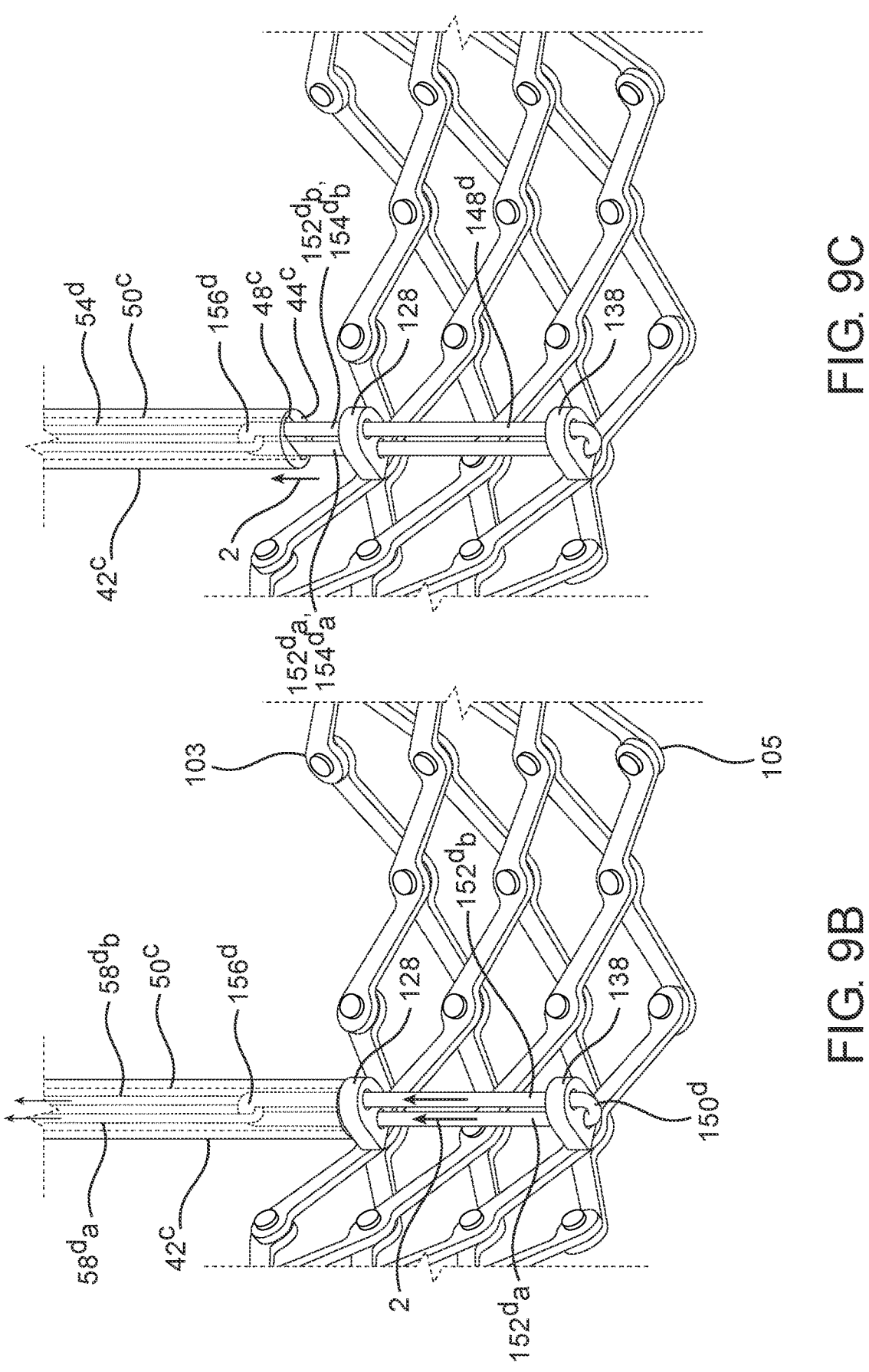

FIG. 9B illustrates a further stage of expanding and locking the prosthetic valve (100), wherein the pull member $54^d$ is pulled in a first direction 2, pulling the pull end portion $156^d$ and both wire axial portions $152^d$ extending therefrom, there-along, while the sleeve $42^c$ is pressed against the guide member 128, and more specifically, while the sleeve distal end 44$^c$ is pressed against the guide member first surface 134, to provide a counter-force against the guide member 128.

When both strands 58$^d$ of the pull member 54$^d$, along with the wire axial portions 152$^a$ coupled thereto, are simultaneously pulled in a first direction 2, the wire base end portion 150$^d$, which is pressed against the base member second portion 146, pulls the base member 138 therewith in the same direction. The counter-force provided by the sleeve 42$^c$ against the guide member 128, allows the base member 138 to be pulled toward the guide member 128.

Approximation of the base member 138 and the guide member 128 to each other can be achieved in numerous ways. According to some embodiments, the guide member 128 is held firmly in place by the sleeve 42$^d$, while the pull force applied to the strands 58$^d$ of pull member 54$^d$, which in turn is applied to the wire axial portions 152$^d$, serves to approximate the base member 138 thereto. According to other embodiments, the force applied to the strands 58$^d$ of pull member 54$^d$, and hence, to the wire axial portions 152$^d$, serves to apply tension to the wire 148$^d$, which is sufficient to hold the base member 138 firmly in place, while the counter force applied by the sleeve 42$^c$ serves to push the guide member 128 in a second direction 4, toward the base member 138. According to yet other embodiments, the pull force applied to the strands 58$^d$ of pull member 54$^d$, and hence, to the wire axial portions 152$^d$, in the first direction 2, and the push or counter force applied by the sleeve 42$^c$ in an opposite second direction 4, serve to simultaneously push the guide member 128 in a second direction 4, and pull the base member 138 in a first direction 2, so as to approximate them to each other.

As the guide member 128 is coupled to the frame 106 at a first location (for example, via guide member fastener 132), and the base member 138 is coupled to the frame 106 at a second location (for example, via base member fastener 142), approximation of the guide member 128 and the base member 138 toward each other, causes the first location and the second location to move toward each other, thereby causing the frame 106 to foreshorten axially and expand radially.

FIG. 9C shows a further stage of expanding and locking the prosthetic valve (100), wherein the sleeve 42$^c$ is pulled in a first direction 2 (e.g., the proximal direction), away from pulling the sleeve 42$^c$ to create a gap between the sleeve distal end 44$^c$ and the guide member first surface 134, exposes axial lock portions 154$^d$a and 154$^a$b, which extend between the guide member first surface 134 and the sleeve distal end 44$^c$.

According to some embodiments, the sleeve 42$^c$ is pulled in the first direction 2 such that the sleeve distal end 44$^c$ remains distal to, or substantially at the level of, the outflow apices 114. According to some embodiments, the sleeve 42$^c$ is pulled in the first direction 2 such that the sleeve distal end 44$^c$ remains distal to, or substantially at the level of, the outflow end 103. According to some embodiments, as further shown in FIG. 9C, the sleeve 42$^c$ is pulled away from the guide member 128 to such a distance, that the pull end portion 156$^d$ remains in the sleeve channel 50$^c$.

It is to be noted that at this stage, if the physician is not satisfied with the expansion diameter of the prosthetic valve (100), the sleeve 42$^c$ can be pushed back toward the guide member 128, until the sleeve distal end 44$^c$ contacts the guide member first surface 134, and the frame 106 may be re-expanded further according to any of the methods described above with respect to FIG. 9B.

Figures 9D, 9E:
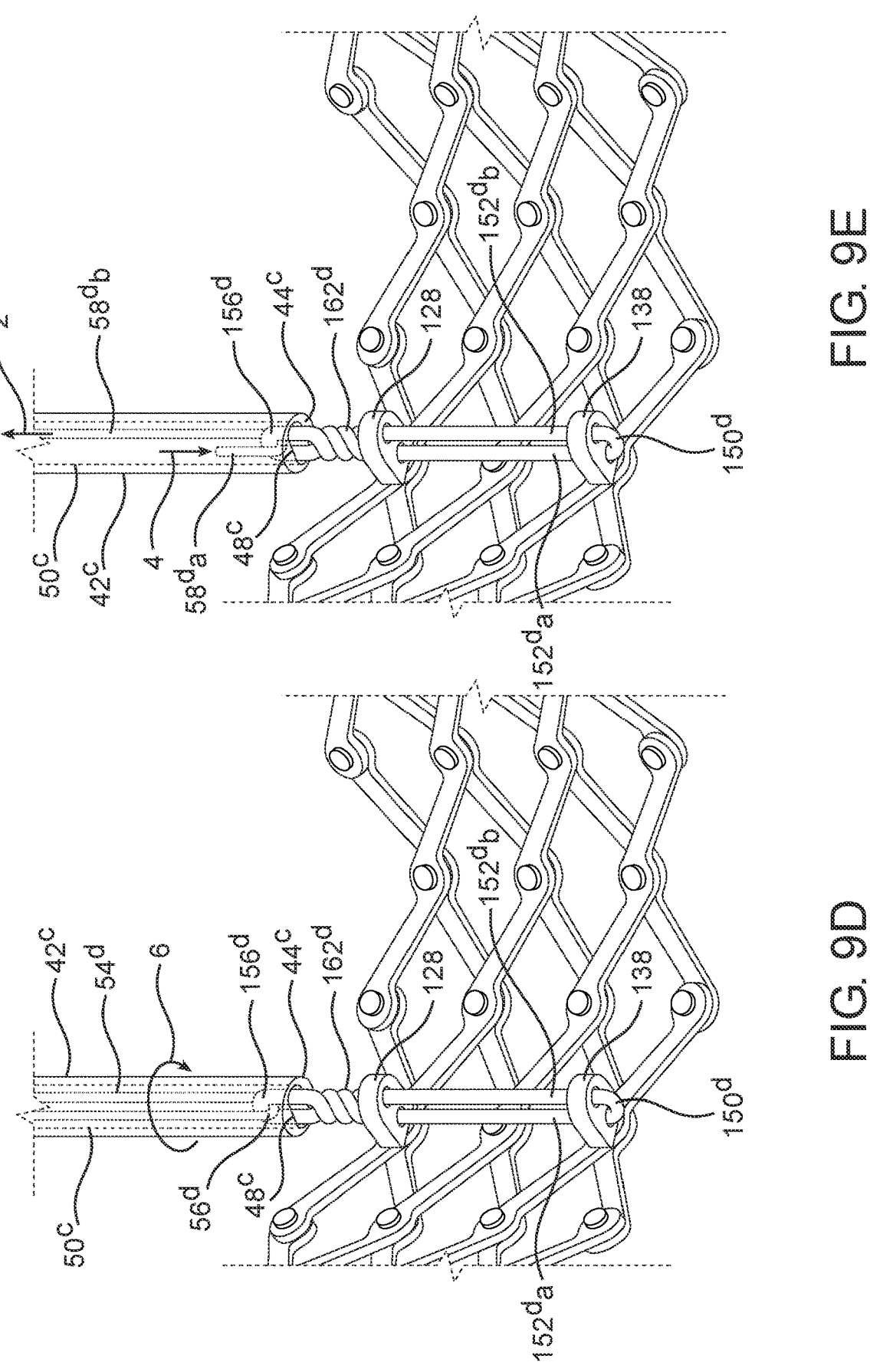

FIG. 9D shows a further stage of expanding and locking the prosthetic valve (100), wherein the sleeve 42$^c$ is rotated around its axis of symmetry, for example in a rotational direction 6 shown in FIG. 9D, such that the axial lock portions 154$^d$a and 154$^d$b are helically intertwined and/or twisted over each other, forming a twist 162$^d$ extending over the guide member first surface 134. In some embodiments, the twist 162$^d$ is proximal to the guide member first surface 134.

As mentioned above, the pull end portion 156$^d$ preferably remains within the sleeve channel 50$^d$, such that rotation of the sleeve 42$^c$ will effectively force the axial lock portions 154$^d$ to twist over each other. If the sleeve 42$^c$ is pulled further prior to such rotation, in a manner that the pull end portion 156$^d$ would have been exposed out of (e.g., distal to) the sleeve channel 50$^c$, rotation of the sleeve 42$^c$ would have twisted the strands 58$^d$ of the softer pull member 54$^d$, which could reversibly intertwine with each other instead of translating the rotational movement to the axial lock portions 154$^d$, thereby failing to form the twist 162$^d$.

FIG. 9E shows a further stage of expanding and locking the prosthetic valve (100), wherein the pull member 54$^d$ is released from the pull end portion 156$^d$. In order to facilitate the release of pull member 54$^d$, a single strand 58$^d$ of the pull member 54$^d$ is pulled in a first direction 2, while the other strand 58$^d$ is allowed to freely move in the opposite second direction 4, toward the pull end portion 156$^d$, until it is released from the pull end portion 156$^d$. For example, in the embodiment illustrated in FIG. 9E, strand 58$^d$b is pulled in a first direction (e.g., proximally-toward, and potentially into, the handle 30), while the opposite strand 58$^d$a is freely pulled toward the pull end portion 156$^d$, until its free end is released through the pull end portion 156$^d$. Optionally, the pull member 54$^d$ may be further pulled in the first direction 2 to retract it from the sleeve channel 50$^c$.

Figure 9F:
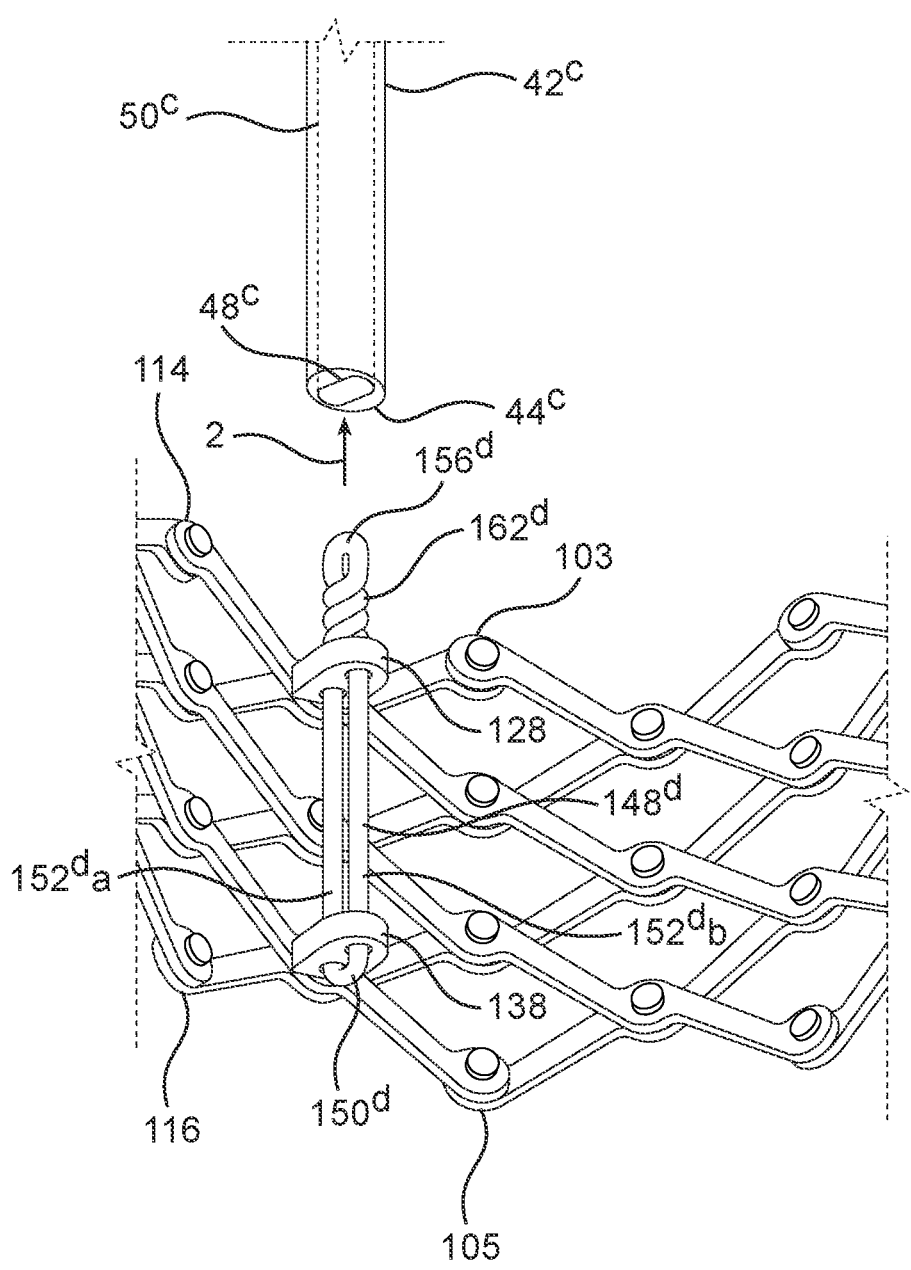

FIG. 9F shows a final stage of expanding and locking the prosthetic valve (100), wherein the actuation assembly 40$^c$ is pulled in the first direction 2 (e.g., the proximal direction), allowing the portions of the wire axial portions 152$^a$ that remained within the sleeve 42$^c$, along with the pull end portion 156$^d$, to slide out of the sleeve channel 50$^c$, while the delivery apparatus 12 may be retrieved from the patient's body, leaving the prosthetic valve (100) implanted in the patient.

The plastic deformation of the wire 148$^d$, and specifically that of the axial lock portions 154$^d$, prevents them from unwinding, such that the axial lock portions 154$^d$a and 154$^d$b remain intertwined with each other, together forming the twist 162$^d$, even once the wire 148$^d$ is released from the actuation assembly 40$^c$.

In this final expanded state, the wire axial portions 152$^d$a and 152$^d$a are tensioned between the guide member 128 and the base member 138, wherein the wire base end portion 150$^a$ disposed over the base member second surface 146, and the twist 162$^d$ disposed the guide member first surface 134, prevent the guide member 128 and the base member 138 from being distanced away from each other, effectively locking the frame 106 in the expanded diameter.

The patient's native anatomy, such as the native aortic annulus in the case of transcatheter aortic valve implantation, may exert radial forces against the prosthetic valve (100) that would strive to compress it. However, twist 162$^d$, formed over the guide member first surface 134, serves as a locking feature preventing such forces from compressing the frame 106, thereby ensuring that the frame 106 remains locked in the desired radially expanded state.

According to some embodiments, the pull end portion $156^d$ at the end of the twist $162^a$ does not extend beyond, or proximal to, the outflow apices 114. According to some embodiments, the pull end portion $156^d$ at the end of the twist $162^d$ does not extend beyond, or proximal to, the outflow end 103.

According to some embodiments, there is provided a method of expanding and locking a prosthetic valve (100), comprising a step of providing a delivery assembly (10) that includes a prosthetic valve (100) equipped with a plurality of expansion and locking assemblies 126 that include a guide member 128 attached to the frame 106 at a first location, a base member 138 attached to the frame 106 at a second location axially spaced from the first location, and a wire $148^d$ comprising two wire axial portions $152^d$ joined at one end of the wire $148^d$ at a wire base end portion $150^d$, and at the opposite end of the wire $148^d$ at a pull end portion $156^d$. The wire base end portion $150^a$ is looped over a base member second surface 146, and the wire axial portions $152^d$ extend therefrom through base member through-holes 140, toward and through guide member through-holes 130.

The delivery assembly (10) also includes a delivery apparatus (12) equipped with a plurality of actuation assemblies $40^c$, wherein each actuation assembly $40^c$ includes sleeve $42^c$ having a sleeve lumen or channel $50^c$, and a pull member $54^d$ releasably coupled to the pull end portion $156^d$, such that the wire axial portions $152^d$ extend from the guide member 128, through a sleeve distal opening $48^c$, into the sleeve channel $50^c$, joined therein at the pull end portion $156^d$, through which the pull member $54^a$ is looped, and wherein two strands $58^d$ of the pull member $54^d$ extend proximally from the pull end portion $156^d$ along the sleeve channel $50^c$.

According to some embodiments, the method further comprises a step of approximating the sleeve $42^c$ to the guide member 128, such that they may, for example, contact each other.

According to some embodiments, the method further comprises a step of utilizing the actuation assembly $40^c$ and the wire $148^d$ to expand the frame (106) by approximating the guide member 128 and the base member 138 to each other.

According to some embodiments, the step of utilizing the actuation assembly $40^c$ and the wire $148^b$ to expand the frame (106) includes simultaneously applying a pull force in a first direction 2 on both strands $58^d$ of the pull member $54^d$, so as to pull the base member 138 in the first direction 2, while the sleeve $42^c$ is pressed against the guide member 128, applying a counterforce thereto, so as to hold the guide member 128 in place.

According to some embodiments, the step of utilizing the actuation assembly $40^c$ and the wire $148^d$ to expand the frame (106) includes applying a push force in a second direction 4 by the sleeve $42^c$, so as to push the guide member 128 in a second direction 4, while the wire $148^d$ applies a counter force, via its wire base end portion $150^d$, against the base member 138, so as to hold the base member 138 in place.

According to some embodiments, the step of utilizing the actuation assembly $40^c$ and the wire $148^d$ to expand the frame (106) includes simultaneously applying a pull force in a first direction 2 on both strands $58^d$ of the pull member $54^d$, so as to pull the base member 138 in the first direction 2, while applying a push force in a second direction 4 by the sleeve $42^c$, so as to push the guide member 128 in a second direction 4.

According to some embodiments, the method further comprises a step of pulling the sleeve $42^c$ away from the guide member 128, thereby exposing the axial lock portions $154^d$ of the wire $148^d$.

According to some embodiments, the step of pulling the sleeve $42^c$ away from the guide member 128 is executed such that the pull end portion $156^d$ remains within the sleeve channel $50^c$.

According to some embodiments, the method further comprises a step of rotating the sleeve $42^c$ around its axis of symmetry, so as to intertwine both axial lock portions $154^d$ over each other, forming a twist $162^d$ disposed over the guide member 128.

According to some embodiments, the method further comprises a step of releasing the pull member $54^d$ from the wire $148^d$, by pulling a single $58^d$ of the pull member $54^d$ in a first direction, while allowing the opposite strand $58^d$ to freely move toward the pull end portion $156^d$, until it is released therefrom.

According to some embodiments, the method further comprises a step of retrieving the delivery apparatus (12), including the actuation assemblies $40^c$, away from the prosthetic valve (100), thereby allowing the portions of the wire axial portions $152^a$ that remained within the sleeve $42^c$, along with the pull end portion $156^d$, to slide out of the sleeve channel $50^c$.

According to some embodiments, knob 32a can be a rotatable or otherwise operable knob configured to produce radial expansion. For example, rotation of the knob $32^d$ can pull both strands $58^d$ of the pull member $54^d$ while keeping the sleeve $42^c$ stationary in position. Alternatively, knob 32a can be configured to push the sleeve $42^c$ while keeping both strands $58^d$ of the pull member $54^d$ tensioned stationary in position. In another alternative, knob 32a can be configured to push the sleeve $42^c$ while both strands $58^d$ of the pull member $54^d$ are also pulled.

According to some embodiments, knob 32b can be configured to pull the sleeve $42^c$ in a first direction 2, for example—to space it away from the guide member 128.

According to some embodiments, knob 32c can be a rotatable or otherwise operable knob configured to rotate the sleeve $42^c$ around its axis of symmetry, so as to facilitate formation of a twist $162^d$ by intertwining the axial lock portions $154^d$ over each other.

According to some embodiments, knob 32d can be configured to pull one strand $58^d$ of the pull member $54^d$ in the first direction, and release the opposite strand $58^d$ of each to freely move in the opposite second direction 4, to facilitate release of the pull member $54^d$ from the wire $148^d$.

According to some embodiments, the handle 30 can house one or more electric motors which can be actuated by an operator, such as by pressing a button or a switch on the handle 30, to produce movement of components of the delivery apparatus 12. For example, the handle 30 may include one or more motors operable to produce linear movement of components of the actuation assemblies $40^c$, including the strands $58^d$ of pull member $54^d$. According to some embodiments, one or more manual or electric control mechanism is configured to produce simultaneous linear and/or rotational movement of all of the pull members $54^d$ and/or the sleeves 42c.

FIGS. 10A-10E schematically shows an actuation assembly $40^d$ of a delivery apparatus (12), used in combination with an expansion and locking assembly 126 comprising a wire $148^d$, according to some embodiments. Actuation assembly $40^d$ can be similar to the actuation assembly $40^c$ described above with respect to FIGS. 8A-9F. Specifically, actuation assembly $40^d$ comprises a sleeve $42^d$ provided with a sleeve lumen or channel 504, which extends axially along the length of the sleeve $42^d$, from a sleeve distal opening $48^c$ defined at the sleeve distal end 444, proximally toward the handle 30.

The wire $148^d$ shown in FIGS. 10A-10E may be identical to the wire described above with respect to FIGS. 8A-9F, defining a closed loop. Specifically, wire axial portions $152^d$ of wire $148^d$ are continuously joined at one end (e.g., the distal end of wire $148^d$) at wire base end portion $150^d$, and at the opposite end (e.g., the proximal end of wire $148^d$) at a similarly, yet inversely U-shaped, pull end portion $156^d$, defined as the upper or proximal loop portion of the wire $148^d$.

According to some embodiments, actuation assembly $40^d$ further comprises a pull member 54e, extending from the handle 30 and releasably coupled to the pull end portion $156^d$. Unlike any of the embodiments described above in conjunction with FIGS. 8A-8F or 9A-9F, the pull member $54^e$ comprises a bendable distal portion 74 that can transition from a biased configuration to an unbiased configuration. In the biased configuration, shown in FIG. 10A for example, the bendable distal portion 74 is bend over itself, forming a U-shaped bent section 78 between a first pull-member section 76 that extends between the handle 30 and the bent section 78, and a second pull-member section 80 terminating at a free end 82. The bendable distal portion 74 is configured to releasably connect with the pull end portion $156^d$ of the wire $148^d$, allowing the pull end portion $156^d$ of the wire $148^d$ to be looped over the bendable distal portion 74 in the biased configuration.

The bendable distal portion 74, and potentially the entire pull member $54^e$, can be made of a shape-memory material which is able to return to an unbiased shaped or configuration under certain conditions. For example, the shape-memory material may be comprised of a shape-memory alloy, such as Nitinol, or a spring-tempered steel, such that the bendable distal portion 74 may be retained in a bent configuration by the inner walls of the sleeve channel $50^d$, yet return to a relaxed shape-recovering position, defined as the unbiased configuration, when the second pull-member section 80 is no longer restricted by the sleeve channel 50) d.

The wire axial portions $152^d$ partially extends into the sleeve channel $50^d$, such that the pull end portion $156^d$ is positioned therein. The sleeve channel $50^d$ is configured to accommodate a portion of a wire axial portions $152^d$ and the pull end portion $156^d$, as well as the bendable distal portion 74 in its biased configuration.

In some embodiments, the sleeve 42 of the actuation assembly 40 comprises a threaded proximal portion 43, threadedly attached to the handle 30 of the delivery apparatus (12). For example, sleeve $42^a$ shown in FIG. 10A comprises a threaded proximal portion $43^a$, that can be coupled to an actuation mechanism (not shown) within handle 30 that can threaded the sleeve $42^a$ so as to apply simultaneous rotational and axial movement thereto.

Figure 10A:
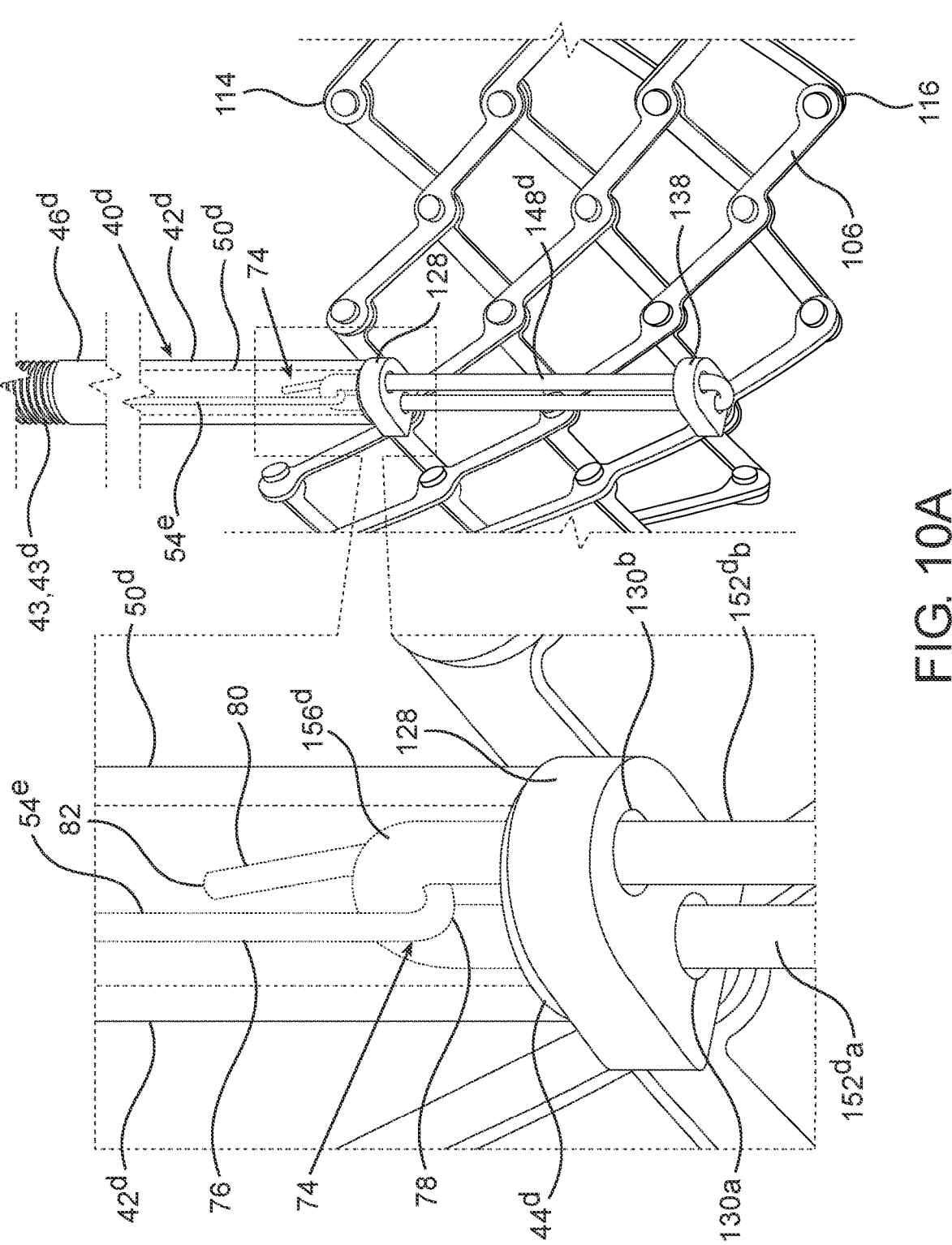

FIG. 10A shows an initial step, in which the prosthetic valve (100) is in a state which is not a fully expanded state of the valve, prior to actuation of the expansion and locking assembly 126 by the actuation assembly 404. The valve (100) may be delivered to the site of implantation in a compressed or crimped state, such that the state shown in FIG. 10A can be representative of the valve (100) positioned at the desired site of implantation, potentially exposed from an external capsule or an external shaft, such as the delivery shaft 22 or the outer shaft 20, if it was covered by such a capsule or shaft during the delivery to the implantation site via the delivery apparatus 12. The state shown in FIG. 10A can be a crimped or fully compressed state of the valve (100), as well as a partially compressed, or partially expanded, state of the valve (100).

The wire $148^d$ comprises a wire base end portion $150^d$ looped over the base member second surface 146 between the base member through-holes 140, wherein both of its wire axial portions $152^a$ extend proximally from the wire base end portion $150^d$ through the base member through-holes 140. Specifically, wire axial portion $152^d$a extends from the wire base end portion $150^d$, through base member through-hole $140^a$, toward and into guide member through-hole $130^a$. Similarly, wire axial portion $152^d$b extends from the wire base end portion $150^d$, through base member through-hole $140^b$, toward and into guide member through-hole $130^b$. Both wire axial portions $152^d$a and $152^d$b further extend from the guide member through-holes 130 into the sleeve channel $50^d$ through sleeve distal opening 484, and are joined at the pull end portion $156^d$.

According to some embodiments, the diameter the sleeve channel $50^d$ is dimensioned to accommodate the bendable distal portion 74 in its biased configuration, and the pull end portion $156^a$ looped therethrough. While illustrated to have a uniform diameter, in some implementations the sleeve channel $50^d$ can have a non-uniform profile, comprising a wider distal portion dimensioned to accommodate the bendable distal portion 74 in its biased configuration, and a narrower portion extending therefrom toward the handle 30, dimensioned to accommodate the first pull-member section 76 (embodiment not shown). In the initial state shown in FIG. 10A, prior to initiation of valve expansion, the bendable distal portion 74 is retained within the sleeve channel $50^d$ in a biased configuration, thereby preventing spontaneous release of the pull end portion $156^d$ therefrom.

While the second pull-member section 80 strives to spring away from the first pull-member section 76, it is bound by the inner walls of the sleeve channel $50^d$, such that the bendable distal portion 74 is retained in the biased configuration within the sleeve $42^d$.

According to some embodiments, the diameter of the sleeve channels $50^d$ is large enough to accommodate the bendable distal portion 74 in a biased configuration thereof, yet narrow enough to prevent the second pull-member section 80 to spring away from the first pull-member section 76 in a manner that will transition the quick release hook 62 to the open configuration.

According to some embodiments, the sleeve $42^d$ is positioned in the state shown in FIG. 10A in contact with the guide member 128, and more specifically, the sleeve distal end $44^d$ is in contact, and potentially pressed against, the guide member first surface 134. In some configurations, the valve (100) may be delivered to the site of implantation such that the sleeve distal end $44^d$ is spaced from the guide member 128. In such a configuration, the sleeve $42^d$ can be advanced, for example, by maneuvering the handle 30, toward the guide member 128, once the valve 100 is positioned at the site of implantation, such that the sleeve distal end $44^d$ is in contact, and potentially pressed against, the guide member first surface 134.

Figures 10B, 10C:
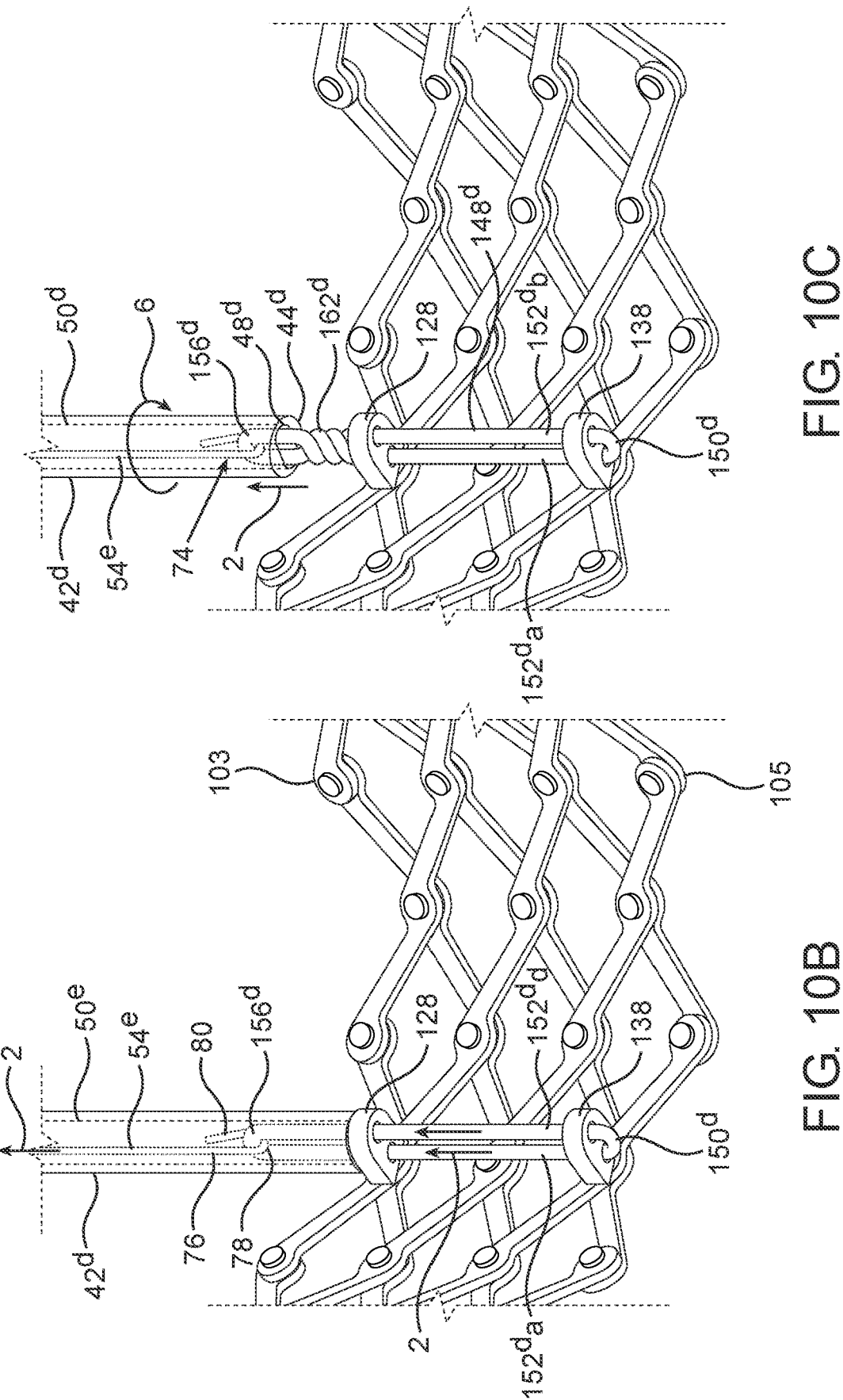

FIG. 10B illustrates a further stage of expanding and locking the prosthetic valve (100), wherein the pull member $54^e$ is pulled in a first direction 2, pulling the bendable distal portion 74 and the pull end portion $156^d$ coupled thereto, with both of the wire axial portions $152^d$, there-along, while the sleeve $42^d$ is pressed against the guide member 128, and more specifically, while the sleeve distal end $44^d$ is pressed against the guide member first surface 134, to provide a counter-force against the guide member 128.

When the pull member 54$^c$, along with the wire axial portions 152$^d$ coupled thereto via the bendable distal portion 74 and the pull end portion 156$^d$, are pulled in a first direction 2, the wire base end portion 150$^d$, which is pressed against the base member second portion 146, pulls the base member 138 therewith in the same direction. The counter-force provided by the sleeve 42$^d$ against the guide member 128, allows the base member 138 to be pulled toward the guide member 128.

Approximation of the base member 138 and the guide member 128 to each other can be achieved in numerous ways. According to some embodiments, the guide member 128 is held firmly in place by the sleeve 42$^d$, while the pull force applied to the pull member 54$^e$, which in turn is applied to the wire axial portions 152$^d$, serves to approximate the base member 138 thereto. According to other embodiments, the force applied to the pull member 54$^c$, and hence, to the wire axial portions 152$^d$, serves to apply tension to the wire 148$^d$, which is sufficient to hold the base member 138 firmly in place, while the counter force applied by the sleeve 42$^a$ serves to push the guide member 128 in a second direction 4, toward the base member 138. According to yet other embodiments, the pull force applied to the pull member 54$^e$, and hence, to the wire axial portions 152$^d$, in the first direction 2, and the push or counter force applied by the sleeve 42$^d$ in an opposite second direction 4, serve to simultaneously push the guide member 128 in a second direction 4, and pull the base member 138 in a first direction 2, so as to approximate them to each other.

As the guide member 128 is coupled to the frame 106 at a first location (for example, via guide member fastener 132), and the base member 138 is coupled to the frame 106 at a second location (for example, via base member fastener 142), approximation of the guide member 128 and the base member 138 toward each other, causes the first location and the second location to move toward each other, thereby causing the frame 106 to foreshorten axially and expand radially.

FIG. 10C shows a further stage of expanding and locking the prosthetic valve (100), wherein the sleeve 42$^a$ is simultaneously rotated and pulled in the axial direction, for example by threading its threaded proximal portion 43$^d$ within the handle (30). As shown, the sleeve 42$^d$ is threaded in a direction that facilitates axial movement thereof in a first direction 2 (e.g., the proximal direction), away from the guide member 128, once the valve (100) reaches the desired expansion diameter. This axial movement of the sleeve 42$^d$ forms a gap between the sleeve distal end 44$^a$ and the guide member first surface 134.

At the same time, the rotational movement of the sleeve 42$^a$ around its axis of symmetry, for example in a rotational direction 6 shown in FIG. 10C, serves to helically intertwine or twist the axial lock portions 154$^d$a and 154$^d$b over each other, forming a twist 162$^a$ extending over the guide member first surface 134. In some embodiments, the twist 162$^d$ is proximal to the guide member first surface 134. This twist 162$^a$ is exposed through the gap formed between the sleeve distal end 44$^d$ and the guide member first surface 134 during the axial movement of the sleeve 42$^d$.

The axial lock portions 154$^d$a and 154$^d$b continue to twist over each other as long as the bendable distal portion 74 remains in a biased configuration within the sleeve channel 504. It is to be noted that at this stage, if the physician is not satisfied with the expansion diameter of the prosthetic valve (100), the sleeve 42$^d$ can be threaded in an opposite direction to push it back toward the guide member 128, and simultaneously rotate in the opposite direction to unravel the twist 162$^d$, until the sleeve distal end 44$^d$ contacts the guide member first surface 134, and the frame 106 may be re-expanded further according to any of the methods described above with respect to FIG. 10B.

Figure 10D:
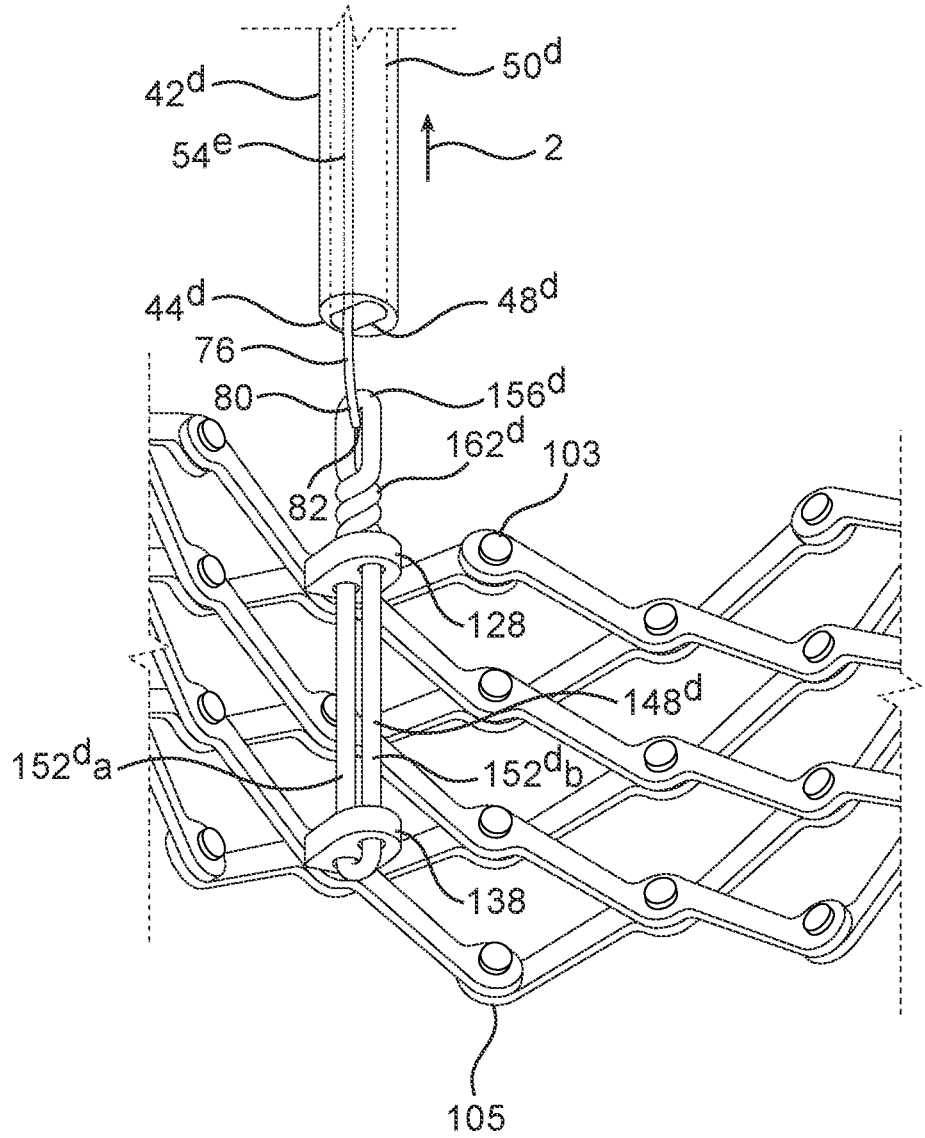

FIG. 10D shows a further stage of expanding and locking the prosthetic valve (100), wherein the pull member 54$^e$ is released from the wire 148$^d$. In order to facilitate the release of pull member 54$^c$, the sleeve 42$^d$ is further pulled in the first direction 2 (e.g., the proximal direction) relative to the bendable distal portion 74, until the bendable distal portion 74 is sufficiently exposed to allow the second pull-member section 80 to spring away from the first pull-member section 76 (for example, to a relatively straightened configuration in which the second pull-member section 80 is continuously aligned with the first pull-member section 76), thereby transitioning the bendable distal portion 74 to the unbiased or open configuration shown in FIG. 10D. In this configuration, the pull end portion 156$^d$ can be released from the pull member 54$^e$.

Axial movement of the sleeve 42$^d$ to expose the bendable distal portion 74 can be achieved, in some embodiments, by continuously threading the sleeve 42$^a$ in the same manner described above in conjunction with FIG. 10C. Alternatively, rotational movement of the sleeve 42$^a$ can be halted by stopping the threaded movement after a satisfactory formation of the twist 162$^d$, and instead pulling the entire sleeve 42$^a$ solely in the axial direction.

Figure 10E:
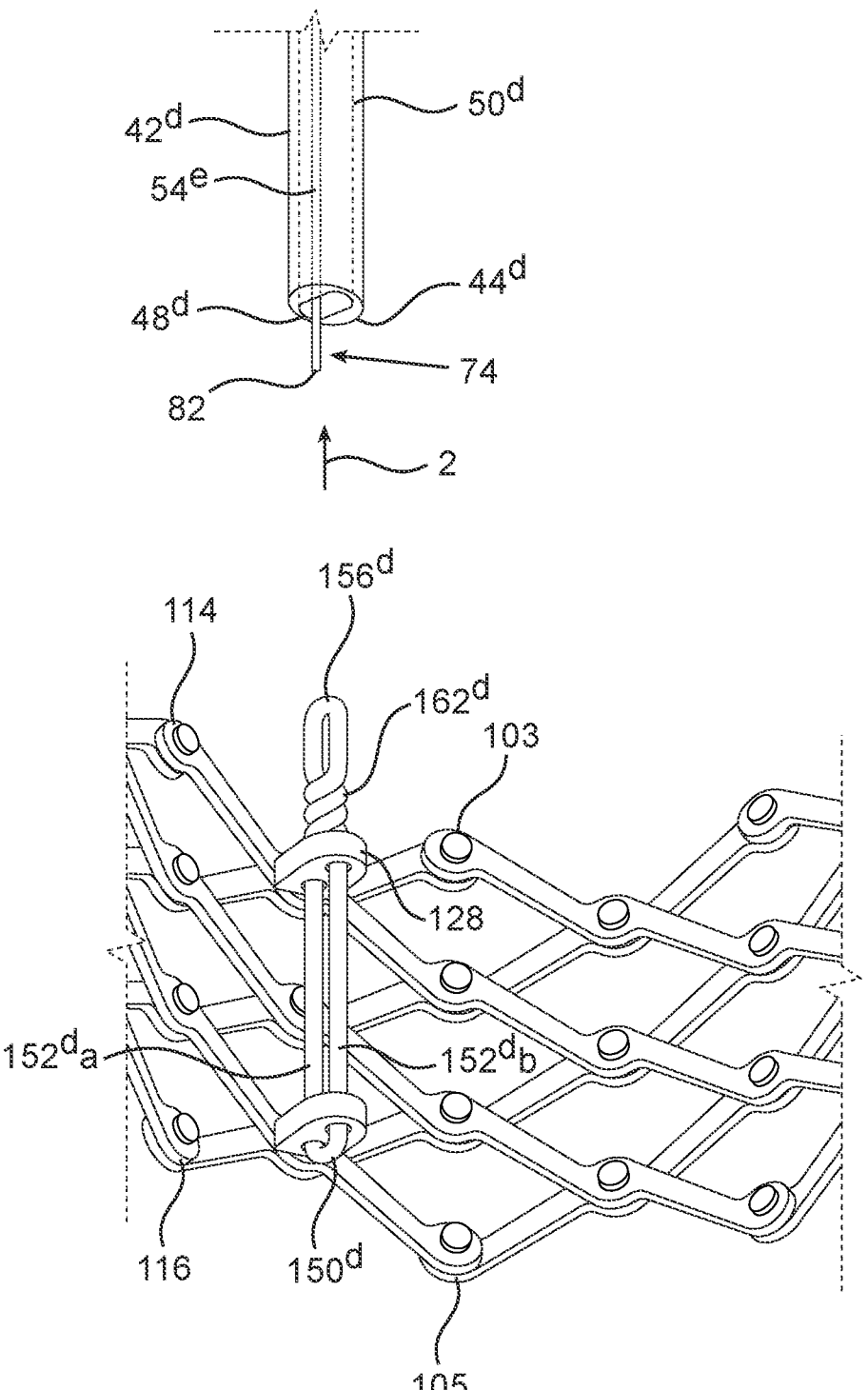

FIG. 10E shows a final stage of expanding and locking the prosthetic valve (100), wherein the actuation assembly 40$^d$ is pulled in the first direction 2 (e.g., the proximal direction), allowing the pull end portion 156$^a$ to slide over and away from the bendable distal portion 74 (i.e., toward and over its free end 82), while the delivery apparatus 12 may be retrieved from the patient's body, leaving the prosthetic valve (100) implanted in the patient.

The plastic deformation of the wire 148$^d$, and specifically that of the axial lock portions 154$^d$, prevents them from unwinding, such that the axial lock portions 154$^d$a and 154$^d$b remain intertwined with each other, together forming the twist 162$^d$, even once the wire 148$^d$ is released from the actuation assembly 40) d.

In this final expanded state, the wire axial portions 152$^d$a and 152$^d$a are tensioned between the guide member 128 and the base member 138, wherein the wire base end portion 150$^d$ disposed over the base member second surface 146, and the twist 162$^d$ disposed the guide member first surface 134, prevent the guide member 128 and the base member 138 from being distanced away from each other, effectively locking the frame 106 in the expanded diameter.

The patient's native anatomy, such as the native aortic annulus in the case of transcatheter aortic valve implantation, may exert radial forces against the prosthetic valve (100) that would strive to compress it. However, twist 162$^d$, formed over the guide member first surface 134, serves as a locking feature preventing such forces from compressing the frame 106, thereby ensuring that the frame 106 remains locked in the desired radially expanded state.

According to some embodiments, the pull end portion 156$^d$ at the end of the twist 162$^a$ does not extend beyond, or proximal to, the outflow apices 114. According to some embodiments, the pull end portion 156$^d$ at the end of the twist 162$^d$ does not extend beyond, or proximal to, the outflow end 103.

According to some embodiments, there is provided a method of expanding and locking a prosthetic valve (100), comprising a step of providing a delivery assembly (10) that includes a prosthetic valve (100) equipped with a plurality of expansion and locking assemblies 126 that include a guide member 128 attached to the frame 106 at a first location, a base member 138 attached to the frame 106 at a second location axially spaced from the first location, and a wire 148$^d$ comprising two wire axial portions 152$^a$ joined at one end of the wire 148$^a$ at a wire base end portion 150$^d$, and at the opposite end of the wire 148$^d$ at a pull end portion 156$^d$. The wire base end portion 150$^d$ is looped over a base member second surface 146, and the wire axial portions 152$^d$ extend therefrom through base member through-holes 140, toward and through guide member through-holes 130.

The delivery assembly (10) also includes a delivery apparatus (12) equipped with a plurality of actuation assemblies 404, wherein each actuation assembly 40$^d$ includes sleeve 42$^d$ having a sleeve lumen or channel 504, a pull member 54$^e$ having a bendable distal portion 74 that can transition from a biased configuration to a non-biased configuration. The pull member 54$^c$ is releasably coupled, via its bendable distal portion 74, to the pull end portion 156$^d$, such that the wire axial portions 152$^d$ extend from the guide member 128, through a sleeve distal opening 48$^c$, into the sleeve channel 504, in which the pull end portion 156$^d$ is looped through the bendable distal portion 74 (over its bent section 78) in a biased configuration of the bendable distal portion 74. The pull member 54$^e$ comprises a first pull-member section extending proximally from the bent section 78 along the sleeve channel 504.

According to some embodiments, the method further comprises a step of approximating the sleeve 42$^a$ to the guide member 128, such that they may, for example, contact each other.

According to some embodiments, the method further comprises a step of utilizing the actuation assembly 40$^d$ and the wire 148$^a$ to expand the frame (106) by approximating the guide member 128 and the base member 138 to each other.

According to some embodiments, the step of utilizing the actuation assembly 40) d and the wire 148$^d$ to expand the frame (106) includes simultaneously applying a pull force in a first direction 2 on the pull member 54$^c$, so as to pull the base member 138 in the first direction 2, while the sleeve 42$^d$ is pressed against the guide member 128, applying a counterforce thereto, so as to hold the guide member 128 in place.

According to some embodiments, the step of utilizing the actuation assembly 40) d and the wire 148$^d$ to expand the frame (106) includes applying a push force in a second direction 4 by the sleeve 42$^d$, so as to push the guide member 128 in a second direction 4, while the wire 148$^d$ applies a counter force, via its wire base end portion 150$^d$, against the base member 138, so as to hold the base member 138 in place.

According to some embodiments, the step of utilizing the actuation assembly 40$^d$ and the wire 148$^d$ to expand the frame (106) includes applying a pull force in a first direction 2 on the pull member 54$^c$, so as to pull the base member 138 in the first direction 2, while applying a push force in a second direction 4 by the sleeve 42$^d$, so as to push the guide member 128 in a second direction 4.

According to some embodiments, the sleeve 42$^d$ comprises a threaded proximal portion 43$^e$, and method further comprises a step of threading the threaded proximal portion 43$^c$, thereby simultaneously rotating the sleeve 42$^d$ around its axis of symmetry and pulling the sleeve 42$^a$ axially away from the guide member 128, so as to intertwine both axial lock portions 154$^d$ over each other, forming a twist 162$^a$ disposed over the guide member 128, while exposing the twist 162$^d$.

According to some embodiments, the step of simultaneously rotating the sleeve 42$^d$ to form the twist 162$^d$ and pulling the sleeve 42$^d$ is executed such that the bendable distal portion 74 remains in its biased configuration within the sleeve channel 50$^d$.

According to some embodiments, the method further comprises a step of releasing the pull member 54$^e$ from the wire 148$^d$, by pulling the sleeve 42$^d$ relative to the bendable distal portion 74, sufficiently to expose the bendable distal portion 74 and allow a second pull-member section 80 thereof to spring away to its free state, thereby transitioning the bendable distal portion 74 to its open or unbiased configuration thereof.

According to some embodiments, the step of releasing the pull member 54$^e$ from the wire 148$^a$ comprises continuously threading the threaded proximal portion 43$^e$. According to alternative embodiments, the step of releasing the pull member 54$^e$ from the wire 148$^d$ comprises axially pulling the sleeve 42$^d$ without threading the threaded proximal portion 43$^e$.

According to some embodiments, the method further comprises a step of retrieving the delivery apparatus (12), including the actuation assemblies 40$^d$, away from the prosthetic valve (100), thereby allowing the pull end portion 156$^a$ to slide away from the bendable distal portion 74.

According to some embodiments, knob 32a can be a rotatable or otherwise operable knob configured to produce radial expansion. For example, rotation of the knob 32d can pull the pull member 54$^e$ while keeping the sleeve 42$^e$ stationary in position. Alternatively, knob 32a can be configured to push the sleeve 42$^d$ while keeping the pull member 54$^e$ stationary in position. In another alternative, knob 32a can be configured to push the sleeve 42$^a$ while the pull member 54$^e$ is also pulled.

According to some embodiments, knob 32b can be a rotatable or otherwise operable knob configured to thread the threaded proximal portion 43$^e$ of sleeve in a manner that simultaneously rotates the sleeve 42$^a$ around its axis of symmetry, so as to facilitate formation of a twist 162$^d$ by intertwining the axial lock portions 154$^d$ over each other, and pulls the sleeve 42$^a$ in an axial direction, for example— to space it away from the guide member 128.

According to some embodiments, knob 32c can be configured to pull the sleeve 42$^d$ in a first direction 2, without applying rotational movement thereto, for example—to expose the bendable distal portion 74 and allow it to transition to the open or unbiased configuration, thereby facilitating release of the pull member 54$^e$ from the wire 148$^d$.

According to some embodiments, the handle 30 can house one or more electric motors which can be actuated by an operator, such as by pressing a button or a switch on the handle 30, to produce movement of components of the delivery apparatus 12. For example, the handle 30 may include one or more motors operable to produce linear movement of components of the actuation assemblies 40$^d$, including the pull members 54$^e$ and/or the sleeves 42$^d$. According to some embodiments, one or more manual or electric control mechanism is configured to produce simultaneous linear and/or rotational movement of all of the pull members 54$^e$ and/or the sleeves 42$^d$.

While pull member 54$^e$ with bendable distal portion 74 is described and illustrated in use with a sleeve 42$^a$ equipped with a threaded proximal portion 43$^d$, it is to be understood that the pull member 54$^c$ can be similarly used in combination with a sleeve 42$^c$ of actuation assembly 40$^c$ as described in conjunction with FIGS. 8A-9F, which does not necessarily include a threaded portion. In such cases, the method can be implemented in a manner similar to that described above in conjunction with FIGS. 10A-10E, except that instead of threading the sleeve to facilitate simultaneous rotational and axial movement thereof, as described for example in conjunction with FIG. 10C, this step is separated to two consecutive steps of first pulling the sleeve 42$^c$ in a manner similar to that described, for example, in conjunction with FIG. 8C or 9C, and then rotating the sleeve 42$^c$ to form the twist 162$^d$ in a manner similar to that described, for example, in conjunction with FIG. 8D or 9D.

Similarly, while any of the other embodiments described above with respect to FIGS. 5A-9F, utilize steps of separately pulling the sleeve 42, as described for example in conjunction with any of the FIGS. 5C, 6C, 7C, 8C and 9C, followed by rotating the sleeve 42 to form a twist 162, as described for example in conjunction with any of the FIGS. 5D, 6D, 7D, 8D and 9D, it is to be understood that the sleeve 42 utilized in any of such embodiments can include a threaded proximal portions, such that rotation and axial movement of the sleeve can be performed simultaneously by threading the sleeve 42, similar to the manner described above in conjunction with FIG. 10C, for example, mutatis mutandis, and in the interest of brevity, all of these alternative configurations and method will not be described further.

According to some embodiments, either one of the guide member 128 and/or the base member 138 comprise a couple of through-holes which are radially spaced from each other, as illustrated throughout FIGS. 3-10E. For example. FIG. 3 shows a guide member 128$^a$ provided with two guide member through-holes 130$^a$, such that guide member through-hole 130$^a$b is positioned radially inward relative to guide member through-hole 130$^a$a. Similarly, base member 138$^a$ provided with two base member through-holes 140$^a$, such that base member through-hole 140$^a$b is positioned radially inward relative to base member through-hole 140$^a$a.

According to some embodiments, either one of the guide member 128$^b$ and/or the base member 138$^b$ comprise a couple of through-holes which are laterally spaced from each other, as illustrated in FIG. 11. Specifically. FIG. 11 shows a guide member 128$^b$ provided with guide member through-holes 130$^a$a and 130$^a$b spaced apart from each other along a lateral direction, which may be also defined as a direction along the circumference of the frame 106, while both are equally distance in the radial direction from the central axis of the prosthetic valve. Similarly, base member 138$^b$ provided with base member through-holes 140$^a$a and 140$^a$b spaced apart from each other along a lateral direction, while both are equally distance in the radial direction from the central axis of the prosthetic valve.

While two relative orientations of guide member through-holes 130 and base member through-holes 140 are illustrated, spaced apart from each other at either the radial or lateral direction, it is to e understood that any other relative orientation and spacing there-between is contemplated. For example, any of the guide member through-holes 130 or base member through-holes 140 can be diagonally spaced from each other.

It is to be understood that features from guide members 128$^a$. 128$^b$ and 128$^c$ can be combined. For example, a guide member 128 can be provided as an elongated member, similar to that shown for guide member 128$^d$ in FIG. 4, while having its guide member through-holes 130 laterally spaced apart from each other, such as shown for guide member 128$^c$ in FIG. 11. Similarly, features from base members 138$^a$, 138$^b$ and 138$^c$ can be combined. For example, a base member 138 can be provided as an elongated member, while having its base member through-holes 140 laterally spaced apart from each other.

It is to be further understood that any type of guide members 128 and/or base members 138, can be used in combination with any of the wires 148 and actuation assemblies 40) described hereinabove with respect to FIGS. 5A-5F, 6A-6F, 7A-7F, 8A-8F, 9A-9F and/or 10A-10E.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A prosthetic valve, comprising:
a frame having an inflow end and an outflow end, wherein the frame is movable between a radially compressed and a radially expanded state;
at least one expansion and locking mechanism, comprising:
a guide member, coupled to the frame at a first location, and comprising: a guide member first surface, a guide member second surface, and two guide member through-holes extending between the guide member first surface and the guide member second surface;
a base member, coupled to the frame at a second location spaced apart from the first location, and comprising: a base member first surface, a base member second surface, and two base member through-holes extending between the base member first surface and the base member second surface; and
a wire comprising: a wire base end portion looped over the base member second surface, and two wire axial portions extending from the base member second surface, through the base member through-holes, toward and through the guide member through-holes;
wherein movement of the base member in a first direction, relative to the guide member, causes the frame to foreshorten axially and expand radially;
wherein each wire axial portion defines an axial lock portion at the region that extends beyond the guide member first surface; and
wherein the axial lock portions are configured to form together a twist disposed over the guide member first surface when they are intertwined together, such that when the twist is formed, it is configured to prevent, along with the wire base end portion, recompression of the frame.

Example 2. The prosthetic valve of any example herein, particularly example 1, wherein the wire comprises a plastically deformable material.

Example 3. The prosthetic valve of any example herein, particularly any one of examples 1 to 2, wherein the guide member comprises a guide member fastener.

Example 4. The prosthetic valve of any example herein, particularly any one of examples 1 to 3, wherein the base member comprises a base member fastener.

Example 5. The prosthetic valve of any example herein, particularly any one of examples 1 to 4, wherein the frame comprises inflow apices, outflow apices, and non-apical junctions between the inflow apices and the outflow apices, and wherein the first location is a non-apical junction.

Example 6. The prosthetic valve of any example herein, particularly any one of examples 1 to 5, wherein the diameter of each guide member through-hole and the diameter of each base member through-hole, is not greater than 150% of the diameter of the wire.

Example 7. The prosthetic valve of any example herein, particularly any one of examples 1 to 5, wherein the diameter of each guide member through-hole and the diameter of each base member through-hole, is not greater than 120% of the diameter of the wire.

Example 8. The prosthetic valve of any example herein, particularly any one of examples 1 to 5, wherein the diameter of each guide member through-hole and the diameter of each base member through-hole, is not greater than 110% of the diameter of the wire.

Example 9. The prosthetic valve of any example herein, particularly any one of examples 1 to 5, wherein the diameter of each guide member through-hole and the diameter of each base member through-hole, is not greater than 105% of the diameter of the wire.

Example 10. The prosthetic valve of any example herein, particularly any one of examples 1 to 9, wherein each axial lock portion comprises an attachment interface.

Example 11. The prosthetic valve of any example herein, particularly example 10, wherein the attachment interface is an eyelet.

Example 12. The prosthetic valve of any example herein, particularly any one of examples 1 to 9, wherein the wire defines a closed loop, such that both wire axial portions are joined by a pull end portion, opposite to the wire base end portion.

Example 13. The prosthetic valve of any example herein, particularly any one of examples 1 to 12, wherein the guide member through-holes are radially spaced from each other.

Example 14. The prosthetic valve of any example herein, particularly any one of examples 1 to 12, wherein the guide member through-holes are laterally spaced from each other.

Example 15. The prosthetic valve of any example herein, particularly any one of examples 1 to 12, wherein the base member through-holes are radially spaced from each other.

Example 16. The prosthetic valve of any example herein, particularly any one of examples 1 to 12, wherein the base member through-holes are laterally spaced from each other.

Example 17. The prosthetic valve of any example herein, particularly any one of examples 1 to 16, wherein further comprising the twist formed by the axial lock portions intertwined with each other.

Example 18. The prosthetic valve of any example herein, particularly example 17, wherein the twist does not extend proximally beyond the outflow end.

Example 19. A delivery assembly, comprising:

a prosthetic valve comprising:

a frame having an inflow end and an outflow end, wherein the frame is movable between a radially compressed and a radially expanded state;

at least one expansion and locking mechanism, comprising:

a guide member coupled to the frame at a first location, the guide member defined between a guide member first surface and a guide member second surface;

a base member, coupled to the frame at a second location spaced apart from the first location; and a wire comprising: a wire base end portion looped over the base member, and two wire axial portions extending from the wire base end portion, through the base member, toward and through guide member;

a delivery apparatus comprising:

a handle;

a delivery shaft extending distally from the handle; and at least one actuation assembly extending from the handle through the delivery shaft, the actuation assembly comprising a sleeve, the sleeve comprising:

a sleeve outer surface;

a sleeve distal end;

at least one sleeve distal opening; and at least one sleeve channel extending from the at least one sleeve distal opening;

wherein the sleeve is configured to accommodate a portion of the wire within the at least one sleeve channel, such that the portion of the wire accommodated within the sleeve is axially movable with respect to the sleeve;

wherein movement of the base member in a first direction, relative to the guide member, causes the frame to foreshorten axially and expand radially;

wherein the wire axial portions define axial lock portions at the region that extends beyond the guide member first surface; and wherein rotation of the sleeve is configured to intertwine the wire axial portions so as to form a twist disposed over the guide member first surface, such that when the twist is formed, it is configured to prevent, along with the wire base end portion, recompression of the frame.

Example 20. The delivery assembly of any example herein, particularly example 19, wherein the wire comprises a plastically deformable material.

Example 21. The delivery assembly of any example herein, particularly any one of examples 19 to 20, wherein the guide member comprises a guide member fastener.

Example 22. The prosthetic valve of any example herein, particularly any one of examples 19 to 21, wherein the base member comprises a base member fastener.

Example 23. The delivery assembly of any example herein, particularly any one of examples 19 to 22, wherein the frame comprises inflow apices, outflow apices, and non-apical junctions between the inflow apices and the outflow apices, and wherein the first location is a non-apical junction.

Example 24. The delivery assembly of any example herein, particularly any one of examples 19 to 23, wherein the diameter of each guide member through-hole and the diameter of each base member through-hole, is not greater than 150% of the diameter of the wire.

Example 25. The delivery assembly of any example herein, particularly any one of examples 19 to 23, wherein the diameter of each guide member through-hole and the diameter of each base member through-hole, is not greater than 120% of the diameter of the wire.

Example 26. The delivery assembly of any example herein, particularly any one of examples 19 to 23, wherein the diameter of each guide member through-hole and the diameter of each base member through-hole, is not greater than 110% of the diameter of the wire.

Example 27. The delivery assembly of any example herein, particularly any one of examples 19 to 23, wherein the diameter of each guide member through-hole and the diameter of each base member through-hole, is not greater than 105% of the diameter of the wire.

Example 28. The delivery assembly of any example herein, particularly any one of examples 19 to 27, wherein the sleeve has sufficient rigidity, configured to resist bending or buckling thereof, when the sleeve is pressed against, and applies a distally oriented force against, the guide member.

Example 29. The delivery assembly of any example herein, particularly any one of examples 19 to 28, wherein the at least one sleeve distal opening comprises two sleeve distal opening, and wherein the at least one sleeve channel comprises two sleeve channels.

Example 30. The delivery assembly of any example herein, particularly example 29, wherein the diameter of each sleeve channel is not greater than 150% of the diameter of the wire.

Example 31. The delivery assembly of any example herein, particularly example 29, wherein the diameter of each sleeve channel is not greater than 120% of the diameter of the wire.

Example 32. The delivery assembly of any example herein, particularly example 29, wherein the diameter of each sleeve channel is not greater than 110% of the diameter of the wire.

Example 33. The delivery assembly of any example herein, particularly example 29, wherein the diameter of each sleeve channel is not greater than 105% of the diameter of the wire.

Example 34. The delivery assembly of any example herein, particularly example 29, wherein the sleeve further comprises two sleeve side openings defined at the sleeve outer surface, such that each sleeve channel extends between a corresponding sleeve distal opening and a corresponding sleeve side opening.

Example 35. The delivery assembly of any example herein, particularly example 34, wherein each wire axial portion extends into a corresponding sleeve channel through the corresponding sleeve distal opening, and exits the sleeve channel through the corresponding sleeve side opening.

Example 36. The delivery assembly of any example herein, particularly example 34, wherein each actuation assembly further comprises a couple of pull members extending from the handle, and wherein each pull member is coupled to an attachment interface of the corresponding wire axial portion.

Example 37. The delivery assembly of any example herein, particularly example 36, wherein each wire axial portion extends into a corresponding sleeve channel through the corresponding sleeve distal opening, wherein the attachment interface is positioned within the sleeve channel, and wherein the wire axial portion exits the sleeve channel through the corresponding sleeve side opening.

Example 38. The delivery assembly of any example herein, particularly any one of examples 36 to 37, wherein the diameter of each sleeve channel is not greater than 150% of the diameter of the pull member.

Example 39. The delivery assembly of any example herein, particularly any one of examples 36 to 37, wherein the diameter of each sleeve channel is not greater than 120% of the diameter of the pull member.

Example 40. The delivery assembly of any example herein, particularly any one of examples 36 to 37, wherein the diameter of each sleeve channel is not greater than 110% of the diameter of the pull member.

Example 41. The delivery assembly of any example herein, particularly any one of examples 36 to 37, wherein the diameter of each sleeve channel is not greater than 105% of the diameter of the pull member.

Example 42. The delivery assembly of any example herein, particularly any one of examples 36 to 37, wherein the diameter of each sleeve channel is not greater than 150% of the diameter of the attachment interface.

Example 43. The delivery assembly of any example herein, particularly any one of examples 36 to 37, wherein the diameter of each sleeve channel is not greater than 120% of the diameter of the attachment interface.

Example 44. The delivery assembly of any example herein, particularly any one of examples 36 to 37, wherein the diameter of each sleeve channel is not greater than 110% of the diameter of the attachment interface.

Example 45. The delivery assembly of any example herein, particularly any one of examples 36 to 37, wherein the diameter of each sleeve channel is not greater than 105% of the diameter of the attachment interface.

Example 46. The delivery assembly of any example herein, particularly any one of examples 34 to 45, wherein each actuation assembly further comprises a cutting shaft extending concentrically over the sleeve, and movable axially relative thereto, the cutting shaft comprising a blade.

Example 47. The delivery assembly of any example herein, particularly example 46, wherein the blade is configured to cut the wire.

Example 48. The delivery assembly of any example herein, particularly example 29, wherein the sleeve channels extend axially along the length of the sleeve.

Example 49. The delivery assembly of any example herein, particularly example 48, wherein each wire axial extension comprises an eyelet, and wherein each actuation assembly further comprises two pull members, each pull member looped through the eyelet such that two strands thereof extend proximally from the eyelet.

Example 50. The delivery assembly of any example herein, particularly example 49, wherein the diameter of each sleeve channel is not greater than 300% of the diameter of the diameter of a single strand.

Example 51. The delivery assembly of any example herein, particularly example 49, wherein the diameter of each sleeve channel is not greater than 250% of the diameter of the diameter of a single strand.

Example 52. The delivery assembly of any example herein, particularly example 49, wherein the diameter of each sleeve channel is not greater than 210% of the diameter of the diameter of a single strand.

Example 53. The delivery assembly of any example herein, particularly any one of examples 19 to 27, wherein the wire defines a closed loop, such that both wire axial portions are joined by a pull end portion, opposite to the wire base end portion.

Example 54. The delivery assembly of any example herein, particularly example 53, wherein the actuation assembly further comprises a pull member attached to a quick release hook, configured to transition between a closed configuration and an open configuration.

Example 55. The delivery assembly of any example herein, particularly example 54, wherein the quick release hook comprises a hook body, and a spring-loaded gate hinged thereto.

Example 56. The delivery assembly of any example herein, particularly any one of examples 54 to 55, wherein the sleeve channel is dimensioned to accommodate the quick release hook in a closed configuration.

Example 57. The delivery assembly of any example herein, particularly example 53, wherein the actuation assembly further comprises a pull member looped through the pull end portion such that two strands of the pull member extend proximally from the pull end portion.

Example 58. The delivery assembly of any example herein, particularly example 53, wherein the actuation assembly further comprises a pull member having a bendable distal portion made of a shape-memory material and configured to transition between a biased configuration, in which the bendable distal portion is bent over itself, and an unbiased configuration, and wherein the pull end portion is releasably attached to the bendable distal portion in its biased configuration.

Example 59. The delivery assembly of any example herein, particularly any one of examples 19 to 58, wherein the prosthetic valve further comprises the twist formed by the axial lock portions intertwined with each other.

Example 60. The delivery assembly of any example herein, particularly example 59, wherein the twist does not extend proximally beyond the outflow end.

Example 61. The delivery assembly of any example herein, particularly any one of examples 19 to 60, wherein the sleeve further comprises a threaded proximal portion.

Example 62. The delivery assembly of any example herein, particularly example 61, wherein the threaded proximal portion is attached to the handle.

Example 63. A method for expanding and locking a prosthetic valve, comprising the steps of:

providing a delivery assembly comprising a delivery apparatus releasably coupled to a prosthetic valve, wherein the delivery apparatus comprises a handle and at least one actuation assembly extending therefrom, each actuation assembly comprising a sleeve with at least one sleeve channel, and wherein the prosthetic valve comprises frame and at least one expansion and locking assembly, each expansion and locking assembly comprising a guide member coupled to the frame at a first location, a base member coupled to the frame at a second location which is axially spaced from the first location, and a wire having a wire base end portion looped over a surface of the base member, and two wire axial portions extending from the wire base end portion, through the base member, toward and through the guide member;

approximating the sleeve to the guide member such that a distal end thereof contacts the guide member; and utilizing the actuation assembly and the wire to approximate the base member and the guide member toward each other, thereby expanding the frame.

Example 64. The method of any example herein, particularly example 63, wherein the step of utilizing the actuation assembly and the wire comprises applying a pull force on the wire, while holding the sleeve in place so as to apply a counter-force against the guide member.

Example 65. The method of any example herein, particularly example 63, wherein the step of utilizing the actuation assembly and the wire comprises pushing the sleeve to apply a pushing force against the guide member, thereby moving the guide member toward the base member, while keeping the wire tensioned in a manner that will hold the base member in place.

Example 66. The method of any example herein, particularly example 63, wherein the step of utilizing the actuation assembly and the wire comprises simultaneously applying a pull force on the wire, while pushing the sleeve to apply a pushing force against the guide member.

Example 67. The method of any example herein, particularly any one of examples 64 to 66, wherein applying pull force on the wire comprises applying a pull force to two pull members that extend from the handle, and are coupled to attachment interfaces of the axial pull portions.

Example 68. The method of any example herein, particularly any one of examples 64 to 66, wherein applying pull force on the wire comprises simultaneously applying a pull force to a total of four strands of two pull members that extend from the handle, wherein two strands of each pull members extend proximally from an eyelet of each wire axial portion, through which the corresponding pull member is looped.

Example 69. The method of any example herein, particularly any one of examples 64 to 66, wherein applying pull force on the wire comprises applying a pull force to a pull member attached to a quick release hook, wherein a pull end portion of the wire is looped through the quick release hook, and wherein the quick release hook is retained in a closed state within the sleeve channel.

Example 70. The method of any example herein, particularly any one of examples 64 to 66, wherein applying pull force on the wire comprises applying a pull force to a pull member having a bendable distal portion made of a shape-memory material, wherein the bendable distal portion is configured to transition between a biased configuration, in which the bendable distal portion is bent over itself, and an unbiased configuration, wherein a pull end portion of the wire is releasably attached to the bendable distal portion in its biased configuration, and wherein the bendable distal portion is retained in the biased configuration within the sleeve channel.

Example 71. The method of any example herein, particularly any one of examples 64 to 66, wherein applying pull force on the wire comprises applying a pull force to two strands of a pull member that extends from the handle and is looped through a pull end portion of the wire.

Example 72. The method of any example herein, particularly any one of examples 63 to 66, further comprising a step of pulling the sleeve away from the guide member, thereby exposing axial lock portions extending between the guide member and a distal end of the sleeve.

Example 73. The method of any example herein, particularly example 72, wherein each wire axial portion comprises an attachment interface, and wherein the step of pulling the sleeve is executed such that the attachment interfaces remain within the at least one sleeve channel.

Example 74. The method of any example herein, particularly example 72, wherein each wire axial portion comprises an eyelet, and wherein the step of pulling the sleeve is executed such that the eyelets remain within the at least one sleeve channel.

Example 75. The method of any example herein, particularly example 72, wherein the wire comprises a pull end portion looped through a quick release hook which is attached to a pull member extending therefrom, and wherein the step of pulling the sleeve is executed such that the quick release hook remains within the sleeve channel.

Example 76. The method of any example herein, particularly example 72, wherein the wire comprises a pull end portion looped through a quick release hook which is attached to a pull member extending therefrom, and wherein the step of pulling the sleeve is executed such that the pull end portion remains within the sleeve channel.

Example 77. The method of any example herein, particularly example 72, wherein the wire comprises a pull end portion looped through a bendable distal portion of a pull member, in a biased configuration of the bendable distal portion in which it is folded over itself, and wherein the step of pulling the sleeve is executed such that the bendable distal portion remains within the sleeve channel.

Example 78. The method of any example herein, particularly example 72, wherein the wire comprises a pull end portion looped through a bendable distal portion of a pull member, in a biased configuration of the bendable distal portion in which it is folded over itself, and wherein the step of pulling the sleeve is executed such that the pull end portion remains within the sleeve channel.

Example 79. The method of any example herein, particularly example 72, wherein the wire axial portions extend into the sleeve channel, and are joined together via a pull end portion of the wire, wherein a pull member is looped through the pull end portion, and wherein the step of pulling the sleeve is executed such that the pull end portion remains within the corresponding sleeve channels.

Example 80. The method of any example herein, particularly example 72, further comprising a step of rotating the sleeve around its axis of symmetry, so as to intertwine the axial lock portions over each other, thereby forming a twist disposed over the guide member.

Example 81. The method of any example herein, particularly example 72, wherein the sleeve comprises a threaded proximal portion, wherein the step of pulling the sleeve away from the guide member is performed by threading the threaded proximal portion so as to facilitate rotational movement of the sleeve around its axis of symmetry, simultaneous to the axial pulling of the sleeve, and wherein the rotational movement is configured to intertwine the axial lock portions over each other, thereby forming a twist disposed over the guide member.

Example 82. The method of any example herein, particularly any one of examples 80 to 81, wherein the wire axial portions extend into sleeve channels of the sleeve, exit the sleeve channels through sleeve side openings, and extend proximally from the sleeve side openings, and wherein the method further comprises sliding a cutting shaft over the sleeve toward the side openings, thereby cutting the axial lock portions.

Example 83. The method of any example herein, particularly any one of examples 80 to 81, wherein the wire axial portions extend into sleeve channels of the sleeve, wherein pull members, which are attached to the wire axial portions within the sleeve channels, exit the sleeve channels through sleeve side openings, and extend proximally from the sleeve side openings, and wherein the method further comprises sliding a cutting shaft over the sleeve toward the side openings, thereby cutting the pull members.

Example 84. The method of any example herein, particularly any one of examples 80 to 81, wherein the wire axial portions extend into sleeve channels of the sleeve, wherein pull members are looped through eyelets of the wire axial portions, such that two strands of each pull member extend proximally from the eyelet, and wherein the method further comprises a step of pulling a single strand of each pull member, while allowing the opposite strand to freely move toward a corresponding eyelet, until it is released therefrom.

Example 85. The method of any example herein, particularly any one of examples 80 to 81, wherein the wire axial portions extend into the sleeve channel, and are joined together via a pull end portion of the wire, which is looped through a quick release hook attached to a pull member extending proximally therefrom, wherein the quick release hook is retained in a closed configuration within the sleeve channel, and wherein the method further comprises pulling the sleeve relative to the quick release hook, so as to expose the quick release hook, allowing it to transition to its open configuration, thereby allowing the pull end portion of the wire to disengage therefrom.

Example 86. The method of any example herein, particularly any one of examples 80 to 81, wherein the wire axial portions extend into the sleeve channel, and are joined together via a pull end portion of the wire which is looped through a bendable distal portion of a pull member, wherein the bendable distal portion is retained in a biased configuration in which it is folded over itself within the sleeve channel, and wherein the method further comprises pulling the sleeve relative to the bendable distal portion, so as to expose a second pull-member section of the pull-member section and allowing it to transition to its unbiased configuration, thereby allowing the pull end portion of the wire to disengage therefrom.

Example 87. The method of any example herein, particularly any one of examples 80 to 81, wherein the wire axial portions extend into the sleeve channel, and are joined together via a pull end portion of the wire, wherein a pull member is looped through the pull end portion such that two strands of the pull member extend proximally from the pull end portion, and wherein the method further comprises a step of pulling a single strand of the pull member, while allowing the opposite strand to freely move toward the pull end portion, until it is released therefrom.

Example 88. The method of any example herein, particularly any one of examples 82 to 87, further comprising a step of retrieving the delivery apparatus, along with the actuation assemblies, from the prosthetic valve.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

In view of the many possible embodiments to which the principles of the disclosure may be applied, it should be recognized that the illustrated embodiments are only preferred examples and should not be taken as limiting the scope. Rather, the scope is defined by the following claims. We therefore claim all that comes within the scope and spirit of these claims.

The invention claimed is:

1. A prosthetic valve, comprising:

a frame having an inflow end and an outflow end, wherein the frame is movable between a radially compressed and a radially expanded state;

at least one expansion and locking mechanism, comprising:

a guide member, coupled to the frame at a first location, and comprising:

a guide member first surface, a guide member second surface, and two guide member through-holes extending between the guide member first surface and the guide member second surface;

a base member, coupled to the frame at a second location spaced apart from the first location, and comprising:

a base member first surface, a base member second surface, and two base member through-holes extending between the base member first surface and the base member second surface; and a wire comprising:

a wire base end portion looped over the base member second surface, and two wire axial portions extending from the base member second surface, through the base member through-holes, toward and through the guide member through-holes;

wherein movement of the base member in a first direction, relative to the guide member, causes the frame to foreshorten axially and expand radially;

wherein each wire axial portion defines an axial lock portion at a region that extends beyond the guide member first surface; and wherein the axial lock portions are configured to form together a twist disposed over the guide member first surface when they are intertwined together, such that when the twist is formed, it is configured to prevent, along with the wire base end portion, recompression of the frame.

2. The prosthetic valve of claim 1, wherein the wire defines a closed loop, such that both wire axial portions are joined by a pull end portion, opposite to the wire base end portion.

3. The prosthetic valve of claim 1, further comprising the twist formed by the axial lock portions intertwined with each other.

4. A delivery assembly, comprising:

a prosthetic valve comprising:

a frame having an inflow end and an outflow end, wherein the frame is movable between a radially compressed and a radially expanded state;

at least one expansion and locking mechanism, comprising:

a guide member coupled to the frame at a first location, the guide member defined between a guide member first surface and a guide member second surface;

a base member, coupled to the frame at a second location spaced apart from the first location; and a wire comprising:

a wire base end portion looped over the base member, and two wire axial portions extending from the wire base end portion, through the base member, toward and through guide member;

a delivery apparatus comprising:

a handle;

a delivery shaft extending distally from the handle; and at least one actuation assembly extending from the handle through the delivery shaft, the actuation assembly comprising a sleeve, the sleeve comprising:

a sleeve outer surface;

a sleeve distal end;

at least one sleeve distal opening; and at least one sleeve channel extending from the at least one sleeve distal opening;

wherein the sleeve is configured to accommodate a portion of the wire within the at least one sleeve channel, such that the portion of the wire accommodated within the sleeve is axially movable with respect to the sleeve;

wherein movement of the base member in a first direction, relative to the guide member, causes the frame to foreshorten axially and expand radially;

wherein the wire axial portions define axial lock portions at a region that extends beyond the guide member first surface; and wherein rotation of the sleeve is configured to intertwine the wire axial portions so as to form a twist disposed over the guide member first surface, such that when the twist is formed, it is configured to prevent, along with the wire base end portion, recompression of the frame.

5. The delivery assembly of claim 4, wherein the at least one sleeve distal opening comprises two sleeve distal openings, and wherein the at least one sleeve channel comprises two sleeve channels.

6. The delivery assembly of claim 5, wherein the sleeve further comprises two sleeve side openings defined at the sleeve outer surface, such that each sleeve channel extends between a corresponding sleeve distal opening and a corresponding sleeve side opening.

7. The delivery assembly of claim 6, wherein each wire axial portion extends into a corresponding sleeve channel through the corresponding sleeve distal opening, and exits the sleeve channel through the corresponding sleeve side opening.

8. The delivery assembly of claim 6, wherein each actuation assembly further comprises a cutting shaft extending concentrically over the sleeve, and movable axially relative thereto, the cutting shaft comprising a blade.

9. The delivery assembly of claim 5, wherein the sleeve channels extend axially along a length of the sleeve.

10. The delivery assembly of claim 9, wherein each wire axial extension comprises an eyelet, and wherein each actuation assembly further comprises two pull members, each pull member looped through the eyelet such that two strands thereof extend proximally from the eyelet.

11. The delivery assembly of claim 4, wherein the wire defines a closed loop, such that both wire axial portions are joined by a pull end portion, opposite to the wire base end portion.

12. The delivery assembly of claim 11, wherein the actuation assembly further comprises a pull member attached to a quick release hook, configured to transition between a closed configuration and an open configuration.

13. The delivery assembly of claim 11, wherein the actuation assembly further comprises a pull member looped through the pull end portion such that two strands of the pull member extend proximally from the pull end portion.

14. The delivery assembly of claim 11, wherein the actuation assembly further comprises a pull member having a bendable distal portion made of a shape-memory material and configured to transition between a biased configuration, in which the bendable distal portion is bent over itself, and an unbiased configuration, and wherein the pull end portion is releasably attached to the bendable distal portion in its biased configuration.

15. The prosthetic valve of claim 4, wherein the prosthetic valve further comprises the twist formed by the axial lock portions intertwined with each other.

16. A method for expanding and locking a prosthetic valve, comprising the steps of:

providing a delivery assembly comprising a delivery apparatus releasably coupled to a prosthetic valve, wherein the delivery apparatus comprises a handle and at least one actuation assembly extending therefrom, each actuation assembly comprising a sleeve with at least one sleeve channel, and wherein the prosthetic valve comprises a frame and at least one expansion and locking assembly, each expansion and locking assembly comprising a guide member coupled to the frame at a first location, a base member coupled to the frame at a second location which is axially spaced from the first location, and a wire having a wire base end portion looped over a surface of the base member, and two wire axial portions extending from the wire base end portion, through the base member, toward and through the guide member;

approximating the sleeve to the guide member such that a distal end thereof contacts the guide member;

utilizing the actuation assembly and the wire to approximate the base member and the guide member toward each other, thereby expanding the frame; and rotating the sleeve around its axis of symmetry, so as to intertwine axial lock portions of the wire axial portions over each other, thereby forming a twist disposed over the guide member.

17. The method of claim 16, further comprising a step of pulling the sleeve away from the guide member, thereby exposing the axial lock portions extending between the guide member and a distal end of the sleeve.

18. The method of claim 17, wherein the sleeve comprises a threaded proximal portion, wherein the step of pulling the sleeve away from the guide member is performed by threading the threaded proximal portion so as to facilitate rotational movement of the sleeve around its axis of symmetry, simultaneous to the pulling of the sleeve away from the guide member, and wherein the rotational movement is configured to intertwine the axial lock portions over each other, thereby forming the twist disposed over the guide member.

19. The method of claim 16, wherein the wire axial portions extend into the sleeve channel, and are joined together via a pull end portion of the wire which is looped through a bendable distal portion of a pull member, wherein the bendable distal portion is retained in a biased configuration in which it is folded over itself within the sleeve channel, and wherein the method further comprises pulling the sleeve relative to the bendable distal portion, so as to expose the bendable distal portion and allowing it to transition to its unbiased configuration, thereby allowing the pull end portion of the wire to disengage therefrom.

* * * * *